US009751081B2

(12) United States Patent
Tennyson et al.

(10) Patent No.: US 9,751,081 B2
(45) Date of Patent: Sep. 5, 2017

(54) SELF-REGENERATING ANTIOXIDANT CATALYSTS AND METHODS OF USING THE SAME

(71) Applicant: Clemson University, Anderson, SC (US)

(72) Inventors: Andrew Gregory Tennyson, Seneca, SC (US); Yamin Htet, Clemson, SC (US); Anshuman Mangalum, Central, SC (US)

(73) Assignee: Clemson University, Anderson, SC (US)

( * ) Notice: Subject to any disclaimer, the term of this patent is extended or adjusted under 35 U.S.C. 154(b) by 85 days.

(21) Appl. No.: 14/955,936

(22) Filed: Dec. 1, 2015

(65) Prior Publication Data

US 2016/0151773 A1  Jun. 2, 2016

Related U.S. Application Data

(60) Provisional application No. 62/085,862, filed on Dec. 1, 2014.

(51) Int. Cl.
| | |
|---|---|
| *C07F 15/00* | (2006.01) |
| *B01J 31/22* | (2006.01) |
| *A61L 27/28* | (2006.01) |
| *A61L 27/50* | (2006.01) |
| *A61L 27/54* | (2006.01) |

(52) U.S. Cl.
CPC ........... *B01J 31/2295* (2013.01); *A61L 27/50* (2013.01); *A61L 27/54* (2013.01); *C07F 15/0046* (2013.01); *A61L 2400/02* (2013.01)

(58) Field of Classification Search
CPC ............... B01J 31/2295; B01J 31/2269; C07F 15/0046; A61L 27/50; A61L 27/54

USPC .......................................... 548/105; 556/136
See application file for complete search history.

(56) References Cited

U.S. PATENT DOCUMENTS

| | | | |
|---|---|---|---|
| 2007/0082881 A1 | 4/2007 | MacDonnell et al. | |
| 2007/0191944 A1 | 8/2007 | Contreras et al. | |
| 2012/0141432 A1 | 6/2012 | Piganelli et al. | |

FOREIGN PATENT DOCUMENTS

| | | |
|---|---|---|
| BR | PI1001555 A2 | 10/2014 |
| CN | 101264347 | 9/2008 |
| JP | H11346715 | 12/1999 |
| JP | 2000-312716 | 11/2000 |
| JP | 2008-156440 | 7/2008 |
| KR | 2010-0022237 | 3/2010 |
| PL | 211845 B1 | 7/2012 |
| WO | WO 01/30790 A1 | 5/2001 |
| WO | WO 02/02572 A1 | 1/2002 |
| WO | WO 02/059135 A1 | 8/2002 |
| WO | WO 02/076998 A2 | 10/2002 |
| WO | WO 03/035078 A1 | 5/2003 |
| WO | WO 03/090809 A1 | 11/2003 |
| WO | WO 2004/005304 A1 | 1/2004 |
| WO | WO 2004/047772 A2 | 6/2004 |

(Continued)

OTHER PUBLICATIONS

Al-Mohammed et al. "1-Carboxymethyl-3-octylimidazolium bromide" *Acta Crystallographica Section E* E67:o1701 (2011).

(Continued)

*Primary Examiner* — Porfirio Nazario Gonzalez
(74) *Attorney, Agent, or Firm* — Myers Bigel, P.A.

(57) ABSTRACT

The present invention relates to self-regenerating antioxidant catalysts and methods of using the same.

20 Claims, 15 Drawing Sheets

(56) References Cited

FOREIGN PATENT DOCUMENTS

| WO | WO 2004/096819 A1 | 11/2004 |
|---|---|---|
| WO | WO 2006/018649 A1 | 2/2006 |
| WO | WO 2007/101997 A1 | 9/2007 |
| WO | WO 2007/135410 A1 | 11/2007 |
| WO | WO 2011/137503 A1 | 11/2011 |
| WO | WO 2012/155004 A2 | 11/2012 |
| WO | WO 2013/038395 A1 | 3/2013 |
| WO | WO 2013/053809 A1 | 4/2013 |
| WO | WO 2014/200497 A1 | 12/2014 |

OTHER PUBLICATIONS

Amor et al. "Neutral and cationic di( tert-butyl) cyclopentadienyl titanium, zirconium and hafnium complexes: Dynamic NMR study of the ligand-free cations [M( 1,3-$^t$Bu$_2$-$\eta^5$-C$_5$H$_3$) ($\eta^5$-C$_5$H$_5$) (CH$_3$)]$^+$ (M =Zr, Hf)" *Journal of Organometallic Chemistry* 535:155-168 (1997).

Arduengo et al. "A Stable Crystalline Carbene" *Journal of the American Chemical Society* 113(1):361-363 (1991).

Arnold et al. "Abnormal N-heterocyclic carbenes" *Coordination Chemistry Reviews* 251(5-6):596-609 (2007) (Abstract Only).

Arslan et al. "Bromido[1-($\eta^6$-4-tert-butylbenzyl)-3-(2,4,6-trimethylbenzyl)benzimidazol-2-ylidene]chloridoruthenium(II)" *Acta Crystallographica Section E* E65:m97-m98 (2009).

Arslan et al. "Dichlorido[1-(2-methylbenzyl)-3-($\eta^6$-2,4,6-trimethylbenzyl)-1H-2,3-dihydrobenzimidazol-2-ylidene]ruthenium(II) dichloromethane solvate" *Acta Crystallographica Section E* E65:m243-m244 (2009).

Azua et al. "Iridium NHC Based Catalysts for Transfer Hydrogenation Processes Using Glycerol as Solvent and Hydrogen Donor" *Organometallics* 30:5532-5536 (2011).

Berlin et al. "Ruthenium-Catalyzed Ring-Closing Metathesis to Form Tetrasubstituted Olefins" *Organic Letters* 9(7):1339-1342 (2007).

Bo et al. "*fac* versus *mer* Coordination for a Tridentate Diethylene Glyclolate Ligand in Tantalum Complexes: A Combined Experimental and Theoretical Study" *Organometallics* 25:3336-3344 (2006).

Borguet et al. "Assessing the ligand properties of 1,3-dimesitylbenzimidazol-2-ylidene in ruthenium-catalyzed olefin metathesis" *Dalton Transactions* 42:7287-7296 (2013).

Bosch et al. "Internally Phospine-Stabilized Zirconocene Cations Employing Substituted ((Diarylphosphino)methyl)cyclopentadienyl Ligand Systems" *Organometallics* 16:5449-5456 (1997).

Boswell et al. "Copper-Catalyzed C—N Bond Formation with N-Heterocycles and Aryl Halides" *Synlett* 23:1240-1244 (2012).

Brown et al. "All-Carbon Quaternary Stereogenic Centers by Enantioselective Cu-Catalyzed Conjugate Additions Promoted by a Chiral N-Heterocyclic Carbene" *Angewandte Chemie* 46:1097-1100 (2007).

Cabeza et al. "Cationic Heterocycles as Ligands: Synthesis and Reactivity with Anionic Nucleophiles of Cationic Triruthenium Clusters Containing C-Metalated N-Methylquinoxalinium or N-Methylpyrazinium Ligands" *Chemistry—A European Journal* 15:7339-7349 (2009).

Cabeza et al. "Synthesis and Reactivity of Cationic Triruthenium Clusters Derived from 2-Methyl- and 4-Methylpyrimidines: From Conventional Cyclometalated Ligands to Novel Types of N-Heterocyclic Carbenes" *Chemistry—A European Journal* 19:3426-3436 (2013).

Cariou et al. "A Bidentate NHC-Alkenyl Ruthenium(II) Complex via Vinyl C—H Bond Activation" *Organometallics* 25:2126-2128 (2006).

Cavallo et al. "Steric and electronic effects in the bonding of N-heterocyclic ligands to transition metals" *Journal of Organometallic Chemistry* 690(24-25):5407-5413 (2005) (Abstract Only).

Chang et al. "Highly Efficient N-Heterocyclic Carbene/Pyridine-Based Ruthenium Sensitizers: Complexes for Dye-Sensitized Solar Cells" *Angewandte Chemie* 49:8161-8164 (2010).

Chung et al. "Ruthenium(II) and Osmium(II) Complexes Bearing Bipyridine and the N-Heterocyclic Carbene-Based CNC Pincer Ligand: An Experimental and Density Functional Theory Study" *Inorganic Chemistry* 52:9885-9896 (2013).

Clapham et al. "Mechanisms of the H$_2$-hydrogenation and transfer hydrogenation of polar bonds catalyzed by ruthenium hydride complexes" *Coordination Chemistry Reviews* 248(21-24):2201-2237 (2004) (Abstract Only).

Crabtree, Robert H. "NHC ligands versus cyclopentadienyls and phosphines as spectator ligands in organometallic catalysis" *Journal of Organometallic Chemistry* 690(24-25):5451-5457 (2005) (Abstract Only).

Crabtree, Robert H. "Abnormal, mesoionic and remote N-heterocyclic carbene complexes" *Coordination Chemistry Reviews* 257(3-4):755-766 (2013) (Abstract Only).

Csabai et al. "Synthesis and Catalytic Properties of New Water-Soluble Ruthenium(II)—N-Heterocyclic Carbene Complexes" *Organometallics* 23:5640-5643 (2004).

Danopoulos et al. "Copper and palladium complexes with N-heterocyclic carbene ligands functionalised with carboxylate groups" *Journal of Organometallic Chemistry* 693(21-22):3369-3374 (2008) (Abstract Only).

De Frémont et al. "Synthesis and Structural Characterization of N-Heterocyclic Carbene Gold(I) Complexes" *Organometallics* 24:2411-2418 (2005).

Demir et al. "Synthesis and Catalytic Activity of Novel Benzimidazolinylidene-Ruthenium(II) Complexes" *Synlett* 3:496-500 (2010).

Depasquale et al. "Synthesis of chiral N-heterocyclic carbene (NHC) ligand precursors and formation of ruthenium(II) complexes for transfer hydrogenation catalysts" *Polyhedron* 58:162-170 (2013) (Abstract Only).

Depasquale et al. "Variations on an NHC Theme: Which Features Enhance Catalytic Transfer Hydrogenation with Ruthenium Complexes?" *Organometallics* 32:966-979 (2013).

Dorta et al. "Steric and Electronic Properties of N-Heterocyclic Carbenes (NHC): A Detailed Study on Their Interaction with Ni(CO)$_4$" *Journal of the American Chemical Society* 127:2485-2495 (2005).

Eaborn et al. "Reactions of Methyl Fluorosulphate and Triethyloxonium Tetrafluoroborate with Transition-metal Complexes" *Dalton Transactions* pp. 58-67 (1976).

El-Bahraoui et al. "Theoretical Studies of Ag—Ag Closed-Shell Interaction in the Silver(I) Dimer Bis-µ-(5,7-dimethyl[1,2,4]triazolo[1,5-α]pyrimidine) Dinitrato Disilver(I): A RHF and Density Functional Study" *The Journal of Physical Chemistry A* 102:2443-2448 (1998).

Fekete et al. "Transfer Hydrogenation of Carbonyl Compounds and Alkenes Catalyzed by Ruthenium(II)—N-Heterocycle Carbene Complexes" *Collection of Czechoslovak Chemical Communications* 72(8):1037-1045 (2007).

Fernandez et al. "Ruthenium(II) Picolyl-NHC Complexes: Synthesis, Characterization, and Catalytic Activity in Amine N-alkylation and Transfer Hydrogenation Reactions" *Organometallics* 31:6868-6879 (2012).

Ferreira et al. "Alkylation, Cation Formation, and Insertion Reactions in Titanium Tris(ketimide) Complexes" *Organometallics* 26:119-127 (2007).

Frémont et al. "Synthesis of Well-Defined N-Heterocyclic Carbene Silver(I) Complexes" *Organometallics* 24:6301-6309 (2005).

Fulmer et al. "NMR Chemical Shifts of Trace Impurities: Common Laboratory Solvents, Organics, and Gases in Deuterated Solvents Relevant to the Organometallic Chemist" *Organometallics* 29:2176-2179 (2010).

Gandolfi et al. "Chelating NHC Ruthenium(II) Complexes as Robust Homogeneous Hydrogenation Catalysis" *Organometallics* 28:5112-5121 (2009).

Gao et al. "Magnetically Powered Flexible Metal Nanowire Motors" *Journal of the American Chemical Society* 132:14403-14405 (2010).

(56) References Cited

OTHER PUBLICATIONS

Ghattas et al. "[Ru(bpy)$_3$]$^{2+}$ Analogues Containing an N-Heterocyclic Carbene Ligand" *Organometallics* 29:6782-6789 (2010).

Gimeno et al. "N-Heterocyclic Carbene Coinage Metal Complexes as Intense Blue-Green Emitters" *Organometallics* 31:7146-7157 (2012).

Guo et al. "Palladium, iridium and ruthenium complexes with acyclic imino-N-heterocyclic carbenes and their application in aqua-phase Suzuki-Miyaura cross-coupling reaction and transfer hydrogenation" *Dalton Transactions* 41:14557-14567 (2012).

Guo et al. "binuclear Palladium Complexes of Pyrazole-Bridged Bis(NHC) Ligands: A Delicate Balance between Normal and Abnormal Carbene Coordination" *Organometallics* 33:5145-5155 (2014).

Gürbüz et al. "Preparation of a series of Ru(II) complexes with N-heterocyclic carbene ligands for the catalytic transfer hydrogenation of aromatic ketones" *Dalton Transactions* 41:2330-2339 (2012).

Hackenberg et al. "Novel symmetrically p-benzyl-substituted 4,5-diaryl-imidazole N-heterocyclic carbene-silver(I) acetate complexes—Synthesis and biological evaluation" *Journal of Organometallic Chemistry* 717:123-134 (2012) (Abstract Only).

Hahn et al. "Heterocyclic Carbenes: Synthesis and Coordination Chemistry" *Angewandte Chemie* 47:3122-3172 (2008).

Hair et al. "Insertion and Coordination Reactions of Titanium (IV) Metallocene Zwitterions" *Organometallics* 20:177-181 (2001).

Hanan et al. "Mild and General One-Pot Reduction and Cyclization of Aromatic and Heteroaromatic 2-Nitroamines to Bicyclic 2H-Imidazoles" *Synlett* 18:2759-2764 (2010).

Hashiguchi et al. "Asymmetric Transfer Hydrogenation of Aromatic Ketones Catalyzed by Chiral Ruthenium(II) Complexes" *Journal of the American Chemical Society* 117:7562-7563 (1995).

Herrmann, Wolfgang A. "N-Heterocyclic Carbenes: A New Concept in Organometallic Catalysis" *Angewandte Chemie* 41:1290-1309 (2002).

Hong et al. "Double C—H Activation of an N-Heterocyclic Carbene Ligand in a Ruthenium Olefin Metathesis Catalyst" *Angewandte Chemie* 46:5148-5151 (2007).

Horn et al. "Transfer Hydrogenation of Ketones and Activated Olefins Using Chelating NHC Ruthenium Complexes" *European Journal of Inorganic Chemistry* pp. 2863-2868 (2011).

HTET et al. "Catalytic radical reduction in aqueous solution via oxidation of biologically-relevant alcohols" *Chemical Science* 7 pages (2016).

Huang et al. "Synthesis, structural characterization of benzimidazole-functionalized Ni(II) and Hg(II) N-heterocyclic carbene complexes and their applications as efficient catalysis for Friedel-Crafts alkylations" *Journal of Organometallic Chemistry* 696(18):2949-2957 (2011) (Abstract Only).

Hübner et al. "N,N,O Ligands Based on Triazoles and Transition Metal Complexes Thereof" *European Journal of Inorganic Chemistry* pp. 4100-4109 (2010).

Humenny et al. "N-heterocyclic carbene stabilized copper- and silver-phenylchalcogenolate ring complexes" *Dalton Transactions* 41:4413-4422 (2012).

Janiak, Christoph "A critical account on π-π stacking in metal complexes with aromatic nitrogen-containing ligands" *Journal of the Chemical Society, Dalton Transactions* pp. 3885-3896 (2000).

Jantke et al. "Synthesis and Characterization of Highly Water Soluble Ruthenium(II) and Osmium(II) Complexes Bearing Chelating Sulfonated N-Heterocyclic Carbene Ligands" *Organometallics* 32:741-744 (2013).

Johnson et al. "Reaction Chemistry of the Iron-Sulfur Protein Site Analogues [Fe$_4$S$_4$(SR)$_4$]$_2$-. Sequential Thiolate Ligand Substitution Reactions with Electrophiles" *Journal of the American Chemical Society* 100(17):5338-5344 (1978).

Jung et al. "Site- and Enantioselective Formation of Allene-Bearing Tertiary or Quaternary Carbon Stereogenic Centers through NHC—Cu-Catalyzed Allylic Substitution" *Journal of the American Chemical Society* 134:1490-1493 (2012).

Kayaki et al. "N-Heterocyclic Carbenes as Efficient Organocatalysts for CO$_2$ Fixation Reactions" *Angewandte Chemie* 48:4194-4197 (2009).

Keaton et al. "Base Metal Catalyzed Dehydrogenation of Ammonia—Borane for Chemical Hydrogen Storage" *Journal of the American Chemical Society* 129:1844-1845 (2007).

Lee et al. "Cationic Zirconium Dialkyl and Alkyl Complexes Supported by DAC (Deprotonated 4,13-Diaza-18-crown-6) Ligation" *Organometallics* 16:2556-2561 (1997).

Lee et al. "Density Functional Study of N-Heterocyclic and Diamino Carbene Complexes: Comparison with Phosphines" *Organometallics* 23:976-983 (2004).

Lee et al. "Silver(I) N-Heterocyclic Carbenes with Long N-Alkyl Chains" *Organometallics* 25:3768-3775 (2006).

Lee et al. Stereogenic-at-Metal Zn- and Al-Based N-Heterocyclic Carbene (NHC) Complexes as Bifunctional Catalysis in Cu-Free Enantioselective Allylic Alkylations *Journal of the American Chemical Society* 131:11625-11633 (2009).

Lee et al. "Proton-Sensitive Luminescent Ruthenium(II) Complexes with Pyrazine-Based Pincer-Type N-Heterocyclic Carbene Ligands" *Organometallics* 31:4980-4987 (2012).

Legault et al. "Structure and reactivity of a new anionic N-heterocyclic carbene silver(I) complex" *Chemical Communications* pp. 3826-3828 (2005).

Li et al. "Well-defined N-heterocyclic carbene silver halides of 1-cyclohexyl-3-arylmethylimidazolylidenes: synthesis, structure and catalysis in A$^3$-reaction of aldehydes, amines and alkynes" *Dalton Transactions* 40:2046-2052 (2011).

Li et al. "Synthesis, Structure, and Reactivity of Dicarbene Dipalladium Complexes" *Zeitschrift für Anorganische and Allgemeine Chemie* 639(3-4):575-581 (2013).

Lin et al. "Preparation and application of N-heterocyclic carbene complexes of Ag(I)" *Coordination Chemistry Reviews* 251:642-670 (2007).

Lin et al. "Carboxylic acid functionalized imidazolium salts: sequential formation of ionic, zwitterionic, acid-zwitterionic and lithium salt-zwitterionic liquid crystals" *Journal of Materials Chemistry* 21:8110-8121 (2011).

Liu et al. "New N-heterocyclic carbene silver(I) and mercury(II) 2-D supramolecular layers by the π-π stacking interactions" *Journal of Organometallic Chemistry* 692(17):3655-3663 (2007) (Abstract Only).

Liu et al. "New N-heterocyclic carbene mercury(II) and silver(I) complexes" *Polyhedron* 27(1):87-94 (2008) (Abstract Only).

Liu et al. "Two new N-heterocyclic carbene silver(I) complexes with the π-π stacking interactions" *Inorganica Chimica Acta* 361(9-10):2616-2622 (2008) (Abstract Only).

Liu et al. "Macrocyclic Dinuclear silver(I) complexes based on bis(N-heterocyclic carbene) ligands: synthesis and structural studies" *CrystEngComm* 12:2245-2255 (2010).

Liu et al. "Tetranuclear N-Heterocyclic Carbene Mercury(II) Complexes Containing Triply Deprotonated Acetonitrile: Synthesis and Structural Studies" *European Journal of Inorganic Chemistry* pp. 983-988 (2010).

Liu et al. "Metal N-heterocyclic carbene complexes as potential antitumor metallodrugs" *Chemical Society Reviews* 42:755-773 (2013).

Lohre et al. "Nickel-Catalyzed Cross-Coupling of Aryl Bromides with Tertiary Grignard Reagents Utilizing Donor-Functionalized N-Heterocyclic Carbenes (NHCs)" *Chemistry—A European Journal* 17:6052-6055 (2011).

Luca et al. "Redox-active cyclopentadienyl Ni complexes with quinoid N-heterocyclic carbene ligands for the electrocatalytic hydrogen release from chemical fuels" *New Journal of Chemistry* 37:3402-3405 (2013).

Ma et al. "Effect of carboxyl-functionalized imidazolium salts on the rhodium-catalyzed hydrosilylation of alkene" *Journal of Organometallic Chemistry* 727:28-36 (2013) (Abstract Only).

Mangalum et al. "Net charge effects in N-heterocyclic carbene-ruthenium complexes with similar oxidation states and coordination geometries" *Inorganica Chimica Acta* 435:320-326 (2015).

(56) References Cited

OTHER PUBLICATIONS

Mangalum et al. "Synthesis, coordination chemistry and reactivity of transition metal complexes supported by a chelating benzimidazolylidene carboxylate ligand" *Inorganica Chimica Acta* 426:29-38 (2015).
Mankad et al. "Synthesis, Structure, and $CO_2$ Reactivity of a Two-Coordinate (Carbene)copper(I) Methyl Complex" *Organometallics* 23:1191-1193 (2004).
Marchetti et al. "Switching between $K^2$ and $K^3$ Bis(pyrazol-1-yl)acetate Ligands by Tuning Reacting Conditions: Synthesis, Spectral, Electrochemical, Structural, and Theoretical Studies on Arene-Ru(II) Derivatives of Bis(azol-1-yl) acetate Ligands" *Inorganic Chemistry* 48(13):6096-6108 (2009) (Abstract Only).
Meng et al. "Exceptionally E- and β-Selective NHC—Cu-Catalyzed Proto-Silyl Additions to Terminal Alkynes and Site- and Enantioselective Proto-Boryl Additions to the Resulting Vinylsilanes: Synthesis of Enantiomerically Enriched Vicinal and Geminal Borosilanes" *Chemistry—A European Journal* 19:3204-3214 (2013).
Monney et al. "Synthesis and catalytic activity of histidine-based NHC ruthenium complexes" *Dalton Transactions* 40:2716-2719 (2011).
Moore et al. "Synthesis and Characterization of Water-Soluble Silver and Palladium Imidazol-2-ylidene Complexes with Noncoordinating Anionic Substituents" *Organometallics* 25(21):5151-5158 (2006) (Abstract Only).
Müller et al. "Ruthenium(II) Complexes Bearing Carboxylato and 2-Oxocarboxylato Ligands" *European Journal of Inorganic Chemistry* pp. 2151-2159 (2004).
Nagai et al. "Synthesis of N-Heterocyclic Carbene-Sulfonate Palladium Complexes" *Organometallics* 28(20):6131-6134 (2009) (Abstract Only).
Nockemann et al. "Carboxyl-functionalized task-specific ionic liquids for solubilizing metal oxides" *Inorganic Chemistry* 47(21):9987-9999 (2008) (Abstract Only).
Norris et al. "Synthesis of phosphonic acid derivatized bipyridine ligands and their ruthenium complexes" *Inorganic Chemistry* 52(21):12495-12501 (2013) (Abstract Only).
O et al. "Mechanistic Investigation of the Hydrogenation of Ketones Catalyzed by a Ruthenium(II) Complex Featuring an N-Heterocyclic Carbene with a Tethered Primary Amine Donor: Evidence for an Inner Sphere Mechanism" *Organometallics* 30(5):1236-1252 (2011) (Abstract Only).
Oh et al. "Synthesis and structures of N,N,O-scorpionatoruthenium(II) complexes featuring "non-innocent" o-benzoquinonediimines" *Polyhedron* 29(8):1964-1967 (2010) (Abstract Only).
Ohara et al. "Effect of chelating ring size in catalytic ketone hydrogenation: facile synthesis of ruthenium(II) precatalysts containing an N-heterocyclic carbene with a primary amine donor for ketone hydrogenation and a DFT study of mechanisms" *Dalton Transactions* 41:8797-8808 (2012).
Park et al. "Unsymmetric Ru(II) Complexes with N-Heterocyclic Carbene and/or Terpyridine Ligands: Synthesis, Characterization, Ground- and Excited-State Electronic Structures and Their Application for DSSC Sensitizers" *Inorganic Chemistry* 49:7340-7352 (2010).
Patil et al. "Synthesis, cytotoxicity and antibacterial studies of symmetrically and non-symmetrically benzyl- or p-cyanobenzyl-substituted N-Heterocyclic carbene—silver complexes" *Applied Organometallic Chemistry* 24:781-793 (2010).
Patil et al. "Synthesis, Cytotoxicity and Antibacterial Studies of p-Methoxybenzyl-Substituted and Benzyl-Substituted N-Heterocyclic Carbene—Silver Complexes" *European Journal of Inorganic Chemistry* pp. 1020-1031 (2010).
Patil et al. "Synthesis, Cytotoxicity and Antibacterial Studies of Novel Symmetrically and Nonsymmetrically 4-(Methoxycarbonyl)benzyl-Substituted N-Heterocyclic Carbene—Silver Acetate Complexes" *Helvetica Chimica Acta* 93:2347-2364 (2010).
Patil et al. "Novel benzyl-substituted N-heterocyclic carbene—silver acetate complexes: synthesis, cytotoxicity and antibacterial studies" *Metallomics* 3:74-88 (2011).
Patil et al. "Synthesis, Cytotoxicity and Antibacterial Studies of Novel Symmetrically and Nonsymmetrically p-Nitrobenzyl-Substituted N-Heterocyclic Carbene—Silver(I) Acetate Complexes" *Zeitschrift für Anorganische und Allgemeine Chemie* 637:386-396 (2011).
Peris et al. "Recent homogeneous catalytic applications of chelate and pincer N-heterocyclic carbenes" *Coordination Chemistry Reviews* 248(21-24):2239-2246 (2004) (Abstract Only).
Plummer et al. "Synthesis and characterization of homoleptic complexes of the chelating Bidentate isocyano ligand tert-BuDiNC" *Inorganic Chemistry* 22(26):4063-4070 (1983) (Abstract Only).
Poater et al. "Rationalizing current strategies to protect N-heterocyclic carbene-based ruthenium catalysis active in olefin metathesis from C—H (de)activation" *ChemComm* 47:6674-6676 (2011).
Pyykkö, Pekka "Strong Closed-Shell Interactions in Inorganic Chemistry" *Chemical Reviews* 97(3):597-636 (1997) (Abstract Only).
Ray et al. "Shorter argentophilic interaction than aurophilic interaction in a pair of dimeric{(NHC)MCl}(2) (M=Ag, Au) complexes supported over a N/O-functionalized N-heterocyclic carbene (NHC) ligand" *Inorganic Chemistry* 47(1):230-240 (2008) (Abstract Only).
Russell et al. "Tetramethylthiophen Complexes of Rhodium, Iridium, Palladium, and Ruthenium" *Journal of the Chemical Society, Dalton Transactions* 7:857-861 (1978).
Sheldrick, George M. "A short history of SHELX" *Acta Crystallographica Section A* A64:112-122 (2008).
Simal et al. "Evaluation of ruthenium-based complexes for the controlled radical polymerization of vinyl monomers" *Canadian Journal of Chemistry* 79:529-535 (2001).
Simpson et al. "Synthesis, Cellular Uptake and Biological Activity Against Pathogenic Microorganisms and Cancer Cells of Rhodium and Iridium N-Heterocyclic Carbene Complexes Bearing Charged Substituents" *European Journal of Inorganic Chemistry* 2013(32):5547-5554 (2013).
Singh et al. "Ligand-Unsupported Metal-Metal (M=Cu, Ag) Interactions between Closed-Shell $d^{10}$ Trinuclear Systems" *Journal of the American Chemical Society* 119:2942-2943 (1997).
Sinn et al. "Physicochemical analysis of ruthenium(II) sensitizers of 1,2,3-triazole-derived mesoionic carbene and cyclometalating ligands" *Inorganic Chemistry* 53(4):2083-2095 (2014) (Abstract Only).
Sivakumar et al. "Synthesis and Characterization of New Dicationic Dihydrogen Complexes of Ruthenium" *Synthesis and Reactivity in Inorganic, Metal-Organic, and Nano-Metal Chemistry* 37:677-684 (2007).
Songis et al. "[Pd(NHC)(PR$_3$)] Complexes: Versatile Tools for Tandem Dehydrogenation-Hydrogenation Processes" *Synlett* 24:1877-1881 (2013).
Spek, Anthony L. "Structure validation in chemical crystallography" *Acta Crystallographica Section D* D65:148-155 (2009).
Štěpnička, Petr "Synthesis, characterization and diastereoselective coordination of a planarly chiral, hybrid ferrocene ligand, $(S_p)$-2-(diphenylphosphino)ferrocenecarboxylic acid" *New Journal of Chemistry* 26:567-575 (2002).
Suzuki et al. "Ruthenium(II) Complexes Containing 8-(Dimethylphosphino)quinoline (Me$_2$Pqn): Preparation, Crystal Structures, and Electrochemical and Spectroscopic Properties of [Ru(bpy or phen)$_{3-n}$(Me$_2$Pqn)$_n$](PF$_6$)$_2$ (bpy =2,2'-Bipyridine; phen =1,10-Phenanthroline; n =1, 2, or 3)" *Inorganic Chemistry* 42(3):785-795 (2003) (Abstract Only).
Tampier et al. "Synthesis, structure, and reactivity of ruthenium carboxylato and 2-oxocarboxylato complexes bearing the bis(3,5-dimethylpyrazol-1-yl) acetato ligand" *Inorganic Chemistry* 47(20):9624-9641 (2008) (Abstract Only).
Temme et al. "Heterodimetal—Betaine Chemistry: Catalytic and Stoichiometric Coupling of Alkynyl Ligands under the Joint Influence of Zirconium and Boron Centers" *Angewandte Chemie* 33(14):1480-1482 (1994).
Teyssot et al. "Metal-NHC complexes: a survey of anti-cancer properties" *Dalton Transactions* 35:6894-6902 (2009).

(56) References Cited

OTHER PUBLICATIONS

Tomson et al. "Synthesis and reactivity of cationic niobium and tantalum methyl complexes supported by imido and 62-diketiminato ligands" *Dalton Transactions* 40:7718-7729 (2011).

Treichel et al. "Facile halide replacement in electron rich complexes" *Journal of Organometallic Chemistry* 122(2):229-240 (1976) (Abstract Only).

Türkoglu et al. "Bis(3,5-dimethyl-4-vinylpyrazol-1-yl)acetic Acid: A New Heteroscorpionate Building Block for Copolymers that Mimic the 2-His-1-carboxylate Facial Triad" *European Journal of Inorganic Chemistry* 2010(19):2962-2974 (2010) (Abstract Only).

Türkoglu et al. "Transition metal complexes bearing a 2,2-bis(3,5-dimethylpyrazol-1-yl) propionate ligand: one methyl more matters" *Dalton Transactions* 40(17):4678-4686 (2011) (Abstract Only).

Türkoglu et al. "Ruthenium Carbonyl Complexes Bearing Bis(pyrazol-1-yl)carboxylato Ligands" *Organometallics* 31(6):2166-2174 (2012) (Abstract Only).

Visbal et al. "N-heterocyclic carbene metal complexes: photoluminescence and applications" *Chemical Society Reviews* 43:3551-3574 (2014).

Wang et al. "Preparation and Structure of Mono- and Binuclear Half-Sandwich Iridium, Ruthenium, and Rhodium Carbene Complexes Containing 1,2-Dichalcogenolao 1,2-Dicarba-closo-Dodecaboranes" *Chemistry—A European Journal* 13:188-195 (2007).

Wanzlick et al. "Direct Synthesis of a Mercury Salt-Carbene Complex[1]" *Angewandte Chemie* 7(2):141-142 (1968).

Würtemberger et al. "Synthesis and Characterization of Tetrakis(carbene)ruthenium(II) Complexes Featuring an [Ru(NHC)$_4$]$^{2+}$ Core" *European Journal of Inorganic Chemistry* 2011(3):405-415 (2011).

Xuan et al. "Synthesis, crystal structure, vibrational spectra and theoretical calculation of 1-carboxymethyl-3-methylimidazolium chloride" *Spectrochimica Acta Part A: Molecular and Biomolecular Spectroscopy* 96:436-443 (2012) (Abstract Only).

Yan et al. "Ancillary Ligand Effects upon Dithiolene Redox Noninnocence in Tungsten Bis(dithiolene) Complexes" *Inorganic Chemistry* 52:6743-6751 (2013).

Yoshimura et al. "Synthesis of Ru(II) complexes containing N-heterocyclic carbenes functionalized with secondary donor groups: Catalytic activity toward enantioselective transfer hydrogenation" *Journal of Organometallic Chemistry* 740:26-32 (2013) (Abstract Only).

Zhang et al. "The intramolecular sp$^2$ and sp$^3$ C—H bond activation of (p-cymene)ruthenium(II) N-heterocyclic carbene complexes" *Dalton Transactions* 26:5182-5189 (2009).

Zhang et al. "Well-Defined N-Heterocyclic Carbene Based Ruthenium Catalysts for Direct Amide Synthesis from Alcohols and Amines" *Organometallics* 29(6):1374-1378 (2010) (Abstract Only).

Zhou et al. "CO$_2$ Adducts of N-Heterocyclic Carbenes: Thermal Stability and Catalytic Activity toward the Coupling of CO$_2$ with Epoxides" *The Journal of Organic Chemistry* 73(20):8039-8044 (2008) (Abstract Only).

Zhou et al. "Synthesis, cis/trans Isomerization, and Reactivity of Palladium Alkyl Complexes That Contain a Chelating N-Heterocyclic-Carbene Sulfonate Ligand" *Organometallics* 30(17):4632-4642 (2011) (Abstract Only).

Zimmerman et al. "The Role of Free N-Heterocyclic Carbene (NHC) in the Catalytic Dehydrogenation of Ammonia-Borane in the Nickel NHC System" *Angewandte Chemie International Edition* 48:2201-2205 (2009).

Ia: R = Mes, X = Cl
Ib: R = Dipp, X = Br

IIa: R = Mes, Z = CO$_2$, n = 2
IIb: R = Dipp, Z = SO$_3$, n = 3

IIIa: R$^1$ = Mes, R$^2$ = H
IIIb: R$^1$ = Et, R$^2$ = iPr

IIIc

IIId

IIIe

IIIf

SELF-REGENERATING ANTIOXIDANT CATALYSTS AND METHODS OF USING THE SAME

RELATED APPLICATION DATA

This application claims the benefit of U.S. Provisional Patent Application Ser. No. 62/085,862, filed Dec. 1, 2014, the disclosure of which is incorporated herein by reference in its entirety.

FIELD OF THE INVENTION

The present invention relates to self-regenerating antioxidant catalysts and methods of using the same.

BACKGROUND OF THE INVENTION

Artificial implant materials (AIMs) in contact with biological tissues induce the formation of reactive oxygen species (ROS), which then trigger an aseptic immune response (termed the foreign body reaction, FBR) that causes chemical and mechanical degradation of AIMs. Judicious selection of AIM type does not prevent this outcome, as even robust materials such as stainless steel and fluoropolymer plastics are attacked by corrosion and mechanical stress/strain forces. Immunosuppressive drugs protect AIMs against degradation by preventing the onset of FBR, but also impede essential healing processes and increase the risk of infection. Incorporating traditional organic antioxidants into AIMs enables them to halt or reduce ROS buildup and thus prevent FBR onset, but the prolonged nature of oxidative stress and the irreversible reactivity of traditional antioxidants with ROS eventually depletes the protective capacity.

SUMMARY OF THE INVENTION

A first aspect of the invention is a compound represented by one of the following structures:

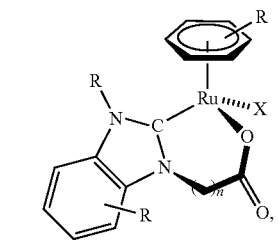

Ru1

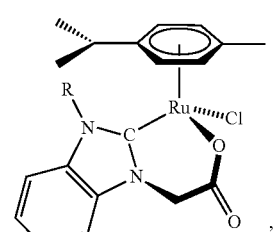

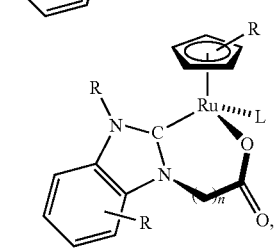

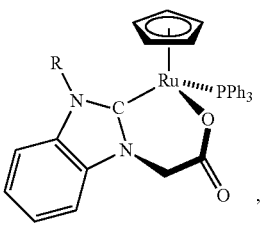

Ru2

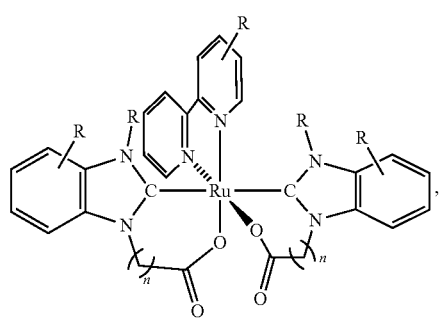

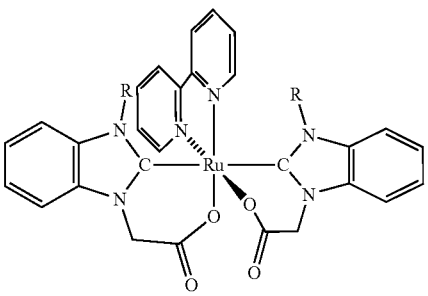

Ru3

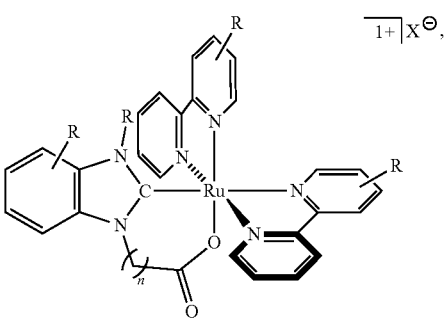

Ru4

Ru5

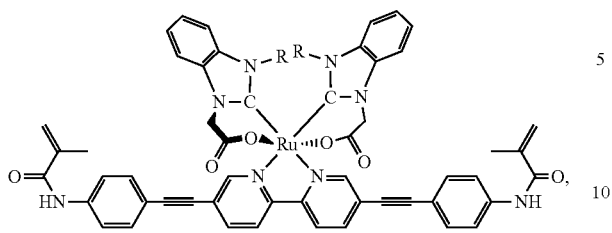

Ru6

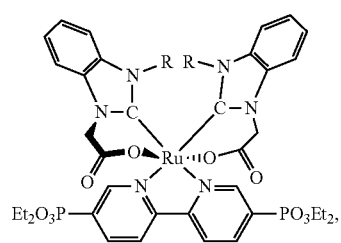

Ru7

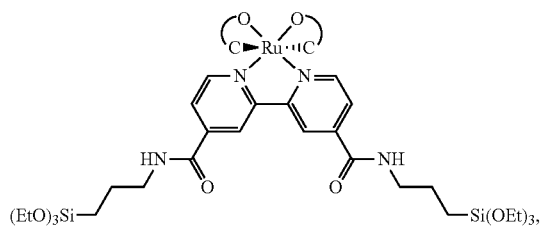

Ru9

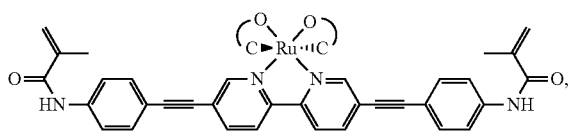

Ru10

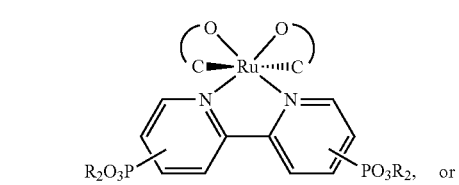

Ru-PPE

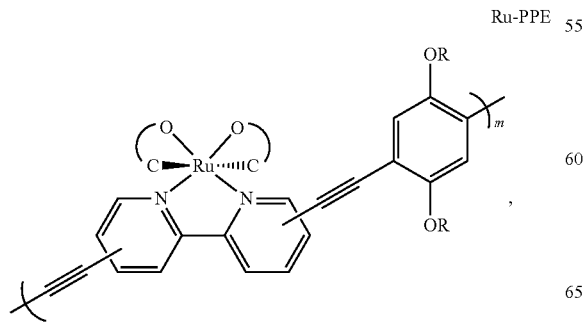

wherein 
$\begin{pmatrix} O \\ C \\ C \end{pmatrix}$
is
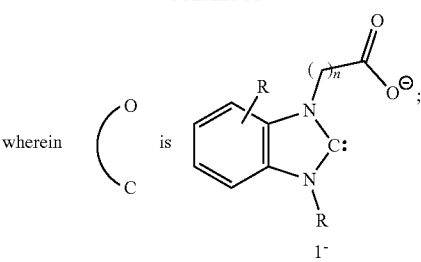

wherein each R is independently a hydrogen, substituted or unsubstituted alkyl group, or a substituted or unsubstituted aryl group, wherein the substituted alkyl group or the substituted aryl group are substituted with a substituent selected from the group consisting of an alkyl group, alkenyl group, alkynyl group, halogen atom, carbonyl-containing functional group, aryl group, heterocyle, alcohol, thiol, amine, ether, thioether, azide, and any combination thereof;

X is a non-coordinating anion;

n is an integer from 1 to 30; and m is an integer from 1 to 30;

and/or a derivative thereof.

A further aspect of the invention is a biomedical implant material comprising a compound and/or self-regenerating antioxidant catalyst of the present invention, wherein the compound is present on at least a portion of a surface of the biomedical implant material.

Another aspect of the invention is method of decreasing and/or preventing damage to a biomedical implant material, the method comprising providing the biomedical implant material, the biomedical implant material comprising a self-regenerating antioxidant catalyst of the present invention on at least a portion of a surface of the biomedical implant material, thereby decreasing and/or preventing damage to the biomedical implant material.

Another aspect of the invention is a compound represented by one of the following structures:

[1H$_2$][X]

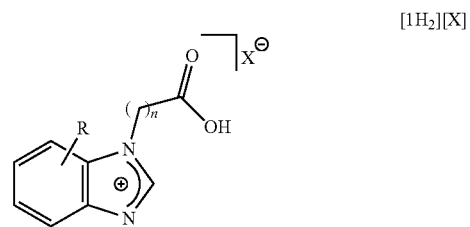

[1H]

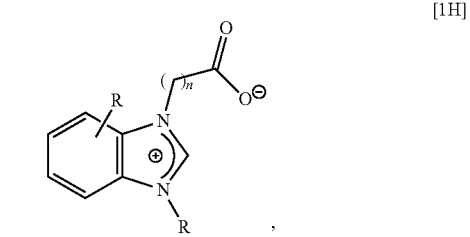

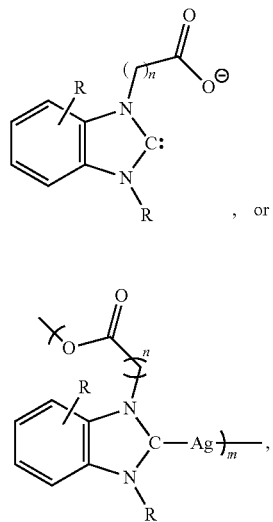

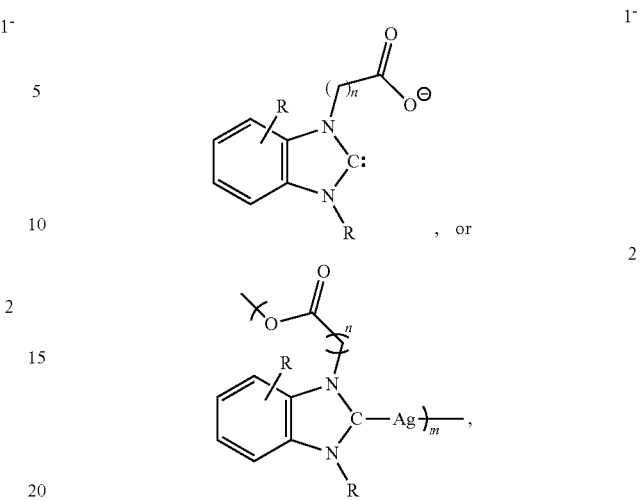

wherein each R independently is a hydrogen, substituted or unsubstituted alkyl group, or a substituted or unsubstituted aryl group, wherein the substituted alkyl group or the substituted aryl group are substituted with a substituent selected from the group consisting of an alkyl group, alkenyl group, alkynyl group, halogen atom, carbonyl-containing functional group, aryl group, heterocyle, alcohol, thiol, amine, ether, thioether, azide, and any combination thereof. In some embodiments, R is hydrogen. In some embodiments, R is a substituted aryl group. In some embodiments, R is 3,5-dimethylphenyl or 4-methylphenyl.

A further aspect of the invention is a method of preparing a self-regenerating antioxidant catalyst of the present invention. In some embodiments, the method comprises preparing the self-regenerating antioxidant catalyst from a compound represented by one of the following structures:

[1H₂][X]

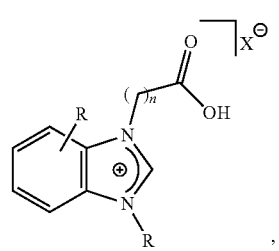

[1H]

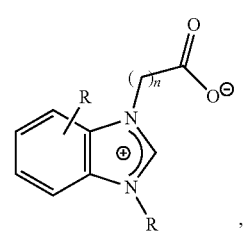

wherein each R independently is a hydrogen, substituted or unsubstituted alkyl group, or a substituted or unsubstituted aryl group, wherein the substituted alkyl group or the substituted aryl group are substituted with a substituent selected from the group consisting of an alkyl group, alkenyl group, alkynyl group, halogen atom, carbonyl-containing functional group, aryl group, heterocyle, alcohol, thiol, amine, ether, thioether, azide, and any combination thereof.

DETAILED DESCRIPTION

Figure 1:
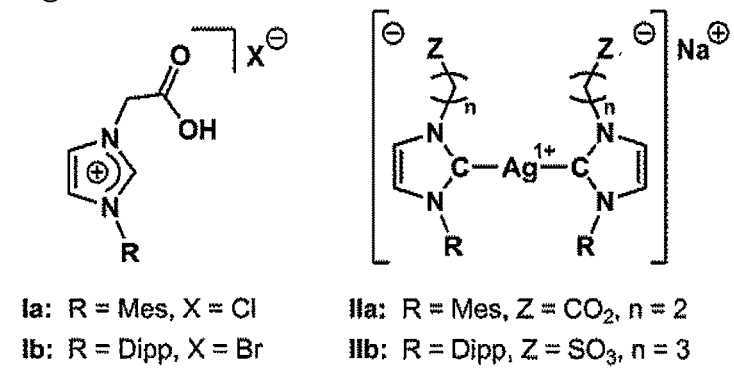
FIG. 1 shows compounds analogous to [1H₂][Br], 2 and Ru1 previously reported in the literature. Mes=2,4,6-trimethylphenyl; Dipp=2,6-diisopropylphenyl.
Figure 1:
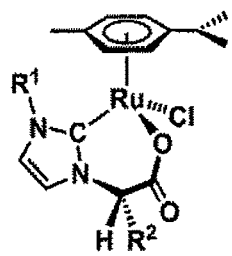

The present invention will now be described more fully hereinafter. This invention may be embodied in different forms and should not be construed as limited to the embodiments set forth herein. Rather, these embodiments are provided so that this disclosure will be thorough and complete, and will fully convey the scope of the invention to those skilled in the art.

The terminology used in the description herein is for the purpose of describing particular embodiments only and is not intended to be limiting of the invention. As used in the description and the appended claims, the singular forms "a", "an" and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description herein is for the purpose of describing particular embodiments only and is not intended to be limiting of the invention.

All patents, patent applications and publications referred to herein are incorporated by reference in their entirety. In case of a conflict in terminology, the present specification is controlling.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the embodiments of the invention described herein may be used in any combination. For example, features described in relation to one embodiment may also be applicable to and combinable with other embodiments and aspects of the invention.

Moreover, the embodiments of the present invention also contemplate that in some embodiments, any feature or combination of features set forth herein may be excluded or omitted. To illustrate, if the specification states that a complex comprises components A, B and C, in some embodiments, any of A, B or C, or a combination thereof, may be omitted and disclaimed.

As used herein, the transitional phrase "consisting essentially of" (and grammatical variants) is to be interpreted as encompassing the recited materials or steps "and those that do not materially affect the basic and novel characteristic(s)" of the claimed invention. See, *In re Herz*, 537 F.2d 549, 551-52, 190 U.S.P.Q. 461, 463 (CCPA 1976) (emphasis in the original); see also MPEP §2111.03. Thus, the term "consisting essentially of" as used herein should not be interpreted as equivalent to "comprising."

The term "about," as used herein when referring to a measurable value such as an amount or concentration (e.g., the amount of a self-regenerating antioxidant catalyst) and the like, is meant to encompass variations of ±10%, ±5%, ±1%, ±0.5%, or even ±0.1% of the specified amount.

"Substituted" as used herein to describe chemical structures, groups, or moieties, refers to the structure, group, or moiety comprising one or more substituents. As used herein, in cases in which a first group is "substituted with" a second group, the second group is attached to the first group whereby a moiety of the first group (typically a hydrogen) is replaced by the second group. The substituted group may contain one or more substituents that may be the same or different.

"Substituent" as used herein references a group that replaces another group in a chemical structure. Typical substituents include nonhydrogen atoms (e.g., halogens), functional groups (such as, but not limited to, amino, sulfhydryl, carbonyl, hydroxyl, alkoxy, carboxyl, silyl, silyloxy, phosphate and the like), hydrocarbyl groups, and hydrocarbyl groups substituted with one or more heteroatoms. Exemplary substituents include, but are not limited to, alkyl, lower alkyl, halo, haloalkyl, alkenyl, alkynyl, cycloalkyl, cycloalkylalkyl, heterocyclo, heterocycloalkyl, aryl, arylalkyl, lower alkoxy, thioalkyl, hydroxyl, thio, mercapto, amino, imino, halo, cyano, nitro, nitroso, azido, carboxy, sulfide, sulfone, sulfoxy, phosphoryl, silyl, silylalkyl, silyloxy, boronyl, and modified lower alkyl.

"Alkyl" as used herein alone or as part of another group, refers to a straight (i.e., unbranched), branched, or cyclic hydrocarbon chain containing from 1 to 30 carbon atoms that is completely saturated. In some embodiments, the alkyl group may contain 1, 2, or 3 up to 4, 5, 6, 7, 8, 9, 10, 11, 12, 13, 14, 15, 16, 17, 18, 19, 20, 21, 22, 23, 24, 25, 26, 27, 28, 29, or 30 carbon atoms. In some embodiments, the term "alkyl" or "alkyl group" refers to a cycloalkyl group, also known as carbocycle. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, cyclopropyl, cyclohexyl and the like. "Lower alkyl" as used herein, is a subset of alkyl and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like. The term "alkyl" or "loweralkyl" is intended to include both substituted and unsubstituted alkyl or loweralkyl unless otherwise indicated and these groups may be substituted with groups such as, but not limited to, polyalkylene oxides (such as PEG), halo (e.g., haloalkyl), alkyl, haloalkyl, alkenyl, alkynyl, cycloalkyl, cycloalkylalkyl, aryl, arylalkyl, heterocyclo, heterocycloalkyl, hydroxyl, alkoxy (thereby creating a polyalkoxy such as polyethylene glycol), alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstitutedamino, acylamino, acyloxy, ester, amide, sulfonamide, urea, alkoxyacylamino, aminoacyloxy, nitro or cyano, where m=0, 1, 2 or 3.

"Alkenyl" as used herein alone or as part of another group, refers to a straight (i.e., unbranched), branched, or cyclic hydrocarbon chain containing from 1 to 30 carbon atoms (or in loweralkenyl 1 to 4 carbon atoms) and has one or more double bonds (e.g., 1 to 10 double bonds in the hydrocarbon chain). In some embodiments, the alkenyl group may contain 1, 2, or 3 up to 4, 5, 6, 7, 8, 9, 10, 11, 12, 13, 14, 15, 16, 17, 18, 19, 20, 21, 22, 23, 24, 25, 26, 27, 28, 29, or 30 carbon atoms. According to another aspect, the term alkenyl refers to a straight chain hydrocarbon having two double bonds, also referred to as "diene." In some embodiments, the term "alkenyl" or "alkenyl group" refers to a cycloalkenyl group. Representative examples of alkenyl include, but are not limited to, methylene (=CH$_2$), vinyl (—CH=CH$_2$), allyl (—CH$_2$CH=CH$_2$), 2-butenyl, 3-butenyl, 4-pentenyl, 3-pentenyl, 2-hexenyl, 3-hexenyl, 2,4-heptadiene, cyclobutenyl, and the like. The term "alkenyl" or "loweralkenyl" is intended to include both substituted and unsubstituted alkenyl or loweralkenyl unless otherwise indicated and these groups may be substituted with groups such as those described in connection with alkyl and loweralkyl above.

"Alkynyl" as used herein alone or as part of another group, refers to a straight or branched chain hydrocarbon containing from 1 to 30 carbon atoms (or in loweralkynyl 1 to 4 carbon atoms) which include at least one triple bond in the hydrocarbon chain. In some embodiments, the alkynyl group may contain 2, or 3 up to 4, 5, 6, 7, 8, 9, 10, 11, 12, 13, 14, 15, 16, 17, 18, 19, 20, 21, 22, 23, 24, 25, 26, 27, 28, 29, or 30 carbon atoms. Representative examples of alkynyl include, but are not limited to, 2-propynyl, 3-butynyl, 2-butynyl, 4-pentynyl, 3-pentynyl, and the like. The term "alkynyl" or "loweralkynyl" is intended to include both substituted and unsubstituted alkynyl or loweralkynyl unless otherwise indicated and these groups may be substituted with the same groups as set forth in connection with alkyl and loweralkyl above.

"Aryl" as used herein alone or as part of another group, refers to a monocyclic carbocyclic ring system or a bicyclic carbocyclic fused ring system or higher having one or more aromatic rings. Representative examples of aryl include, azulenyl, indanyl, indenyl, naphthyl, phenyl, tetrahydronaphthyl, and the like. The term "aryl" is intended to include both substituted and unsubstituted aryl unless otherwise indicated and these groups may be substituted with the same groups as set forth in connection with alkyl and loweralkyl above.

"Arylalkyl" as used herein alone or as part of another group, refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-ylethyl, and the like.

"Heterocycle" refers to a cyclic moiety having one or more closed rings with one or more heteroatoms (for example, oxygen, nitrogen or sulfur) in at least one of the rings, wherein the ring or rings may independently be fused, and/or bridged. In some embodiments, a heterocycle may be a heteroaryl. "Heteroaryl" refers to a cyclic moiety having one or more closed rings with one or more heteroatoms (for example, oxygen, nitrogen or sulfur) in at least one of the rings, wherein at least one of the rings is aromatic, and wherein the ring or rings may independently be fused, and/or bridged. Examples include without limitation phenyl, thiophenyl, triazolyl, pyridinyl, pyrimidinyl, pyridazinyl, pyrazinyl, quinolinyl, isoquinolinyl, indolyl, furyl, thienyl, pyrazolyl, quinoxalinyl, pyrrolyl, indazolyl, thieno[2,3-c]pyrazolyl, benzofuryl, pyrazolo[1,5-a]pyridyl, thiophenylpyrazolyl, benzothienyl, benzothiazolyl, thiazolyl, 2-phenylthiazolyl, and isoxazolyl.

"Halogen" or "halo" as used herein refer to fluoro, chloro, bromo or iodo.

An "amine" as used herein refers to an organic compound having a basic nitrogen atom (R—NR'R"), and may be a primary (R—NH$_2$), secondary (R—NHR') or tertiary (R—NR'R") amine.

The term "carbonyl" refers to a —(C=O)— group.

The term "azide" refers to a —N$_3$ group.

Provided according to embodiments of the present invention are self-regenerating antioxidant catalysts. "Self-regenerating" as used herein refers to a self-regenerating antioxidant catalyst's ability to be regenerated as an integral consequence of performing a reaction (e.g., without requiring a subsequent reaction in order to regenerate), such as, e.g., a degradation reaction, and used in a subsequent reaction (e.g., a degradation reaction). Thus, "self-regenerating" as used herein refers to the ability of a self-regenerating antioxidant catalyst to return to a state in which it can be reused in another reaction.

In some embodiments, the self-regenerating antioxidant catalyst may be stable in that a metal present in the self-regenerating antioxidant catalyst is not removed in the presence of a chelating molecule that may cause demetallation (e.g., such as ones that may be present in a biological system in which the self-regenerating antioxidant catalyst is present). The self-regenerating antioxidant catalyst may be stable and thus retain its activity. In some embodiments, the self-regenerating antioxidant catalyst may retain at least 50%, 55%, 60%, 65%, 70%, 75%, 80%, 85%, 90%, 95%, or 100% of its activity after at least 1, 2, 3, 4, 5, or 6 day(s), or 1, 2, 3, or 4 week(s), or 1, 2, 3, 4, 5, 6, 7, 8, 9, 10, 11, 12 or more month(s).

A self-regenerating antioxidant catalyst of the present invention may degrade, such as, for example, reduce, a radical catalytically. The radical may be an oxidizing radical (e.g., a compound that includes an unpaired electron). In some embodiments, the self-regenerating antioxidant catalyst reduces oxidizing radicals catalytically. In some embodiments, the self-regenerating antioxidant catalyst may be regenerated after a radical degradation reaction.

A self-regenerating antioxidant catalyst of the present invention may degrade (e.g., reduce) reactive oxygen species (ROS). "Reactive oxygen species" or "ROS" as used herein refer to oxygen containing compounds that can cause oxidation of another molecule. In some embodiments, a ROS may trigger an aseptic immune response and/or a foreign body reaction (FBR). "Oxidizing radicals" as used herein refer to compounds with unpaired electrons that can cause oxidation of another molecule. Although there is overlap between ROS and oxidizing radicals, the former may not necessarily contain unpaired electrons (e.g., $ONOO^-$) and the latter may not necessarily contain oxygen (e.g., thiyl radicals). In some embodiments, the self-regenerating antioxidant catalyst may catalytically degrade a ROS and/or radical under physiologically relevant conditions, such as, for example, at physiological pH, a pH in a range of about 6 to about 8, and/or when in contact with a biological subject (e.g., when in, on, and/or in contact with a biological tissue and/or fluid)

In some embodiments, a self-regenerating antioxidant catalyst of the present invention may catalytically degrade a ROS and/or radical and after one or more degradation reaction(s) the self-regenerating antioxidant catalyst may be regenerated. In some embodiments, the self-regenerating antioxidant catalyst may be regenerated 2, 5, 10, 20, 30, 40, 50, 60, 70, 80, 90, 100, 150, 200, 250, 300, or more times. Some embodiments include that the self-regenerating antioxidant catalyst may be regenerated after 1, 2, 5, 10, 20, 30, 40, 50, 60, 70, 80, 90, 100, 150, 200, or more degradation reaction(s) (e.g., after 1 or more reaction(s) in which the self-regenerating antioxidant catalytically degrades a radical and/or ROS). In some embodiments, the self-regenerating antioxidant catalyst may provide at least tens or hundreds of turnovers or regeneratiions of the self-regenerating antioxidant catalyst compared to a stoichiometric antioxidant reaction. The self-regenerating antioxidant catalyst may provide greater protection against radicals and/or ROS to a material (e.g., an artificial implant material) in which the self-regenerating antioxidant catalyst is present on, in, and/or adjacent to. The self-regenerating antioxidant catalyst may catalytically degrade a ROS and/or radical under aerobic conditions and/or under conditions in which oxygen may or may not be present.

In some embodiments, a self-regenerating antioxidant catalyst of the present invention may slow the formation of a ROS and/or radical. The self-regenerating antioxidant catalyst may slow the formation of a ROS and/or radical under aerobic conditions and/or under conditions in which oxygen may or may not be present. The self-regenerating antioxidant catalyst may slow the formation of the ROS and/or radical under physiologically relevant conditions. In some embodiments, a self-regenerating antioxidant catalyst of the present invention may catalyze the degradation and/or slow the formation of radicals and/or ROS in aqueous buffer at physiologically-relevant pH (e.g., at a pH in a range of about 6 to about 8, about 7 to about 8, or at a pH of about 7.4). Some embodiments include that a self-regenerating antioxidant catalyst of the present invention may reduce or slow the formation of a radical and/or ROS by at least 10%, 20%, 30%, 40%, 50%, 60%, 70%, 80%, 90%, 100%, 150%, 200%, or more compared to the rate of formation of radicals and/or ROS in the absence of the self-regenerating antioxidant catalyst.

In some embodiments, a self-regenerating antioxidant catalyst of the present invention may reduce and/or prevent material damage by a ROS and/or radical. The self-regenerating antioxidant catalyst may reduce and/or prevent material damage by the ROS and/or radical under physiologically relevant conditions. The self-regenerating antioxidant catalyst may reduce and/or prevent material damage by the ROS and/or radical under aerobic conditions and/or under conditions in which oxygen may or may not be present. In some embodiments, a self-regenerating antioxidant catalyst of the present invention may reduce and/or prevent material damage by radicals and/or ROS in aqueous buffer, which may be at a physiologically-relevant pH. Some embodiments include that a self-regenerating antioxidant catalyst of the present invention may reduce and/or prevent material damage by a ROS and/or radical by at least 10%, 20%, 30%, 40%, 50%, 60%, 70%, 80%, 90%, 100%, 150%, 200%, or more compared to the amount and/or rate of material damage by radicals and/or ROS in the absence of the self-regenerating antioxidant catalyst.

In some embodiments, the self-regenerating antioxidant catalyst may be attached to an implant material and/or may catalytically reduce oxidative stress in tissue(s) (e.g., biological tissue(s)) in contact with and/or adjacent to the self-regenerating antioxidant catalyst and/or implant material. The self-regenerating antioxidant catalyst and/or implant material may reduce and/or prevent artificial implant failure caused by FBR. In some embodiments, the self-regenerating antioxidant catalyst may reduce and/or prevent immune response-mediated material degradation and/or loss of function. Chemical and/or mechanical degradation of a material (e.g., an artificial implant material) in which the self-regenerating antioxidant catalyst is in, on, and/or adjacent to may be reduced and/or prevented. In some embodiments, the self-regenerating antioxidant catalyst may reduce and/or prevent corrosion and/or mechanical stress/strain forces in a material in which the self-regenerating antioxidant catalyst is in, on, and/or adjacent to.

In some embodiments, the self-regenerating antioxidant catalyst may be integrated (e.g., covalently integrated) into a polymer, such as, e.g., an organic polymer, that retains the catalytic activity of the self-regenerating antioxidant catalyst. For example, the self-regenerating antioxidant catalyst may be integrated (e.g., covalently integrated) into a polymer, such as, but not limited to, polyethylene, polypropylene, poly(methyl methacrylate), poly(dimethyl siloxane), and any combination thereof.

According to some embodiments of the present invention, the self-regenerating antioxidant catalyst comprises a benzimidazole and/or a derivative thereof. A "derivative" as used herein refers to a compound and/or group that has a common structure with the compound referred to (e.g., a parent compound and/or group), but is substituted with one or more substituents. For example, a self-regenerating antioxidant catalyst may comprise and/or be derived from a benzimidazole, but the benzimidazole of the self-regenerating antioxidant catalyst may be substituted with one or more substituents, such as, e.g., shown in Ru1 and Ru2. In some embodiments, the self-regenerating antioxidant catalyst comprises a chelating, anionic benzimidazole-based N-heterocyclic carbene (NHC) ligand. In some embodiments, the self-regenerating antioxidant catalyst comprises a bipyridine, a phosphine, an amine and/or a derivative thereof. In some embodiments, the self-regenerating antioxidant catalyst may comprise ruthenium (e.g., Ru(II)) and/or a ruthenium complex.

In some embodiments, a self-regenerating antioxidant catalyst of the present invention may include a substituent that allows and/or provides for the attachment (e.g., covalent attachment) of the self-regenerating antioxidant catalyst to an implant material (e.g., an artificial and/or biological implant material). Example substituents that may be used to attach a self-regenerating antioxidant catalyst to an implant material include, but are not limited to, methacrylamide, diethylphosphonate, and/or derivatives thereof. In some embodiments, a self-regenerating antioxidant catalyst may be attached (e.g., covalently attached) to (e.g., into and/or onto) an organic and/or inorganic material. Example materials include, but are not limited to, poly(methyl methacrylate) (PMMA) (e.g. a PMMA films) or $TiO_2$ (e.g., a $TiO_2$ nanoparticles).

The self-regenerating antioxidant catalyst may have a structure represented by one of the following structures:

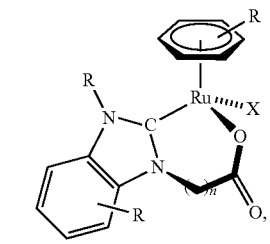

Ru1

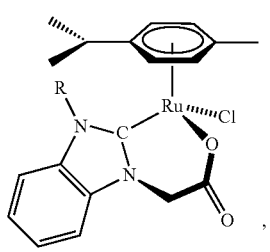

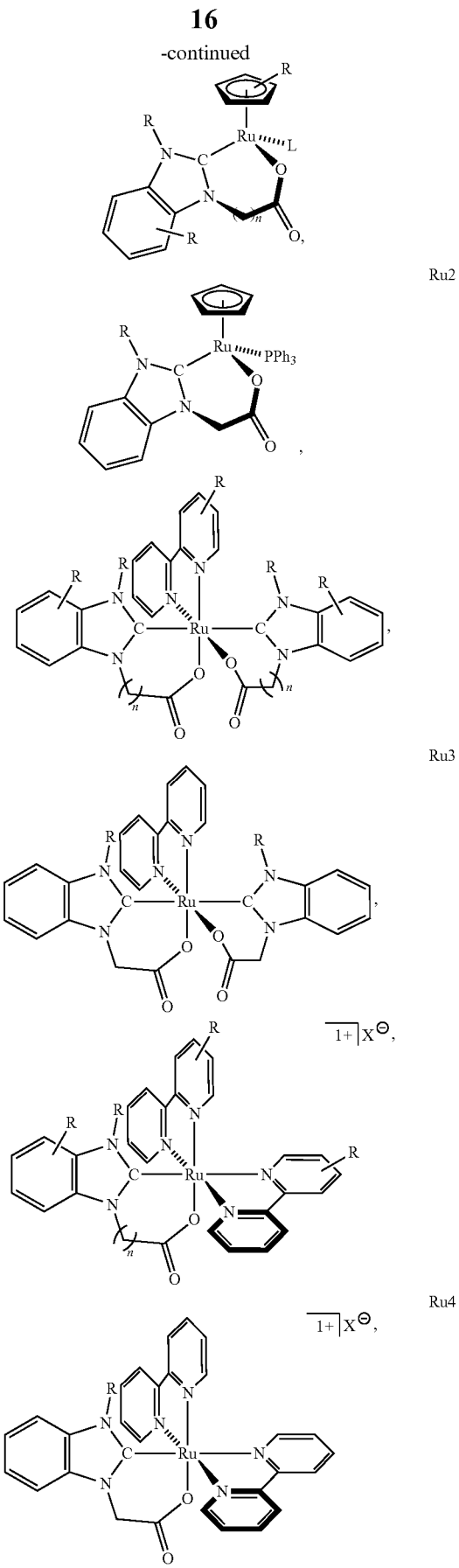

-continued

Ru5
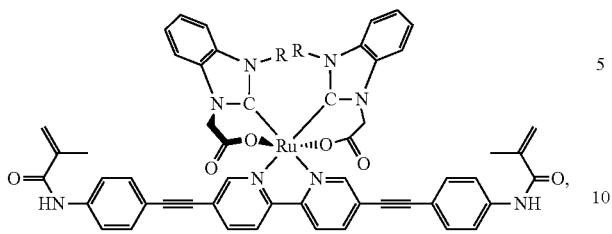

Ru6
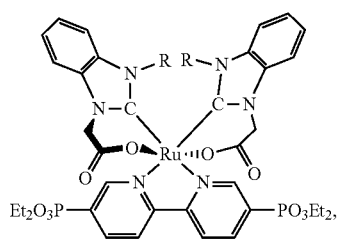

Ru7
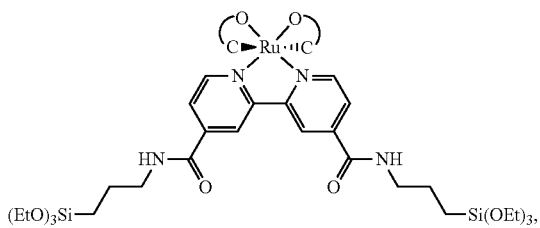

Ru9
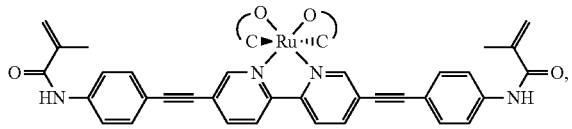

Ru10
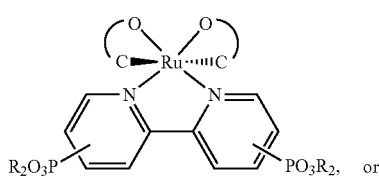
or

Ru-PPE
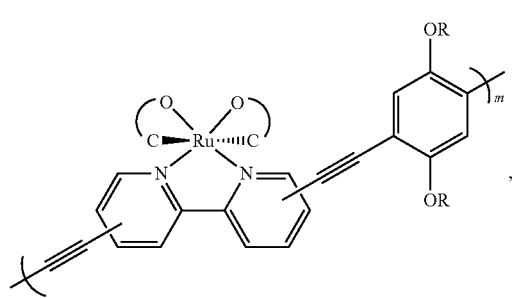

-continued wherein 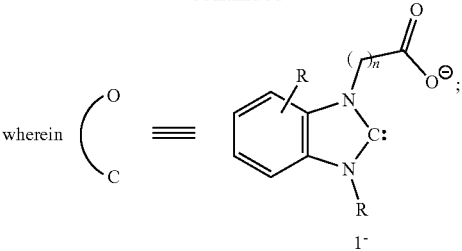

wherein
each R is independently a hydrogen, substituted or unsubstituted alkyl group, or a substituted or unsubstituted aryl group, wherein the substituted alkyl group or the substituted aryl group are substituted with a substituent selected from the group consisting of an alkyl group, alkenyl group, alkynyl group, halogen atom, carbonyl-containing functional group, aryl group, heterocyle, alcohol, thiol, amine, ether, thioether, azide, and any combination thereof;

X is a non-coordinating anion;
n is an integer from 1 to 30; and
m is an integer from 1 to 30;
and/or a derivative thereof.

In some embodiments, each R is hydrogen. In some embodiments, at least one R is a substituted or unsubstituted alkyl group or a substituted or unsubstituted aryl group. In some embodiments, "n" and/or "m" may each independently be any integer from 1 to 30, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30.

Example non-coordinating anions include, but are not limited to, tetrafluoroborate, hexafluorophosphate, tetraphenylborate, triflate, triflamide, methylsulfate, and any combination thereof.

In some embodiments, the self-regenerating antioxidant catalyst may retain the ability to degrade (e.g., reduce) radicals and/or ROS catalytically for a period of time. The self-regenerating antioxidant catalyst may retain the ability to degrade radicals and/or ROS catalytically for a given period of time, such as, e.g., 1, 2, 3, 4, 5, or 6 days, or 1, 2, 3, 3, 4, 5, or more weeks in aerobic, buffered (e.g., at a pH in a range of about 6 to about 8) aqueous solutions and/or under physiologically relevant conditions (e.g., at a pH in a range of about 6 to about 8). In some embodiments, the self-regenerating antioxidant catalyst may retain the ability to degrade radicals and/or ROS catalytically for at least 2 weeks in aerobic, buffered aqueous solutions and/or under physiologically relevant conditions.

In some embodiments, the self-regenerating antioxidant catalyst may utilize non-tertiary alcohols present in the environment in which the self-regenerating antioxidant catalyst is present, such as, for example, a biological system, to degrade radicals and/or ROS catalytically. In some embodiments, the self-regenerating antioxidant catalyst may use a sugar present in the environment in which the self-regenerating antioxidant catalyst is present, such as, for example, a biological system, to degrade radicals and/or ROS catalytically. In some embodiments, the self-regenerating antioxidant catalyst may utilize an oxidizing radical, such as, but not limited to hydrogen peroxide, present in the environment in which the self-regenerating antioxidant catalyst is present, such as, for example, a biological system, to degrade radicals (including the oxidizing radical, e.g., hydrogen peroxide) and/or ROS catalytically.

The self-regenerating antioxidant catalyst may be in, on, and/or in contact with at least a portion of a subject and/or a biological system. In some embodiments, the self-regenerating antioxidant catalyst may be in contact with a biological tissue and/or a biological fluid, such as, but not limited to, extracellular fluid, blood, lymph, pus, exudate, aqueous humour, vitreous humour, saliva, sweat, urine, etc. of a subject. Subjects suitable that may be in contact with a self-regenerating antioxidant catalyst of the present invention and/or treated with a method of the present invention include, but are not limited to, avian and mammalian subjects. Mammals of the present invention include, but are not limited to, canines, felines, bovines, caprines, equines, ovines, porcines, rodents (e.g. rats and mice), lagomorphs, primates, humans, and the like, and mammals in utero. Any mammalian subject in need of being treated according to the present invention is suitable. Human subjects of both genders and at any stage of development (i.e., neonate, infant, juvenile, adolescent, adult) may be treated according to the present invention. The invention may also be carried out on animal subjects, particularly mammalian subjects such as mice, rats, dogs, cats, livestock and horses for veterinary purposes, and for development purposes.

The self-regenerating antioxidant catalyst may be non-cytotoxic. In some embodiments, the self-regenerating antioxidant catalyst may be present in, on, and/or in contact with at least a portion of a material, subject and/or biological system in a therapeutically effective amount. In some embodiments, the therapeutically effective amount for a self-regenerating antioxidant catalyst of the present invention may be about 0.1 µM, 0.5 µM, 1 µM, 5 µM, 10 µM, 25 µM, 50 µM, 100 µM, 150 µM, 200 µM or more. The self-regenerating antioxidant catalyst may be present in a non-cytotoxic amount and/or at a concentration in a range of about 0.5 µM to about 100 µM and/or any range therein. In some embodiments, the therapeutically effective amount for a self-regenerating antioxidant catalyst of the present invention may be at least about 100 µM, such as, for example, for Ru1.

As used herein, the term "therapeutically effective amount" refers to an amount of a self-regenerating antioxidant catalyst of the present invention that elicits a therapeutically useful response in a subject and/or with regard to a material. Those skilled in the art will appreciate that the therapeutic effects need not be complete or curative, as long as some benefit is provided to the subject and/or material. In particular embodiments of the present invention, a therapeutically effective amount of a self-regenerating antioxidant catalyst results in the catalytic degradation of a ROS and/or radical, reduction in the rate of formation of a ROS and/or radical, and/or the reduction and/or prevention of material damage by a ROS and/or radical.

A self-regenerating antioxidant catalyst of the present invention may be attached to, such as, for example, covalently attached, to an implant material, such as, for example, an artificial and/or biomedical implant material. A surface (e.g., interior and/or exterior) of an implant material to which a self-regenerating antioxidant catalyst of the present invention may be attached include, but are not limited to, a metal, such as, for example, stainless steel, titanium, etc.; a polymer and/or plastic, such as, for example, fluoropolymer plastics, polyethylene, polypropylene, poly(methyl methacrylate), etc.; silicon dioxide; titanium dioxide; and any combination thereof. In some embodiments, the self-regenerating antioxidant catalyst may be attached to an existing, FDA-approved biomedical implant material. In some embodiments, the biomedical implant material may be functionalized with the self-regenerating antioxidant catalyst, thereby attaching the self-regenerating antioxidant catalyst to the biomedical implant material.

In some embodiments, a self-regenerating antioxidant catalyst of the present invention may be prepared from a compound represented by one of the following structures:

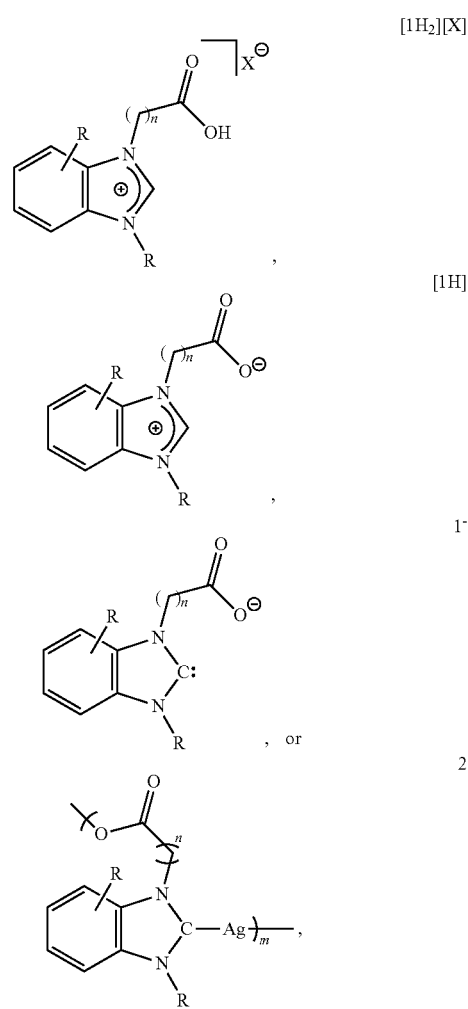

wherein each R is independently a hydrogen, substituted or unsubstituted alkyl group, or a substituted or unsubstituted aryl group, wherein the substituted alkyl group or the substituted aryl group are substituted with a substituent selected from the group consisting of an alkyl group, alkenyl group, alkynyl group, halogen atom, carbonyl-containing functional group, aryl group, heterocycle, alcohol, thiol, amine, ether, thioether, azide, and any combination thereof.

In some embodiments, R is a substituted aryl group. In some embodiments, R is 3,5-dimethylphenyl or 4-methylphenyl.

According to some embodiments of the present invention, provided are methods of using a self-regenerating antioxidant catalyst of the present invention. In some embodiments, a method of decreasing and/or preventing damage to a material (e.g., an articial and/or biomedical implant material) may be provided, the method comprising providing the material, the material comprising a self-regenerating antioxidant catalyst of the present invention on at least a portion of a surface of the material, thereby decreasing and/or preventing damage to the material. The self-regenerating antioxidant catalyst may be present on an interior and/or exterior surface of the material. In some embodiments, degradation of the material may be decreased and/or prevented. Some embodiments include that the self-regenerating antioxidant catalyst decreases and/or prevents damage to the material. In some embodiments, the self-regenerating antioxidant catalyst and/or method of decreasing and/or preventing damage to a material may decrease and/or prevent damage to the material when the material and/or self-regenerating antioxidant catalyst are exposed to and/or in contact with a biological system (e.g., when the material is implanted in a subject).

In some embodiments, a self-regenerating antioxidant catalyst and/or method of the present invention may reduce and/or prevent chemical and/or mechanical degradation of a material (e.g., an articifial and/or biomedical implant material). The self-regenerating antioxidant catalyst may reduce and/or prevent immune response-mediated material degradation in a biological system in which it is present. In some embodiments, the self-regenerating antioxidant catalyst may reduce and/or prevent loss of function of a material on which it is present.

The self-regenerating antioxidant catalyst may decrease the amount and/or rate of damage to a material by at least 5% or more, such as, for example, at least 10%, 15%, 20%, 25%, 30%, 35%, 40%, 45%, 50%, 55%, 60%, 65%, 70%, 75%, 80%, 85%, 90%, 95%, or 100% compared to a material without the self-regenerating antioxidant catalyst. In some embodiments, the self-regenerating antioxidant catalyst may decrease the amount and/or rate of damage to the implant material by at least 5% for a period of time of at least 1, 2, 3, 4, 5, 6 day(s), or 1, 2, 3, 4 or more week(s) compared to a material without the self-regenerating antioxidant catalyst under similar conditions.

In some embodiments, the self-regenerating antioxidant catalyst may decrease and/or prevent damage to a material (e.g., an articifial and/or biomedical implant material) by decreasing and/or preventing damage to the implant from oxidizing radicals, such as, for example, those produced by a sterile immune response and/or ROS. In some embodiments, the self-regenerating antioxidant may reduce and/or prevent the triggering of an immune response. The self-regenerating antioxidant catalyst may decrease the severity and/or duration of a sterile immune response. In some embodiments, the self-regenerating antioxidant catalyst may decrease and/or prevent triggering of a foreign body reaction. In some embodiments, the self-regenerating antioxidant catalyst may decrease and/or prevent severity and/or duration of the adverse effects of acute phase foreign body reaction.

The present invention is explained in greater detail in the following non-limiting Examples.

EXAMPLES

Example 1

A benzimidazolylidene with a chelating carboxylate sidechain (1⁻) was synthesized and its transition metal coordination chemistry and reactivity were studied (Scheme 1). To construct the framework for a chelating, anionic benzimidazole-based N-heterocyclic carbene (NHC) ligand (1⁻), N-(3,5-dimethylphenyl)benzimidazole was reacted with 2-bromoacetic acid to yield the corresponding benzimidazolium [1H$_2$][Br]. Double deprotonation followed by metallation of [1H$_2$][Br] with Ag$_2$O produced the Ag—NHC complex [Ag(1)]$_n$ (2), which exhibited good solubility in organic solvents despite its multinuclear nature. Crystallographic analysis of 2 revealed a dodecametallic structure (n=12) comprising mononuclear [Ag(1)] and dinuclear [Ag$_2$(1)$_2$] subunits, the latter of which featured Ag—Ag bonds. Transmetallation of 1⁻ from Ag to Ru via the reaction of [RuCl(η$^6$-cymene)(μ-Cl)]$_2$ with 2 afforded the Ru—NHC complex [RuCl(1)(η$^6$-cymene)](Ru1), which demonstrated catalytic activity for transfer hydrogenation of C═O, C═N and C═C bonds using isopropanol as the H$_2$ source.

Scheme 1: Benzimidazole scaffold

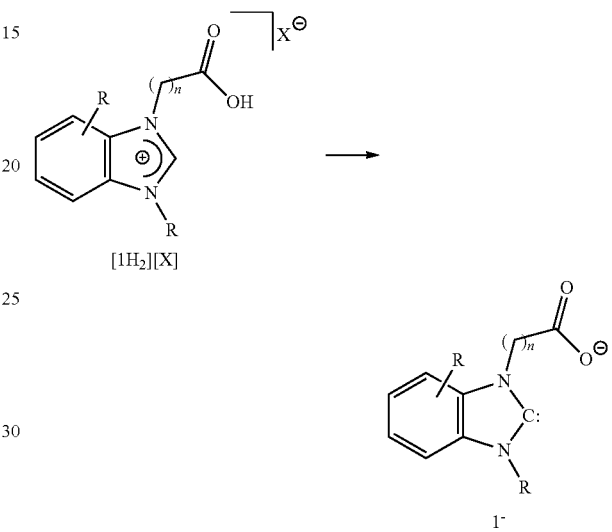

Experimental:
Materials and Methods

N-(3,5-dimethylphenyl)benzimidazole was prepared as previously described (Hanan, et al., Lyssikatos, Synlett (2010) 2759). All other materials and solvents were of reagent quality and used as received. $^1$H and $^{13}$C{$^1$H}NMR spectra were recorded using a Bruker 500 MHz spectrometer. Chemical shifts δ (in ppm) for $^1$H and $^{13}$C NMR are referenced to SiMe$_4$ using the residual protio-solvent as an internal standard. For $^1$H NMR: CDCl$_3$, 7.26 ppm; DMSO-d$_6$, 2.50 ppm. For $^{13}$C NMR: CDCl$_3$, 77.16 ppm; DMSO-d$_6$, 39.52 ppm. Coupling constants (J) are expressed in hertz (Hz). Infrared spectra were recorded on a Thermo Nicolet IR200 spectrometer with 4 cm$^{-1}$ resolution. Elemental analyses were performed at Atlantic Microlab, Inc. (Norcross, Ga.). All syntheses and purifications were performed under ambient conditions unless specified otherwise. Syntheses requiring an inert atmosphere were performed under an N$_2$ atmosphere using standard Schlenk or glovebox techniques. When required, solvents were dried and deoxygenated using an Innovative Technologies solvent purification system, and then stored over molecular sieves (3 Å) in a drybox.

Crystal Structure Data Acquisition and Structure Determination

Single crystals of [1H$_2$][Br] and Ru1 were immersed in Paratone-N oil at room temperature and mounted on glass fibers using epoxy glue. To protect crystals of 2 from rapid desolvation, those crystals were transferred from the solvent into cold, viscous Paratone-N oil, mounted on a glass fiber, and immediately cooled to 200 K under a stream of cold nitrogen. Intensity data on all crystals were collected under nitrogen at 200 K with Mo Kα radiation (λ=0.71073 Å) on a Rigaku AFC8S diffractometer equipped with a Mercury CCD area detector and controlled using the CrystalClear software package [23]. A crystal-to-detector distance of 27 mm was used for [1H$_2$][Br] and Ru1, whereas the data collection for 2 required a crystal-to-detector distance of 42 mm accompanied by a detector swing of 12 degrees to resolve the diffraction profile and retain appropriate resolution limits. Data were corrected for absorption as well as Lorentz and polarization effects using the REQAB subroutine of CrystalClear [24]. The structures were solved by direct methods and subsequently refined using the SHELXTL software package [25] and checked for higher symmetry using the PLATON program suite [26]. All non-hydrogen atoms were refined anisotropically. Hydrogen atoms were placed at calculated positions using a riding model and assigned thermal parameters equal to either 1.5 (methyl hydrogen atoms) or 1.2 (non-methyl hydrogen atoms) times the thermal parameters of the atoms to which they were attached. For Ru1, a partially-occupied solvent molecule was identified from the difference electron density map and included in the refinement. In the case of 2, several solvent molecules could be identified from the difference map, and other highly disordered solvent molecules were modeled using the SQUEEZE tool of PLATON.

Syntheses

Synthesis of 2-(3-{3,5-dimethylphenyl}-benzimidazol-1-ium-1-yl)acetate hydrobromide [1H$_2$][Br]

2-Bromoacetic acid (947 mg, 6.82 mmol) and N-(3,5-dimethylphenyl)benzimidazole (1.50 g, 6.75 mmol) were dissolved with 20 mL of toluene in a heavy-walled flask equipped with a stir bar. The flask was then sealed and the clear, dark orange-brown solution was heated to 110° C. After 16 h, a white precipitate had formed, at which point the reaction mixture was allowed to cool to room temperature and the precipitate was collected by filtration. The resulting solid was washed successively with Et$_2$O, CH$_2$Cl$_2$ and acetone, and then dried in vacuo to afford 1.95 g (5.40 mmol, 80% yield) of the desired product as a white powder. $^1$H NMR (500 MHz, DMSO-d$_6$): δ=13.93 (s, 1H), 10.25 (s, 1H), 8.19 (d, J=8.5, 1H), 7.91 (d, J=8.0, 1H), 7.81-7.71 (m, 2H), 7.50 (s, 2H), 7.36 (s, 1H), 5.60 (s, 2H), 2.43 (s, 6H). $^{13}$C NMR (125 MHz, DMSO-d$_6$): δ 167.5, 143.3, 140.1, 132.8, 131.8, 131.5, 130.5, 127.4, 127.2, 122.4, 114.3, 113.7, 47.8, 20.7. IR (KBr): 3116 (w), 3024 (m), 2902 (m), 2761 (m), 2566 (w), 2511 (w), 2428 (w), 1742 (vs), 1731 (vs), 1620 (s), 1598 (m), 1557 (vs), 1487 (s), 1435 (m), 1401 (s), 1384 (s), 1366 (m), 1351 (m), 1326 (m), 1265 (m), 1232 (vs), 1221 (vs), 1202 (vs), 1149 (m), 1138 (w), 1030 (w), 999 (w), 879 (m), 856 (s), 779 (s), 746 (s), 692(s), 679 (m), 607 (m), 424 (w) cm$^{-1}$. Anal. Calcd for C$_{17}$H$_{17}$BrN$_2$O$_2$: C, 56.52; H, 4.74; N, 7.75. Found: C, 56.62; H, 4.79; N, 7.67.

Synthesis of [Ag(1)]$_n$ (2)

To a solution of [1H$_2$][Br](100 mg, 277 μmol) in anhydrous CH$_2$Cl$_2$ (10 mL) under nitrogen was added Ag$_2$O (96.2 mg, 415 μmol), and the resulting white suspension was allowed to stir at room temperature in the absence of light. After 24 h, the reaction mixture was filtered through a 0.2 μm PTFE filter with the aid of CH$_2$Cl$_2$ (2 mL). The filtrate solvent was removed under reduced pressure and the resulting solids were then dried in vacuo to afford 104 mg (269 μmol, 97% yield) of the desired product as an off-white powder. $^1$H NMR (500 MHz, CDCl$_3$): δ 7.52 (d, J=8.0, 1H), 7.37-7.32 (m, 2H), 7.31-7.27 (m, 1H), 7.21 (s, 2H), 7.10 (s, 1H), 5.17 (s, 2H), 2.39 (s, 6H). $^{13}$C NMR (125 MHz, CDCl$_3$): δ 188.7, 171.9, 139.9, 138.1, 134.6, 134.5, 130.9, 124.3, 124.01, 123.99, 112.4, 112.1, 53.0, 21.4. IR (KBr): 3055 (m), 2976 (w), 2920 (m), 1614 (vs), 1483 (s), 1435 (m), 1383 (vs), 1308 (s), 1248 (m), 1184 (w), 1103 (vw), 1030 (w), 997 (vw), 914 (vw), 856 (m), 837 (w), 748 (s), 652 (m), 625 (m), 550 (vw), 432 (vw) cm$^{-1}$. Anal. Calcd for C$_{17}$H$_{16}$N$_2$O$_{2.5}$Ag (2.0.5H$_2$O): C, 51.54; H, 4.07; N, 7.07. Found: C, 51.86; H, 4.00; N, 7.05.

Synthesis of [RuCl(1) (η$^6$-cymene)](Ru1)

To a stirred solution of 2 (100 mg, 258 μmol) in anhydrous CH$_2$Cl$_2$ (10 mL) under nitrogen was added [RuCl(η$^6$-cymene)(μ-Cl)]$_2$ (79.1 mg, 258 μmol) dissolved in 10 mL of CH$_2$Cl$_2$. During the course of the addition, the mixture changed first to a clear red and then to a clear orange solution with concomitant formation of a white precipitate, and the reaction was allowed to stir at room temperature. After 24 h, the reaction mixture was filtered through a 0.2 μm PTFE filter (to remove AgCl) with the aid of CH$_2$Cl$_2$ (4 mL). The filtrate solvent was removed under reduced pressure and the resulting solids were then dried in vacuo to afford 138 mg (251 μmol, 97% yield) of the desired product as a light red-orange powder. $^1$H NMR (500 MHz, CDCl$_3$): δ 7.65 (s, 1H), 7.37-7.32 (m, 2H), 7.27-7.23 (m, 3H), 7.08 (d, J=8.0, 1H), 5.49 (d, J=6.0, 1H), 5.18 (d, J=6.0, 1H), 5.10 (d, J=6.0, 1H), 4.90 (d, J=16.5, 1H), 4.71 (d, J=17.0, 1H), 3.84 (d, J=5.5, 1H), 2.62 (sep, 1H), 2.51 (s, 3H), 2.42 (s, 3H), 2.01 (s, 3H), 1.11 (d, J=10.8, 3H), 1.09 (d, J=10.8, 3H). $^{13}$C NMR (125 MHz, CDCl$_3$): δ 186.0, 169.3, 140.6, 139.2, 138.6, 136.6, 134.0, 131.5, 128.9, 125.1, 124.2, 124.1, 111.4, 110.2, 104.0, 102.1, 90.5, 90.3, 83.3, 80.8, 49.9, 30.8, 23.3, 21.9, 21.4, 21.3, 18.9. IR (KBr): 3049 (w), 3026 (vw), 2961 (w), 2923 (w), 2871 (w), 1634 (vs), 1506 (vw), 1483 (w), 1470 (w), 1450 (m), 1395 (s), 1359 (m), 1306 (w), 1252 (w), 1205 (w), 944 (vw), 866 (w), 758 (m), 733 (w), 700 (w), 675 (vw), 634 (vw), 559 (vw), 436 (vw) cm$^{-1}$. Anal. Calcd for C$_{27}$H$_{29}$ClN$_2$O$_2$Ru: C, 58.96; H, 5.31; N, 5.09. Found: C, 58.77; H, 5.40; N, 5.02.

General Procedure for Transfer Hydrogenation Experiments

Unsaturated substrate (0.91 mmol), base (46 μmol) and Ru1 (9.1 μmol) were dissolved in dry $^i$PrOH under nitrogen and the resulting solution was heated to 83° C. After 24 h, the reaction mixture was allowed to cool to room temperature, diluted with 20 mL of CH$_2$Cl$_2$, washed with water (3×20 mL), dried with Na$_2$SO$_4$, and the solvent was removed under reduced pressure. This crude material was then purified via flash column chromatography (SiO$_2$, CH$_2$Cl$_2$). Product identity was confirmed by $^1$H NMR analysis. Reported yields are averages of two or more runs.

Results and Discussion:

Synthesis 3,5-dimethylphenyl was selected as a suitable benzimidazole N-substituent given its $^1$H NMR spectroscopic features: singlets for both alkyl and aryl protons, and the two methyl groups would readily reveal diastereotopic inequivalence within metal complexes. As the first step towards a carboxylate-functionalized NHC ligand, alkylation of the benzimidazole scaffold with ω-haloalkanoic acid, was pursued given that this reactivity has been demonstrated for N-substituted imidazoles [17c, 27]. Nucleophilic substitution of 2-bromoacetic acid by N-(3,5-dimethylphenyl)benzimidazole in toluene at 110° C. produced the benzimidazolium carboxylic acid [1H$_2$][Br] as an air- and moisture-stable white powder in 80% yield (Scheme 2). Although benzimidazole protonation could be competitive with alkylation under these reaction conditions, it is not the major product. Incomplete reactions do exhibit $^1$H NMR peaks consistent with a benzimidazolium species other than [1H$_2$][Br] that lacks an acetyl moiety. Continuing these reactions affords [1H$_2$][Br] as the predominant product, suggesting that benzimidazole protonation is reversible and does not preclude N-alkylation.

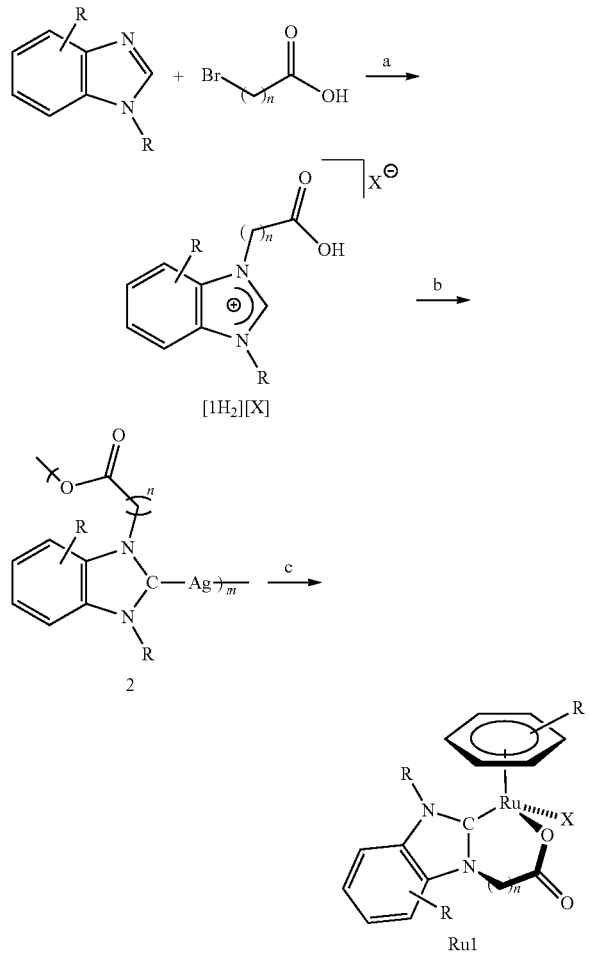

Reagents and contitions: (a) toluene, 110° C., 16 h; (b) 1.5 equiv. Ag$_2$O, CH$_2$Cl$_2$, RT, 24 h; (c) 0.5 equiv. [RuCl($\eta^6$-cymene)($\mu$-Cl)]$_2$, CH$_2$Cl$_2$, RT, 24 h. R = 3,5-dimethylphenyl.

Silver-NHC complexes are versatile transmetallating agents which can transfer NHC ligands to other metals without requiring synthesis and isolation of free NHCs [28]. Therefore, to access the corresponding silver-NHC complex of 1$^-$, deprotonation and metallation at the carboxylic acid and benzimidazolium 2-position were pursued via treatment of [1H$_2$][Br] with Ag$_2$O in CH$_2$Cl$_2$ which afforded [Ag(1)]$_n$ (2) as an air- and moisture-stable off-white powder in near-quantitative yield (97%). Despite its multinuclear nature, complex 2 has good solubility in organic solvents such as CH$_2$Cl$_2$, CHCl$_3$ and DMSO, and its $^1$H NMR spectra exhibit sharp, well-resolved peaks.

Precipitation of AgX generated upon dissociation from an NHC—AgX species is often the kinetic driving force for the transfer of a neutral NHC ligand to another metal. However, complex 2 contains no halides due to the nature of 1$^-$ as an L,X-type ligand and can thus transfer an NHC to another metal complex with concomitant halide abstraction. Indeed, treatment of 2 with [RuCl($\eta^6$-cymene)($\mu$-Cl)]$_2$ in CH$_2$Cl$_2$ led to formation of a precipitate (AgCl), affording the Ru—NHC complex [RuCl(1)($\eta^6$-cymene)]$_2$ (Ru1) as an air- and moisture-stable orange powder in near-quantitative yield (97%). This reaction afforded analytically pure material without the need for chromatography, crystallization or other purification techniques.

Spectroscopy

Conversion of N-(3,5-dimethylphenyl)benz-imidazole to [1H$_2$][Br] generates a formal positive charge in the benzimidazole core, which is reflected by the $^1$H NMR signal at 10.27 ppm (DMSO-d$_6$) for the C-2 proton (vs. 8.09 ppm in CDCl$_3$ for the benzimidazole precursor) [29]. This downfield shift is accompanied by the appearance of new peaks at 13.94 and 5.60 ppm, corresponding to the CO$_2$H and the N—CH$_2$ protons, respectively (Table 1). N-Aryl imidazolium carboxylic acids Ia [27] and Ib [17c] (FIG. 1) bear closest structural resemblance to [1H$_2$][Br], but the chemical shifts for the N—CH$_2$ signals (5.32 ppm for both) and C-2 protons (9.63 and 9.62, respectively) were more upfield, reflecting the greater electron richness of the imidazole- vs. benzimidazole-based aromatic systems.

TABLE 1

| Selected NMR spectroscopic features [a] | | | |
|---|---|---|---|
| | $\delta$H(NCH$_2$) | $\delta$H(3,5-Me$_2$) | $\delta$C(NCN) |
| [1H$_2$][Br] [b] | 5.60 | 2.43 | 143.3 |
| 2 | 5.17 | 2.39 | 188.7 |
| Ru1 | 4.90 (d), 4.71 (d) | 2.51, 2.42 | 186.0 |

[a] Spectra acquired in CDCl$_3$ or [b] DMSO-d$_6$. Chemical shifts ($\delta$) in ppm.

Situated between the NHC and carboxylate moieties, the N—CH$_2$ protons will be diagnostic for the stereoelectronic environment of 1$^-$ in metal complexes. Cationic benzimidazolium and neutral CO$_2$H groups in [1H$_2$][Br] are formally converted to their respective neutral NHC and anionic CO$_2^-$ groups in 2, and this increase in electron-richness is accompanied by an upfield shift in the N—CH$_2$ signals from 5.60 ppm (DMSO-d$_6$) to 5.17 ppm (CDCl$_3$). Conversely, the $^{13}$C NMR signal for the 2-position is shifted significantly downfield to 188.7 ppm (vs. 143.3 ppm for [1H$_2$][Br]) and considerably broadened, consistent with (i) the carbenoid nature of the carbon and (ii) coordination to silver. The shift for 2 is also consistent with the range of values (175.7-206.9 ppm) observed for NHC-supported silver complexes with ancillary $\kappa^1$O-carboxylate ligands [30]. No exact analog of 2 comprising Ag coordinated to a carboxylate-functionalized NHC in a 1:1 ratio has been previously reported, but there are examples of silver complexes with anionic NHC ligands in 1:2 ratios (e.g. IIa and IIb, FIG. 1) [31]. The $^1$H NMR signals for the N—CH$_2$ protons in IIa and IIb (4.30 and 4.08 ppm, respectively) are significantly upfield of the corresponding signal in 2 (5.17 ppm), where the more electron rich character of the ligands in IIa and IIb could be due to the negative overall charge on these complexes.

Transmetallation from 2 to Ru1 is accompanied by a change in the N—CH$_2$ resonance from one singlet at 5.17 ppm to two doublets at 4.90 and 4.71 ppm (J=16.5 and 17 Hz, respectively). Additionally, the methyl groups on the N-aryl substituent that in 2 afford a single peak (2.39 ppm) instead afford two peaks in Ru1 (2.51 and 2.42 ppm).

Collectively, the splitting of the N—CH$_2$ and 3,5-Me$_2$ signals in Ru1 reflects their diastereotopic nature, which suggests that 1$^-$ binds to Ru with the NHC and carboxylate moieties in a chelate ring. Similar diastereotopically inequivalent features are observed in analogous cymene-ruthenium complexes supported by carboxylate-functionalized imidazole-based NHCs (e.g. IIIa and IIIb, FIG. 1) [17a, 32]. Complex IIIa, for example, exhibits two doublets for the N—CH$_2$ protons (5.00 and 4.23 ppm, J=15.5 Hz) and two singlets for the 2,6-Me$_2$ protons (2.29 and 2.05 ppm) [17a].

and carboxylate substituents in 2$_{Ag1}$ rotated 50±11° and 101±6° relative to the benzimidazole core (vs. 44.0(4)° and 99.5(3)° in [1H$_2$][Br], respectively). No significant difference in the ratio of C—O to C=O bond distances was observed for 2$_{Ag1}$ relative to [1H$_2$][Br] (1.10 vs. 1.09, respectively), suggesting that the bonding within the carboxylate is relatively unchanged upon replacement of the H$^+$ in [1H$_2$][Br] with the Ag$^+$ in the 2$_{Ag1}$. Unlike [1H$_2$][Br], the C=O in 2$_{Ag1}$ is directed towards the benzimidazole core, presumably due to steric effects from the 2$_{Ag2}$ bound to the C—O.

TABLE 2

| | Selected bond lengths and angles [a] | | | |
|---|---|---|---|---|
| | d(M—C) | d(M—O) | ∠(CMO) | ∠(CNCC) |
| 2$_{Ag1}$ | 2.064 ± 0.027 | 2.114 ± 0.015 | 175.5 ± 2.4 | 101 ± 6 |
| 2$_{Ag2}$ | 2.060 ± 0.026 | 2.125 ± 0.027 | 167.0 ± 2.9 | 108 ± 4 |
| | 2.112 ± 0.006 | 2.664 ± 0.055 | 111.4 ± 2.0 | 94 ± 8 |
| IIb [b] | 2.069 (3) | — | — | 90.5 (3) |
| NHC—Ag—O$_2$C [c] | 2.052-2.0896 | 2.085-2.25 | 153.14-178.76 | — |
| NHC—Ag . . . Ag—NHC [d] | 2.06-2.096 | — | — | — |
| Ru1 | 2.020 (5) | 2.111 (4) | 84.49 (18) | 45.7 (7) |
| IIIa [e] | 2.033 (9) | 2.079 (8) | 86.7 (3) | 40 (1) |
| IIIb [f] | 2.032 (3) | 2.083 (2) | 86.0 (1) | 38.9 (4) |
| Ru—O$_2$C in 6-membered chelate ring [g] | — | 2.065-2.115 | 82.4-92.8 | — |
| arene-Ru—NHC [h] | 2.003-2.089 | — | — | — |

[a] Values listed for 2$_{Ag1}$ and 2$_{Ag2}$ are the average ± standard deviation of the four comparable subunits. The top and bottom rows for 2$_{Ag2}$ are for the 2- and 3-coordinate metal centers, respectively. Distances (d) in angstroms (Å) and angles (∠) in degrees (°). Literature data obtained from reference [b] 31, [c] 30, [d] 35, [e] 17a, [f] 32, [g] 39, and [h] 33 and 40.

Another notable spectral change upon conversion of 2 to Ru1 is the sharpening of the $^{13}$C NMR signal for the 2-position (186.0 ppm). This peak in Ru1 is upfield of the corresponding signals in IIIa and IIIb (171.0 and 174.9 ppm, respectively) [17a, 32], but it is within the range of values observed for benzimidazolylidene-supported arene-ruthenium complexes (184.1-191.7 ppm) [33]. On average, the $^{13}$C NMR shifts for the 2-position in the benzimidazolylidene-supported complexes (186.7 ppm) are higher than in the non-benzimidazolylidene complexes (178.6 ppm), thus the downfield shift of Ru1 vs. IIIa and IIIb is consistent with this trend.

Crystallography

Figure 2:
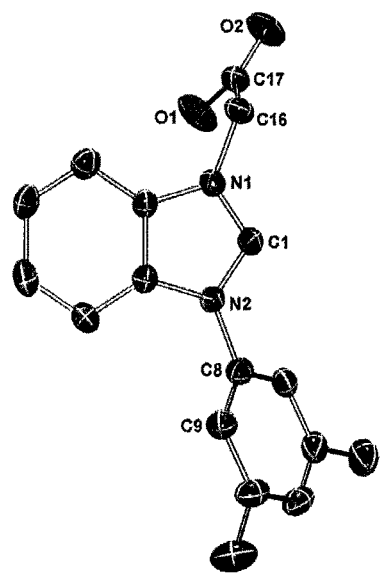
FIG. 2 shows an ORTEP diagram rendered using the POV-Ray engine, shown with 50% probability thermal ellipsoids and selected atom labels for [1H₂][Br]. Hydrogen atoms and counterions have been omitted for clarity. Selected distances (Å) and angles (°): N1-C1, 1.327(4); N2-C1, 1.328(4); O1-C17, 1.306(4); O2-C17, 1.199(4); N1-C1-N2, 110.3(3); C1-N1-C16-C17, 99.5(3); C1-N2-C8-C9, 44.0(4).

Diffraction-quality single crystals of [1H$_2$][Br] were obtained from a saturated EtOH solution via vapor diffusion of Et$_2$O at room temperature (FIG. 2). Crystallographic analysis revealed the carboxylic acid to be oriented nearly perpendicular to the benzimidazolium core (99.5(3)°), a feature consistent with the structure reported for Ib (73.8(3)°) [17c]. In contrast, the N-aryl substituent was more coplanar with the benzimidazolium core in [1H$_2$][Br] than the imidazolium core in Ib (44.0(4)° vs. 82.8(3)°, respectively), due to the greater steric influence of the 2,6-diisopropyl substituents in the latter. A feature of [1H$_2$][Br] is that the bond distance for the C=O functionality (1.199(4) Å) is among the shortest observed for this class of molecules (1.201-1.2398 Å) [17c, 34].

Figure 3A:
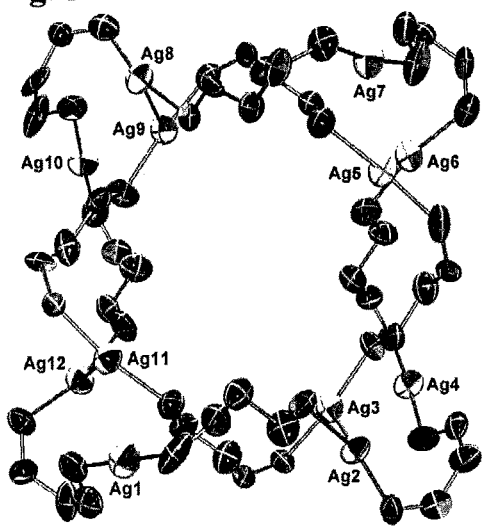
FIG. 3A shows an ORTEP diagram rendered using the POV-Ray engine, shown with 50% probability thermal ellipsoids and selected atom labels for the dodecametallic cyclic structure of 2. All atoms not in the $Ag_{12}$ ring have been omitted for clarity.
Figure 3B:
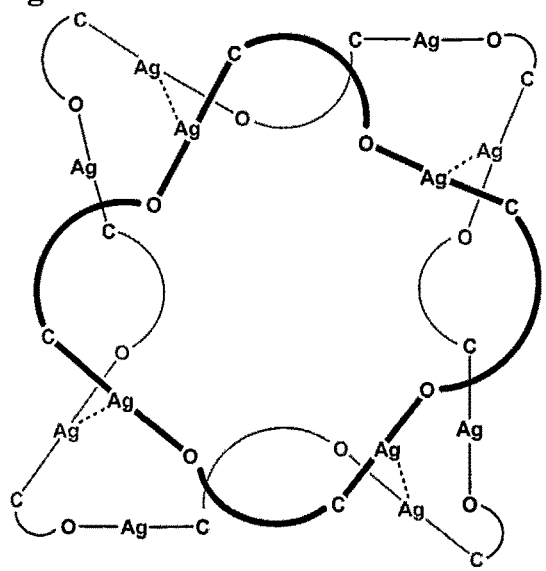
FIG. 3B shows a simplified representation of Ag—NHC connectivity for the dodecametallic cyclic structure of 2.
Figure 4:
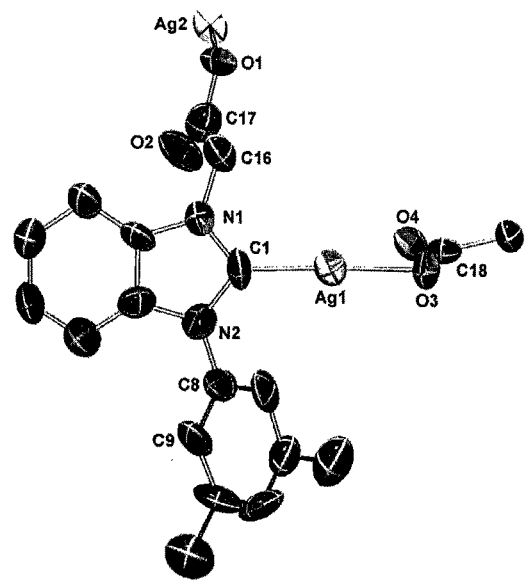
FIG. 4 shows an ORTEP diagram rendered using the POV-Ray engine, shown with 50% probability thermal ellipsoids and selected atom labels for $2_{Ag1}$. Hydrogen atoms and solvent molecules have been omitted for clarity. Selected distances (Å) and angles (°): Ag1-C1, 2.038(11); Ag1-O3, 2.111(8); Ag2-O1, 2.094(9); N1-C1, 1.363(15); N2-C1, 1.416(16); O1-C17, 1.324(17); O2-C17, 1.194(17); C1-Ag1-O3, 175.5(5); N1-C1-N2, 101.8(10); C1-N1-C16-C17, 106(2); C1-N2-C8-C9, 41(2).
Figure 5:
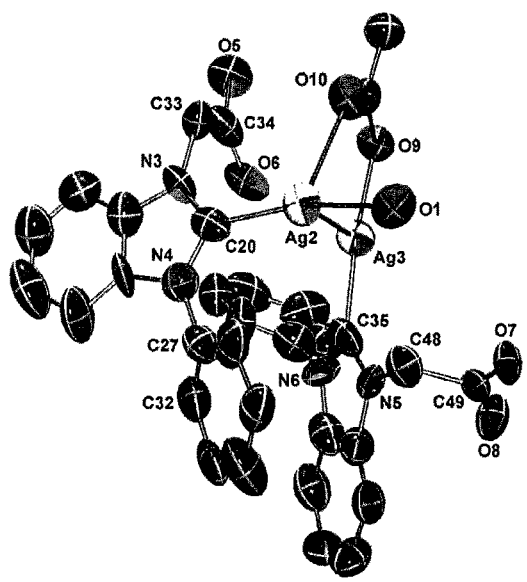
FIG. 5 shows an ORTEP diagram rendered using the POV-Ray engine, shown with 50% probability thermal ellipsoids and selected atom labels for $2_{Ag2}$. Hydrogen atoms and solvent molecules have been omitted for clarity. Selected distances (Å) and angles (°): Ag2 . . . Ag3, 2.967(2); Ag2-C20, 2.120(14); Ag2-O1, 2.094(9); Ag2-O10, 2.702(2); Ag3-C35, 2.097(14); Ag3-O9, 2.125(9); N4-aryl (centroid)-Ag3-NHC(centroid), 3.989; N3-C20, 1.309(16); N4-C20, 1.317(15); N5-C35, 1.404(18); N6-C35, 1.366(16); O5-C34, 1.271(17); O6-C34, 1.330(19); O7-C49, 1.259(16); O8-C49, 1.219(15); N3-C20-N4, 106.6(12); N5-C35-N6, 107.5(12); O1-Ag2-C20, 165.8(5); O10-Ag2-C20, 109.3(5); O9-Ag3-C35, 165.4(5); C20-Ag2-Ag3-C35, 75.4(6); C20-N3-C33-C34, 98(2); C20-N4-C27-C32, 37(2); C35-N5-C48-C49, 114(2); O9-Ag3-Ag2-O10, 4.0(4).

Silver(I) commonly adopts a 2-coordinate geometry with ligands oriented nearly 180° apart, but given that 1$^-$ cannot trans-chelate, it was expected that 2 would exhibit a multinuclear structure. Crystallographic analysis revealed that 2 exists in the solid state as a dodecametallic cyclic species (FIGS. 3A and 3B), comprising four distinct [Ag(1)] and [Ag$_2$(1)$_2$] subunits (2$_{Ag1}$ and 2$_{Ag2}$, respectively, FIGS. 4 and 5, respectively). The organic framework in 2$_{Ag1}$ (FIG. 4) is largely unchanged from the ligand precursor, with the N-aryl Mononuclear silver-NHC complexes with κ$^1$O-carboxylate ligands have been previously reported [30], with carbon-silver and oxygen-silver bond distances of 2.052-2.0896 Å and 2.085-2.25 Å, respectively. Although the Ag—O distances in 2$_{Ag1}$ (2.114±0.015 Å, Table 2) are near the middle of the range observed for related complexes, the Ag—C distances (2.064±0.027 Å) are among the shortest. Similarly, the C—Ag—O angle of 175.5±2.4° for 2$_{Ag1}$ is one of the most linear measured for these complexes (153.14-178.76°). Compared to the corresponding values in IIb (Ag—C=2.069(3) Å and C—Ag—C'=180.0(1)°) [31], however, 2$_{Ag1}$ appears consistent with the motif for Ag complexes with anionic NHCs.

One prominent feature of the bimetallic 2$_{Ag2}$ subunits is the presence of a close silver-silver contact (FIG. 5), with an Ag . . . Ag distance of 2.945±0.019 Å that is consistent with the values determined for other NHC-supported Ag . . . Ag complexes (2.782-3.124 Å) [35]. Because the Ag . . . Ag distance in 2$_{Ag2}$ is less than twice the van der Waals radius for Ag (3.44 Å), some degree of closed-shell d$^{10}$-d$^{10}$ metallophilic interactions can be inferred [36]. Interestingly, the two metal centers in 2$_{Ag2}$ have different coordination environments: one Ag is bound by two carboxylates (e.g. Ag2) and the other is bound by one (e.g. Ag3), where the former exhibits a longer Ag—C distance than the latter (2.112±0.006 Å vs. 2.060±0.026 Å, respectively). Silver-carbon bond lengths measured in other NHC-supported Ag . . . Ag complexes range from 2.06(2) to 2.096(5) Å [35], which places the Ag—C distances in 2$_{Ag2}$ among the shortest and longest. The NHC—Ag bond vectors in these previously-reported bimetallic complexes were observed to be orthogonal with each other (77.2-96.71°), and the corresponding C—Ag . . . Ag—C dihedral angle in 2$_{Ag2}$ of 73.5±1.8° followed this trend.

Excluding the closed-shell d$^{10}$-d$^{10}$ interaction, the silver bound by two carboxylates displays a 3-coordinate, distorted T-shape geometry (C—Ag-O$_{cis}$=111.4±2.00, C—Ag—O$_{trans}$=165.0±1.4°), whereas the silver bound by one carboxylate displays a 2-coordinate, distorted linear geometry (C—Ag—O=169.1±2.5°). Moreover, the metric parameters for the 2-coordinate silver in $2_{Ag2}$ are highly conserved with those for the silver in $2_{Ag1}$. For the 3-coordinate silver in $2_{Ag2}$, the bond to the cis carboxylate was significantly longer than the trans (2.664±0.055 Å vs. 2.138±0.034 Å), suggesting the former can be viewed as a neutral carbonyl interacting with a Lewis acid via its lone pair and the latter as an anionic oxygen coordinated to a metal. In support of this interpretation, the C—O distance in the carboxylate bound cis to the NHC (1.22 Å) is shorter than the trans (1.26 Å), indicating greater carbon-oxygen double bond character in the former.

In addition to the close Ag . . . Ag contact, the two [Ag(1)] constituents in $2_{Ag2}$ also exhibit an interaction between the π-systems of the N-aryl substituent of the ligand bound to the 3-coordinate silver and the NHC core of the ligand bound to the 2-coordinate silver. Given the centroid-centroid distance of 3.939±0.04 Å and high degree of coplanarity between the ring planes (6.37±1.68°), this π-π interaction is most appropriately classified as offset π-π stacking [37]. For comparison, π-π stacking has been observed in other NHC-supported metal complexes with centroid-centroid distances ranging from 3.307 Å to 4.725 Å [38], thus the value measured in $2_{Ag2}$ is consistent with this type of interaction.

Figure 6:
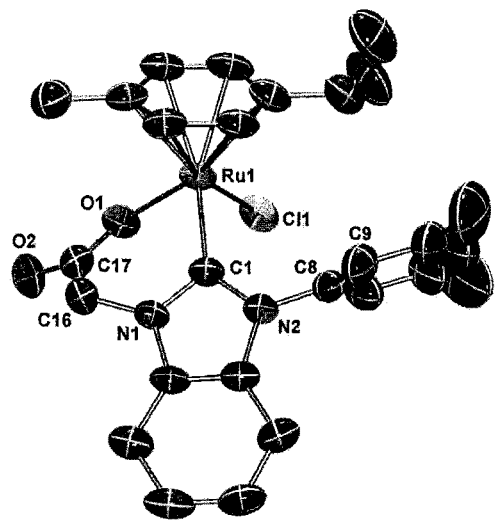
FIG. 6 shows an ORTEP diagram rendered using the POV-Ray engine, shown with 50% probability thermal ellipsoids and selected atom labels for Ru1. Hydrogen atoms and solvent molecules have been omitted for clarity. Selected distances (Å) and angles (°): Ru1-C1, 2.020(5); Ru-cymene(centroid), 1.696; Ru1-C11, 2.4152(15); Ru1-O1, 2.111(4); N1-C1, 1.363(6); N2-C1, 1.369(7); O1-C17, 1.281(7); O2-C17, 1.235(7); C1-Ru1-C11, 90.65(14); C1-Ru1-O1, 84.49(18); C11-Ru1-O1, 83.06(11); N1-C1-N2, 105.1(4); C1-N1-C16-C17, 45.7(7); C1-N2-C8-C9, 104.7(7).

Chelation of 1⁻ to Ru in complex Ru1, inferred by $^1$H NMR spectroscopy from the diastereotopic nature of the N—CH$_2$ protons, was confirmed by single crystal X-ray diffraction analysis (FIG. 6). The C1-Ru1-O1 angle of 84.49(18)° and Ru1-O1 distance of 2.111(4) Å in Ru1 were consistent with other complexes comprising 6-membered Ru-carboxylate chelate rings (82.4-92.8° and 2.065-2.115 Å, respectively) [39]. Previously reported NHC-supported cymene-ruthenium complexes exhibited Ru-arene centroid and Ru—NHC bond distances of 1.677-1.731 Å and 2.003-2.089 Å, respectively, and the corresponding values measured in Ru1 (Ru-cymene centroid=1.696 Å; Ru1-C1=2.020 (5) Å) fall within these ranges [40]. These cymene complexes do not contain benzimidazole-based NHCs, but the relatively few crystallographically characterized benzimidazolylidene-ruthenium complexes bearing any kind of arene ligand exhibit Ru-centroid and Ru—NHC distances (1.658-1.721 Å and 2.016-2.089 Å) that are highly conserved with those for cymene-ruthenium-imidazolylidene complexes [33]. Collectively, the structural features observed in Ru1 suggest that coordination chemistry of the individual benzimid-azolylidene and carboxylate components in 1⁻ are not significantly perturbed by the chelating linker.

Catalysis

Figure 7:
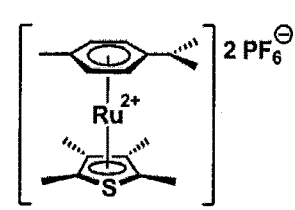
FIG. 7 shows examples of NHC-supported cymene-Ru transfer hydrogenation catalysts. R=$^i$Pr or $^s$Bu.
Figure 7:
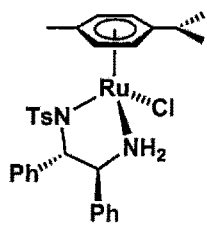
Figure 7:
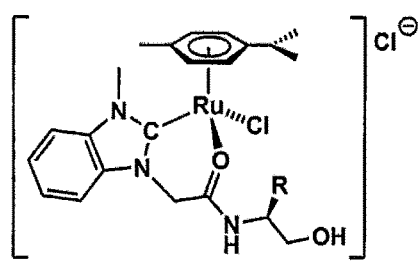
Figure 7:
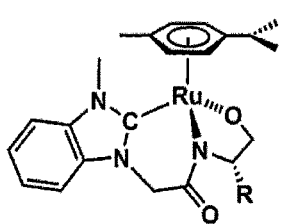

Homogenous hydrogenation catalysis was first demonstrated with a cymene-ruthenium complex in 1978, with the dicationic metallocene IIIc producing cyclohexane from cyclohexene under 50 bar of H$_2$(g) (FIG. 7) [41]. Noyori demonstrated that arene-ruthenium complexes could catalyze the transfer hydrogenation of achiral ketones, using $^i$PrOH as the H$_2$ source, into chiral alcohols with excellent enantioselectivity (e.g. IIId) [42]. Considering the other chelating carboxylate NHC-supported complexes, IIIa achieved near-quantitative hydrogenation of styrene to ethylbenzene in $^i$PrOH, but the reactions required 60 bar of H$_2$(g) to proceed and exhibited no conversion at lower pressures (e.g. 1 bar) [17a]. Complex IIIb, on the other hand, could convert acetophenone to 1-phenylethanol using $^i$PrOH as the solvent and H$_2$ source, but the authors noted the catalyst displayed inconsistent activity and IIIb was only obtained as a byproduct from the synthesis of a different complex. The closest analog of Ru1 with a chelating benzimidazolylidene that catalyzes transfer hydrogenation of acetophenone using $^i$PrOH as the H$_2$ source is IIIe, which comprises a neutral chelating benzimidazolylidene that can be deprotonated in situ to afford a complex with an anionic chelating NHC ligand (IIIf) under the basic conditions employed for transfer hydrogenation catalysis [43]. Although complex IIIe exhibited modest activity (19% yield after 20 h) and enantiomeric excess (33%) of (S)-1-phenylethanol, independently prepared and isolated IIIf showed no catalytic activity, even though the reactions with IIIe were performed in the presence of excess base (7.5 equiv.) to deprotonate the ligand.

The ability of Ru1 to catalyze transfer hydrogenation reactions and the factors influencing its activity using the conversion of acetophenone (4a) to 1-phenylethanol (5a) in $^i$PrOH as the benchmark reaction was explored. Near-quantitative isolated yield (96%) of 5a was obtained after 24 h at 83° C. using 1 mol % Ru1 with 5 mol % KO$^t$Bu, corresponding to a turnover number (TON) of 96 (entry 1, Table 3). 1 mol % catalyst and 5 mol % KOtBu were selected as the standardized conditions for all subsequent transfer hydrogenation reactions using Ru1 as the catalyst. Analysis of the 4a→5a reaction mixture after 1 h by $^1$H NMR spectroscopy revealed a turnover frequency (TOF) of 31 h$^{-1}$. Product formation was observed to be linear with respect to time for the first 2 h of all substrate hydrogenation reactions investigated. Repeating the 4a→5a reaction without Ru1 afforded only 6% of 5a. Conversely, when 5a was treated with 1 mol % Ru1 and 5 mol % KO$^t$Bu in toluene at 83° C. for 24 h, the dehydrogenation product 4a was formed in 50% isolated yield.

TABLE 3

Summary of transfer hydrogenation reactions catalyzed by 3 $^a$

| Entry | Substrate | Product | Yield (%) $^b$ | TON $^c$ | TOF (h$^{-1}$) $^d$ |
|---|---|---|---|---|---|
| 1 | O⃫Ph (4a) | OH-Ph (5a) | 96 | 96 | 31 |
| 2 | O⃫C$_7$H$_{15}$ | OH-C$_7$H$_{15}$ | 95 | 95 | 25 |

TABLE 3-continued

Summary of transfer hydrogenation reactions catalyzed by 3 [a]

| Entry | Substrate | Product | Yield (%) [b] | TON [c] | TOF (h$^{-1}$) [d] |
|---|---|---|---|---|---|
| 3 | 4b (cyclohexanone) | 5b (cyclohexanol) | 98 | 98 | 59 |
| 4 | 4c (Ph-CH=CH-C(O)-Ph, chalcone) | 5c (Ph-CH$_2$-CH$_2$-CH(OH)-Ph) | 86 | 86 | 27, [e] 8.2 [f] |
| 5 | 4d (Ph-CH=NPh) | 5d (Ph-CH$_2$-NHPh) | 82 | 82 | 8.1 |

[a] Reaction conditions:
0.91 mmol substrate, 9.1 μmol Ru1, 45 μmol KO$^t$Bu, 5 mL $^i$PrOH, 83° C., 24 h.
[b] Isolated yield of pure product, averaged over 2 runs.
[c] Turnover number (TON) = (mmol of 5)/(mmol of Ru1).
[d] Turnover frequency (TOF) determined by $^1$H NMR spectroscopic analysis of reaction mixture after 1 h.
[e] Values correspond to TOF for hydrogenation of the C=C bond in 4d followed by
[f] the C=O bond in 1,3-diphenylpropan-1-one.

Transfer hydrogenation catalysis has been investigated with the 4a→5a reaction for other NHC-supported arene-ruthenium complexes under conditions comparable to those used for Ru1 (≤1 mol % catalyst, substoichiometric base, $^i$PrOH solvent, temperatures ≥75° C.) from which a wide range of TON (34-1056) and TOF (4.1-1012 h$^{-1}$) values [44] have been observed [31, 37a, 42]. Although the TON and TOF values for Ru1 (96 and 31 h$^{-1}$, respectively) are at the lower ends of the ranges measured for all reported cymene-Ru—NHC transfer hydrogenation catalysts, they compare favorably to IIIa (no activity with H$_2$(g)<60 bar) [17a], IIIb (inconsistent activity) [32], and IIIe (TON=4.8, TOF=0.24 h$^{-1}$) [43]. Thus, despite the fact that replacing the imidazolylidene scaffold in IIIa and IIIb with the benzimidazolylidene scaffold in Ru1 does not produce significant variation in metric parameters, Ru1 achieves catalytic transfer hydrogenation with reproducible TON and TOF values using $^i$PrOH as the sole H$_2$ source, but IIIa and IIIb do not. Markedly different chemical reactivity between complexes supported by benzimidazolylidene- vs imidazolylidene ligands has been observed with Grubbs' catalysts, in which benzimidazolylidene-supported complexes were unstable with respect to ligand decomposition under conditions in which the imidazolylidene-supported complexes would be stable [45].

The scope of substrates which could undergo transfer hydrogenation by Ru1 using the standardized conditions was examined. Similar to 4a→5a, 2-nonanone (4b) and cyclohexanone (4c) were converted to 2-nonanol (5b) and cyclohexanol (5c) in near-quantitative isolated yields (TON=95 and 98, respectively; entries 2 and 3, Table 3). In contrast, the TOF for 4b→5b (25 h$^{-1}$) was slightly slower than for 4a→5a and the TOF for 4c→5c (59 h$^{-1}$) was significantly faster. Steric effects between the substrate and catalyst could affect the transition state energy and produce variation in TOF values. For example, 4a and 4b differ by the replacement of a phenyl with an n-heptyl group, a flexible n-alkyl chain that occupies a greater volume due to free rotation than a rigid aryl ring and will thus cause greater substrate-catalyst steric repulsion than 4a. Flexibility is significantly reduced if alkyl substituents are tied together in a cycloalkane ring, and diminished steric congestion likely contributes to the faster reactivity of 4c vs. 4b.

Using chalcone (4d; entry 4, Table 3) as an α,β-unsaturated ketone substrate with Ru1, the fully-saturated product 1,3-diphenyl-propan-1-ol (5d) was obtained in good yield (TON=86), wherein $^1$H NMR analysis revealed hydrogenation occurred at the alkene moiety before the ketone. For the first 2 h, the only observable product was 1,3-diphenylpropan-1-one (from hydrogenation of the C=C bond in 4d), and its formation was linear with respect to time over the first 2 h (TOF=27 h$^{-1}$). After 2 h, 5d began to appear (from hydrogenation of the C=O bond in 1,3-diphenylpropan-1-one), and its formation was linear with respect to time over the next 2 h (TOF=8.2 h$^{-1}$). After 24 h, the only observable product was 5d, which was isolated and used to determine TON. No formation of 1,3-diphenylprop-2-en-1-ol (from hydrogenation of the C=O bond in 4d) was observed during the course of the reaction. Other NHC-supported arene-ruthenium transfer hydrogenation catalysts have exhibited similar preferential reactivity at the carbon-carbon double bonds in α,β-unsaturated ketones [40e, 40k, 46], which has been proposed as evidence for an inner-sphere mechanism being operative in these systems [47]. No hydrogenation of stilbene was observed with Ru1, which suggests that polarization of the C=C bond (e.g. by the adjacent carbonyl in 4d) is necessary for reactivity. Substituting a ketone with an imine substrate (4e, entry 5) resulted in a lower yield of hydrogenated product 5e (TON=82) and significantly slower formation (TOF=8.1 h$^{-1}$), behavior which is consistent with the slower overall reactivity observed for NHC-supported arene-ruthenium complexes with similar imine substrates (e.g., for 4e, TOF=2.0-33 h$^{-1}$) [40e, 48]. Presumably, the trend of lower TOF values for imines vs. ketones arises from the less polar character of a C=N bond relative to a C=O bond.

We have reported a chelating benzimidazolylidene carboxylate ligand (1$^-$) that can be accessed via the benzimidazolium hydrobromide precursor [1H$_2$][Br]. Deprotonation and metallation with Ag$_2$O produced the silver-NHC complex 2, which was revealed by X-ray crystallography to exist in the solid state as a dodecametallic cyclic species comprising mononuclear [Ag(1)] and dinuclear [Ag$_2$(1)$_2$] subunits. Despite this multinuclear structure, transmetallation of 1$^-$ from 2 to [RuCl(cymene)(μ-Cl)]$_2$ proceeded smoothly with precipitation of AgCl to afford analytically pure ruthenium-NHC complex Ru1 in near-quantitative yield.

Complex Ru1 functions as a precatalyst in the transfer hydrogenation of unsaturated substrates using $^i$PrOH as the H$_2$ source. Benzylic, alkyl and cycloalkyl ketones were converted to their corresponding alcohols in excellent yields (TON=95-98) and at modest rates (TOF=25-59 h$^{-1}$). Chalcone, an α,β-unsaturated ketone, underwent reduction faster at the alkene moiety (TOF=27 h$^{-1}$) than at the carbonyl (TOF=8.2 h$^{-1}$), ultimately affording the fully-saturated 1,3-diphenylpropan-1-ol in high yield (TON=86). Similarly, Ru1 was catalytically competent for the hydrogenation of an imine substrate, albeit with diminished reactivity (TON=82, TOF=8.1 h$^{-1}$) relative to the ketone substrates.

1$^-$ can substitute an X-type ligand on a transition metal as well as coordinate in a bidentate manner with both the NHC and carboxylate moieties. Due to the anionic nature of 1$^-$, this ligand exchange can be accomplished without altering the overall charge of the complex. Given that the transfer of 1$^-$ from 2 to another transition metal can afford analytically pure Ru1 in near-quantitative yields without the need for purification, this may serve as a general strategy to access diverse families of transition metal complexes for a wide variety of applications.

REFERENCES

[1] H.-W. Wanzlick, H.-J. Schönherr, Angew. Chem. Int. Ed. 7 (1968) 141.
[2] K. Öfele, J. Organomet. Chem. 12 (1968) P42.
[3] H. W. Wanzlick, F. Esser, H. J. Kleiner, Chem. Ber. 96 (1963) 1208.
[4] A. J. Arduengo, III, R. L. Harlow, M. Kline, J. Am. Chem. Soc. 113 (1991) 361.
[5] (a) F. Glorius, Topics Organomet. Chem. 21 (2007) 1; (b) E. Peris, R. H. Crabtree, Coord. Chem. Rev. 248 (2004) 2239; (c) W. A. Herrmann, Angew. Chem. Int. Ed. 41 (2002) 1290.
[6] (a) R. Visbal, M. C. Gimeno, Chem. Soc. Rev. 43 (2014) 3551; (b) W.-C. Chang, H.-S. Chen, T.-Y. Li, N.-M. Hsu, Y. S. Tingare, C.-Y. Li, Y.-C. Liu, C. Su, W.-R. Li, Angew. Chem. Int. Ed. 49 (2010) 8161; (c) H.-J. Park, K. H. Kim, S. Y. Choi, H.-M. Kim, W. I. Lee, Y. K. Kang, Y. K. Chung, Inorg. Chem. 49 (2010) 7340.
[7] (a) O. R. Luca, D. L. Huang, M. K. Takase, R. H. Crabtree, New J. Chem. 37 (2013) 3402; (b) P. M. Zimmerman, A. Paul, Z. Zhang, C. B. Musgrave, Angew. Chem. Int. Ed. 48 (2009) 2201; (c) R. J. Keaton, J. M. Blacquiere, R. T. Baker, J. Am. Chem. Soc. 129 (2007) 1844.
[8] P. V. Simpson, C. Schmidt, I. Ott, H. Bruhn, U. Schatzschneider, Eur. J. Inorg. Chem. (2013) 5547.
[9] (a) F. E. Hahn, M. C. Jahnke, Angew. Chem. Int. Ed. 47 (2008) 3122; (b) L. Cavallo, A. Correa, C. Costabile, H. Jacobsen, J. Organomet. Chem. 690 (2005) 5407; (c) R. H. Crabtree, J. Organomet. Chem. 690 (2005) 5451.
[10] M.-T. Lee, C.-H. Hu, Organometallics 23 (2004) 976.
[11] Y. Yan, C. Keating, P. Chandrasekaran, U. Jayarathne, J. T. Mague, S. DeBeer, K. M. Lancaster, S. Sproules, I. V. Rubtsov, J. P. Donahue, Inorg. Chem. 52 (2013) 6743.
[12] R. Dorta, E. D. Stevens, N. M. Scott, C. Costabile, L. Cavallo, C. D. Hoff, S. P. Nolan, J. Am. Chem. Soc. 127 (2005) 2485.
[13] (a) L.-H. Chung, K.-S. Cho, J. England, S.-C. Chan, K. Wieghardt, C.-Y. Wong, Inorg. Chem. 52 (2013) 9885; (b) D. T. Plummer, R. J. Angelici, Inorg. Chem. 22 (1983) 4063; (c) P. M. Treichel, H. J. Mueh, J. Organomet. Chem. 122 (1976) 229.
[14] (a) V. Sivakumar, M. Nethaji, B. R. Jagirdar, N. Mathew, Synth. React. Inorg. Met.-Org. Nano-Met. Chem. 37 (2007) 677; (b) C. Bo, R. Fandos, M. Feliz, C. Hernández, A. Otero, A. Rodríguez, M.a. J. Ruiz, C. Pastor, Organometallics 25 (2006) 3336; (c) R. W. Johnson, R. H. Holm, J. Am. Chem. Soc. 100 (1978) 5338.
[15] (a) N. C. Tomson, J. Arnold, R. G. Bergman, Dalton Trans. 40 (2011) 7718; (b) M. J. Ferreira, I. Matos, J. R. Ascenso, M. T. Duarte, M. M. Marques, C. Wilson, A. M. Martins, Organometallics 26 (2007) 119; (c) G. S. Hair, R. A. Jones, A. H. Cowley, V. Lynch, Organometallics 20 (2001) 177; (d) J. I. Amor, T. Cuenca, M. Galakhov, P. Gómez-Sal, A. Manzanero, P. Royo, J. Organomet. Chem. 535 (1997) 155; (e) B. E. Bosch, G. Erker, R. Fröhlich, O. Meyer, Organometallics 25 (1997) 5449; (f) L. Lee, D. J. Berg, G. W. Bushnell, Organometallics 16 (1997) 2556; (g) B. Temme, G. Erker, R. Fröhlich, M. Grehl, Angew. Chem. Int. Ed. 33 (1994) 1480.
[16] C. Eaborn, N. Farrell, J. L. Murphy, A. Pidcock, J. Chem. Soc., Dalton Trans. (1976) 58.
[17] (a) C. Gandolfi, M. Heckenroth, A. Neels, G. Laurenczy, M. Albrecht, Organometallics 28 (2009) 5112; (b) Y. Lee, B. Li, A. H. Hoveyda, J. Am. Chem. Soc. 131 (2009) 11625; (c) A. A. Danopoulos, P. Cole, S. P. Downing, D. Pugh, J. Organomet. Chem. 693 (2008) 3369.
[18] (a) F. Meng, H. Jang, A. H. Hoveyda, Chem. Eur. J. 19 (2013) 3204; (b) B. Jung, A. H. Hoveyda, J. Am. Chem. Soc. 134 (2012) 1490; (c) X. Zhou, R. F. Jordan, Organometallics 30 (2011) 4632; (d) F. Gao, K. P. McGrath, Y. Lee, A. H. Hoveyda, J. Am. Chem. Soc. 132 (2010) 14315; (e) Y. Nagai, T. Kochi, K. Nozaki, Organometallics 28 (2009) 6131; (f) M. K. Brown, T. L. May, C. A. Baxter, A. H. Hoveyda, Angew. Chem. Int. Ed. 46 (2007) 1097.
[19] (a) R. H. Crabtree, Coord. Chem. Rev. 257 (2013) 755; (b) P. L. Arnold, S. Pearson, Coord. Chem. Rev. 251 (2007) 596.
[20] T. Guo, S. Dechert, F. Meyer, Organometallics 33 (2014) 5145.
[21] E. J. Hanan, B. K. Chan, A. A. Estrada, D. G. Shore, J. P. Lyssikatos, Synlett (2010) 2759.
[22] G. R. Fulmer, A. J. M. Miller, N. H. Sherden, H. E. Gottlieb, A. Nudelman, B. M. Stoltz, J. E. Bercaw, K. I. Goldberg, Organometallics 29 (2010) 2176.
[23] CrystalClear, in, Rigaku/MSC, The Woodlands, Tex., 2009.
[24] REQAB, in, Rigaku Corporation, Tokyo, Japan, 1998.
[25] (a) G. M. Sheldrick, Acta Cryst. A 64 (2008) 112; (b) G. M. Sheldrick, SHELXTL00: Program for Refinement of Crystal Structures, in: SHELXTL00: Program for Refinement of Crystal Structures, University of Göttingen, Göttingen, Germany, 2000.
[26] (a) A. L. Spek, Acta Cryst. D 65 (2009) 148; (b) A. L. Spek, PLATON, A Multipurpose Crystallographic Tool, in, Utrecht University, Utrecht, The Netherlands, 2000.
[27] C. Lohre, T. Dröge, C. Wang, F. Glorius, Chem. Eur. J. 17 (2011) 6052.
[28] I. J. B. Lin, C. S. Vasam, Coord. Chem. Rev. 251 (2007) 642.
[29] M. G. Boswell, F. G. Yeung, C. Wolf, Synlett 23 (2012) 1240.
[30] (a) F. Hackenberg, G. Lally, H. Müller-Bunz, F. Paradisi, D. Quaglia, W. Streciwilk, M. Tacke, J. Organomet. Chem. 717 (2012) 123; (b) W. J. Humenny, S. Mitzinger, C. B. Khadka, B. K. Najafabadi, I. Vieira, J. F. Corrigan, Dalton Trans. 41 (2012) 4413; (c) S. Patil, A. Deally, B. Gleeson, H. Müller-Bunz, F. Paradisi, M. Tacke, Metallomics 3 (2011) 74; (d) S. Patil, A. Deally, B. Gleeson, F. Hackenberg, H. Müller-Bunz, F. Paradisi, M. Tacke, Z. Anorg. Allg. Chem. 637 (2011) 386; (e) S. Patil, J. Claffey, A. Deally, M. Hogan, B. Gleeson, L. M. M. Méndez, H. Müller-Bunz, F. Paradisi, M. Tacke, Eur. J. Inorg. Chem. (2010) 1020; (f) S. Patil, A. Deally, B. Gleeson, H. Müller-Bunz, F. Paradisi, M. Tacke, Appl. Organomet. Chem. 24 (2010) 781; (g) S. Patil, K. Dietrich, A. Deally, B. Gleeson, H. Müller-Bunz, F. Paradisi, M. Tacke, Helv. Chim. Acta 93 (2010) 2347.
[31] L. R. Moore, S. M. Cooks, M. S. Anderson, H.-J. Schanz, S. T. Griffin, R. D. Rogers, M. C. Kirk, K. H. Shaughnessy, Organometallics 25 (2006) 5151.
[32] J. DePasquale, N. J. White, E. J. Ennis, M. Zeller, J. P. Foley, E. T. Papish, Polyhedron 58 (2013) 162.
[33] (a) S. Demir, I. Özdemir, O. Şahin, B. Çetinkaya, O. Büyükgüngör, Synlett (2010) 496; (b) H. Arslan, D. VanDerveer, İ. Özdemir, S. Demir, B. Çetinkaya, Acta Cryst. E 65 (2009) m97; (c) H. Arslan, D. VanDerveer, S. Yaşar, İ. Özdemir, B. Çetinkaya, Acta Cryst. E 65 (2009) m243; (d) S. H. Hong, A. Chlenov, M. W. Day, R. H. Grubbs, Angew. Chem. Int. Ed. 46 (2007) 5148.
[34] (a) C. Ma, J. Li, J. Peng, Y. Bai, G. Zhang, W. Xiao, G. Lai, J. Organomet. Chem. 727 (2013) 28; (b) X. Xuan, N. Wang, Z. Xue, Spectrochim. Acta A 96 (2012) 436; (c) N. N. Al-Mohammed, Y. Alias, Z. Abdullah, H. Khaledi, Acta Cryst. E 67 (2011) o1701; (d) J. C. Y. Lin, C.-J. Huang, Y.-T. Lee, K.-M. Lee, I. J. B. Lin, J. Mater. Chem. 21 (2011) 8110; (e) P. Nockemann, B. Thijs, T. N. Parac-Vogt, K. V. Hecke, L. V. Meervelt, B. Tinant, I. Hartenbach, T. Schleid, V. T. Ngan, M. T. Nguyen, K. Binnemans, Inorg. Chem. 47 (2008) 9987.
[35] (a) Y. Li, X. Chen, Y. Song, L. Fang, G. Zou, Dalton Trans. 40 (2011) 2046; (b) C. K. Lee, C. S. Vasam, T. W. Huang, H. M. J. Wang, R. Y. Yang, C. S. Lee, I. J. B. Lin, Organometallics 25 (2006) 3768; (c) C. Y. Legault, C. Kendall, A. B. Charette, Chem. Commun. (2005) 3826; (d) P.d. Frémont, N. M. Scott, E. D. Stevens, T. Ramnial, O. C. Lightbody, C. L. B. Macdonald, J. A. C. Clyburne, C. D. Abernethy, S. P. Nolan, Organometallics 24 (2005) 6301.
[36] (a) L. Ray, M. M. Shaikh, P. Ghosh, Inorg. Chem. 47 (2008) 230; (b) J. El-Bahraoui, J. M. Molina, D. P. Olea, J. Phys. Chem. A 102 (1998) 2443; (c) P. Pyykkö, Chem. Rev. 97 (1997) 597; (d) K. Singh, J. R. Long, P. Stavropoulos, J. Am. Chem. Soc. 119 (1997) 2942.
[37] C. Janiak, J. Chem. Soc., Dalton Trans. (2000) 3885.
[38] (a) Y. Li, L. Yang, Q. Chen, C. Cao, P. Guan, G. Pang, Y. Shi, Z. Anorg. Allg. Chem. 639 (2013) 575; (b) M. C. Gimeno, A. Laguna, R. Visbal, Organometallics 31 (2012) 7146; (c) G. Huang, H. Sun, X. Qiu, Y. Shen, J. Jiang, L. Wang, J. Organomet. Chem. 696 (2011) 2949; (d) Q.-X. Liu, X.-Q. Yang, X.-J. Zhao, S.-S. Ge, S.-W. Liu, Y. Zang, H.-b. Song, J.-H. Guo, X.-G. Wang, CrystEngComm 12 (2010) 2245; (e) Q.-X. Liu, S.-J. Li, X.-J. Zhao, Y. Zang, H.-b. Song, J.-H. Guo, X.-G. Wang, Eur. J. Inorg. Chem. (2010) 983; (f) Q.-X. Liu, X.-J. Zhao, X.-M. Wu, L.-N. Yin, J.-H. Guo, X.-G. Wang, J.-C. Feng, Inorg. Chim. Acta 361 (2008) 2616; (g) Q.-X. Liu, L.-N. Yin, X.-M. Wu, J.-C. Feng, J.-H. Guo, H.-B. Song, Polyhedron 27 (2008) 87; (h) Q.-X. Liu, L.-N. Yin, J.-C. Feng, J. Organomet. Chem. 692 (2007) 3655; (i) P. de Frémont, N. M. Scott, E. D. Stevens, S. P. Nolan, Organometallics 24 (2005) 2411.
[39] (a) G. Türkoglu, S. Tampier, F. Strinitz, F. W. Heinemann, E. Hübner, N. Burzlaff, Organometallics 31 (2012) 2166; (b) G. Türkoglu, F. W. Heinemann, N. Burzlaff, Dalton Trans. 40 (2011) 4678; (c) E. Hübner, N. V. Fischer, F. W. Heinemann, U. Mitra, V. Dremov, P. Müller, N. Burzlaff, Eur. J. Inorg. Chem. (2010) 4100; (d) J.-H. Oh, T. Nishioka, R. Masui, E. Asato, I. Kinoshita, S. Takara, Polyhedron 29 (2010) 1964; (e) G. Türkoglu, C. P. Ulldemolins, R. Müller, E. Hübner, F. W. Heinemann, M. Wolf, N. Burzlaff, Eur. J. Inorg. Chem. (2010) 2962; (f) F. Marchetti, C. Pettinari, A. Cerquetella, A. Cingolani, R. Pettinari, M. Monari, R. Wanke, M. L. Kuznetsov, A. J. L. Pombeiro, Inorg. Chem. 48 (2009) 6096; (g) S. Tampier, R. Müller, A. Thorn, E. Hübner, N. Burzlaff, Inorg. Chem. 47 (2008) 9624; (h) R. Müller, E. Hübner, N. Burzlaff, Eur. J. Inorg. Chem. (2004) 2151; (i) P. Štěpnička, New J. Chem. (2002) 567.
[40] (a) J. DePasquale, M. Kumar, M. Zeller, E. T. Papish, Organometallics 32 (2013) 966; (b) D. Jantke, M. Cokoja, A. Pöthig, W. A. Herrmann, F. E. Kühn, Organometallics 32 (2013) 741; (c) N. Gürbüz, E. Ö. Özcan, İ. Özdemir, B. Çetinkaya, O. Şahin, O. Büyükgüngör, Dalton Trans. 41 (2012) 2330; (d) A. Monney, G. Venkatachalam, M. Albrecht, Dalton Trans. 40 (2011) 2716; (e) S. Horn, C. Gandolfi, M. Albrecht, Eur. J. Inorg. Chem. (2011) 2863; (f) M. Würtemberger, T. Ott, C. Döring, T. Schaub, U. Radius, Eur. J. Inorg. Chem. (2011) 405; (g) Y. Zhang, C. Chen, S. C. Ghosh, Y. Li, S. H. Hong, Organometallics 29 (2010) 1374; (h) C. Zhang, Y. Zhao, B. Li, H. Song, S. Xua, B. Wang, Dalton Trans. (2009) 5182; (i) X. Wang, S. Liu, L.-H. Weng, G.-X. Jin, Chem. Eur. J. 13 (2007) 188; (j) R. Cariou, C. Fischmeister, L. Toupet, P. H. Dixneuf, Organometallics 25 (2006) 2126; (k) P. Csabai, F. Joó, Organometallics 23 (2004) 5640; (l) F. Simal, D. Jan, L. Delaude, A. Demonceau, M.-R. Spirlet, A. F. Noels, Can. J. Chem. 79 (2001) 529.
[41] M. J. H. Russell, C. White, A. Yates, P. M. Maitlis, J. Chem. Soc., Dalton Trans. (1978) 857.
[42] S. Hashiguchi, A. Fujii, J. Takehara, T. Ikariya, R. Noyori, J. Am. Chem. Soc. 117 (1995) 7562.
[43] M. Yoshimura, R. Kamisue, S. Sakaguchi, J. Organomet. Chem. 740 (2013) 26.
[44] For previous studies that did not explicitly report them.
[45] (a) J. M. Berlin, K. Campbell, T. Ritter, T. W. Funk, A. Chlenov, R. H. Grubbs, Org. Lett. 9 (2007) 1339; (b) A. Poater, N. Bahri-Laleh, L. Cavallo, Chem. Commun. (2011) 6674; (c) Y. Borguet, G. Zaragoza, A. Demonceau, L. Delaude, Dalton Trans. 42 (2013) 7287.
[46] (a) H. Ohara, W. W. N. O, A. J. Lough, R. H. Morris, Dalton Trans. 41 (2012) 8797; (b) A. Azua, J. A. Mata, E. Peris, Organometallics 30 (2011) 5532; (c) W. W. N. O, A.

J. Lough, R. H. Morris, Organometallics 30 (2011) 1236; (d) M. Fekete, F. Joó, Collect. Czech. Chem. Commun. 72 (2007) 1073.

[47] S. E. Clapham, A. Hadzovic, R. H. Morris, Coord. Chem. Rev. 248 (2004) 2201.

[48] (a) F. E. Fernández, M. C. Puerta, P. Valerga, Organometallics 31 (2012) 6868; (b) X.-Q. Guo, Y.-N. Wang, D. Wang, L.-H. Cai, Z.-X. Chen, X.-F. Hou, Dalton Trans. 41 (2012) 14557.

Example 2

A chelating benzimidazolylidene-carboxylate ligand (1$^-$) was transferred from 2 to [RuCl$_2$(dmso)$_4$] to afford trans (C)—[Ru(1)$_2$(bpy)] (Ru3), but all attempts to incorporate 1 into cis(Cl)—[RuCl$_2$(bpy)$_2$] were unsuccessful. Alternatively, reaction of [RuCl(1)($\eta^6$-cymene)] (Ru1) with bpy and AgOTf successfully produced [Ru(1)(bpy)$_2$][OTf] (Ru4). Methylation of Ru3 and Ru4 with MeOTf yielded trans(C)—[Ru(1-Me)$_2$(bpy)][OTf]$_2$ (Ru3.2MeOTf) and [Ru(1-Me)(bpy)$_2$][OTf]$_2$ (Ru4.MeOTf), accompanied by a +2 and +1 increase in net charge, respectively. Cyclic voltammetry indicated that the increase in Ru(II)/Ru(III) oxidation potential from Ru3 to Ru3.2MeOTf was twice the increase from 4 to Ru4.MeOTf. UV-visible spectroscopy also revealed that transitions in Ru3.2MeOTf occurred at higher energy than in 2 by double the difference between Ru4.MeOTf and 4. Crystallographic analysis demonstrated that the coordination environment of Ru did not differ significantly between 2 and Ru3.2MeOTf, suggesting that the observed shifts in oxidation potentials and absorption wavelengths are not due to changes in coordination chemistry or formal oxidation state. Collectively, these results show that Ru3.2MeOTf and Ru4.MeOTf feature Ru centers more electron deficient than those in 2 and 4, respectively, by amounts proportional to the difference in net charge.

The strategy was to prepare octahedral ruthenium complexes [RuL$_n$(NHC)]$^{m+}$ (A) comprising one or more benzimidazolylidene-carboxylate ligands (Scheme 3). Coordinative saturation was desired to minimize any variation in electron density at the metal due to changes in coordination number or ligand substitution. Conversion of A to [RuL$_n$(NHC-Me)]$^{(m+1)+}$ (B) via methylation was expected to transform the L,X-type NHC-carboxylate into an L$_2$-type chelating NHC-ester. Although this reaction at the ligand would be accompanied a +1 increase in net charge for the complex, the formal oxidation state of Ru in B would not change. Spectroscopic, crystallographic and electrochemical analysis and comparison of complexes A and B would then elucidate the impact of increasing the net charge on a complex separately from any increase in oxidation state of the metal center.

Scheme 3: Methylation of [RuL$_n$(NHC)]$^{m+}$

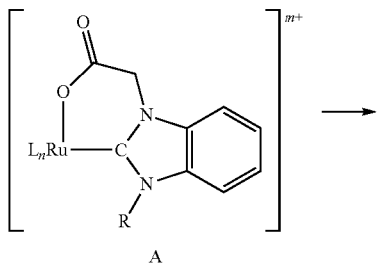

A

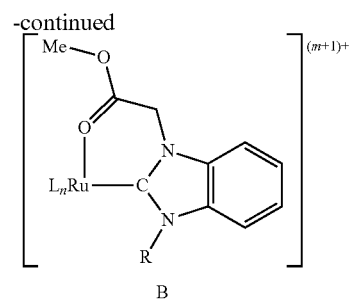

B (A) will afford [RuL$_n$(NHC—Me)]$^{(m+1)+}$(B), with a +1 increase in net charge but no change in Ru oxidation state.

Materials and Methods

Complex 2, Ru1 and [RuCl$_2$(bpy)(dmso)$_2$] were prepared as previously described [6, 8]. All other materials and solvents were of reagent quality and used as received. $^1$H and $^{13}$C{$^1$H} NMR spectra were recorded using a Bruker 500 MHz spectrometer. Chemical shifts δ (in ppm) for $^1$H and $^{13}$C NMR are referenced to SiMe$_4$ using the residual protio-solvent as an internal standard [9]. For $^1$H NMR: CDCl$_3$, 7.26 ppm; acetone-d$_6$, 2.05 ppm. For $^{13}$C NMR: CDCl$_3$, 77.16 ppm. Coupling constants (J) are expressed in hertz (Hz). Infrared spectra were recorded with 4 cm$^{-1}$ resolution on a Shimadzu IRAffinity-1S spectrometer equipped with a Pike Technologies MIRacle ATR sampling accessory (diamond crystal). Elemental analyses were performed at Atlantic Microlab, Inc. (Norcross, Ga.). All reactions were performed under an inert atmosphere were performed under an N$_2$ atmosphere using standard Schlenk or glovebox techniques with the exclusion of light. All workups and purifications were performed under ambient conditions using standard benchtop techniques without requiring exclusion of light. When required, solvents were dried and deoxygenated using an Innovative Technologies solvent purification system, and then stored over molecular sieves (3 Å) in a drybox.

General Spectroscopic Considerations

UV-visible absorption spectra were acquired on a Varian Cary 50 Bio spectrometer equipped with a Quantum Northwest TC-125 temperature controller. Room temperature solutions measurements were performed in matched gas-tight quartz cuvettes (Precision Scientific) with 1 cm path lengths and 3.0 mL analyte solution volumes thermostatted at 25° C. Absorption spectra were acquired in CH$_2$Cl$_2$ under an N$_2$ atmosphere for all analytes. Extinction coefficients (ε) were calculated from Beer's law measurements using 10, 20, 30 and 40 μM analyte concentrations.

Electrochemistry

Electrochemical experiments were conducted on CH Instruments Electrochemical Workstations (series 660D) using a gastight, three-electrode cell under an atmosphere of dry nitrogen. The cell was equipped with gold working and tungsten counter electrodes, as well as a silver wire quasi-reference electrode. Unless specified otherwise, measurements were performed using 1.0 mM solutions of analyte in dry CH$_2$Cl$_2$ with 0.10 M [tetra-n-butyl-ammonium][PF$_6$] as the electrolyte and 1.0 mM ferrocene (Fc) as the internal standard. All potentials reported were determined by cyclic voltammetry at 100 mV s$^{-1}$ scan rates and referenced to ferrocene by shifting (Fc)$^{0/+}$ to 0.00 V (CH$_2$Cl$_2$).

X-Ray Crystallographic Studies

Single crystals of Ru3 and Ru4 were immersed in Paratone-N oil at room temperature and mounted on glass fibers using epoxy glue. The samples were then mounted on the goniometer for data collection at 200 K under a stream of cold nitrogen. Intensity data were collected using Mo Kα radiation (λ=0.71073 Å) and a Mercury CCD detector with a Rigaku AFC8S diffractometer controlled using the CrystalClear software package [10]. The crystal-to-detector distance was 27 mm. Data were collected using ω-scans (0.5° oscillations) using 65 s exposures for Ru3 and 20 s exposures for Ru4. Data were corrected for absorption, Lorentz, and polarization effects using the REQAB subroutine of CrystalClear [11]. The structures were solved by direct methods and subsequently refined using the SHELXTL software package [12]. Further evaluation for higher symmetry and solvent occupancy was done using the PLATON program suite [13]. All non-hydrogen atoms were refined anisotropically. Hydrogen atoms were placed at calculated positions using a riding model and assigned thermal parameters equal to either 1.5 (methyl hydrogen atoms) or 1.2 (non-methyl hydrogen atoms) times the thermal parameters of the atoms to which they were attached. For Ru3, the ethanol and water solvent molecules were identified from the difference map and modeled by the judicious use of restraints. For Ru4, several partially-occupied acetone solvent molecules could initially be identified from the difference map, but their refinement proved problematic, even when heavily restrained. These disordered solvent molecules were instead modeled using the SQUEEZE tool of PLATON.

Synthesis of trans(C)—[Ru(1)$_2$(bpy)] (Ru3)

Complex 2 (323 mg, 0.83 mmol) was dissolved in CHCl$_3$ (10 mL) and to this solution was added dropwise a solution of [RuCl$_2$(bpy)(dmso)$_2$] (200 mg, 0.41 mmol, 0.5 equiv.) in CHCl$_3$ (10 mL) and the mixture was then heated to reflux. After 24 h, the reaction mixture was allowed to cool to room temperature and was then filtered through a 0.2 μm PTFE filter (to remove AgCl) with the aid of CHCl$_3$ (4 mL). The filtrate solvent was removed under reduced pressure and the resulting solids were then dissolved in minimum CH$_2$Cl$_2$ and added to 10 mL of hexanes resulting in the formation of a precipitate. The solids were collected via centrifugation, washed with Et$_2$O (3×10 mL) and MeOH (3×10 mL), and then dried in vacuo to afford 262 mg (0.32 mmol, 78% yield) of the desired product as a dark red-purple solid. $^1$H NMR (500 MHz, CDCl$_3$): δ=8.98 (d, J=5.5, 2H), 7.37 (d, J=8.5, 2H), 7.26-7.24 (m, 2H), 7.18 (t, J$_1$=8.0, J$_2$=15.5, 2H), 6.99-6.92 (m, 4H), 6.76 (d, J=8.0, 2H), 6.70 (s, 2H), 6.28 (d, J=8.0, 2H), 6.17 (s, 2H), 5.44 (s, 2H), 5.28 (d, J=16.0, 2H), 5.08 (d, J=15.5, 2H), 1.99 (s, 6H), 1.90 (s, 6H). $^{13}$C NMR (125 MHz, CDCl$_3$): δ 198.3, 174.7, 160.0, 152.2, 138.9, 137.6, 137.4, 136.7, 134.6, 130.2, 129.2, 126.1, 125.4, 122.9, 122.8, 122.3, 120.8, 109.7, 109.2, 50.5, 21.2, 21.2. FT-IR (ATR, diamond): UV-vis (CH$_2$Cl$_2$), λ (ϵ) in nm (M$^{-1}$ cm$^{-1}$): 293 (sh, 2.05×10$^4$), 302 (2.59×10$^4$), 386 (3.57×10$^4$), 499 (4.07×10$^3$), 530 (5.46×10$^3$). Anal. Calc. for C$_{44}$H$_{39}$N$_6$O$_{4.5}$Ru (2.0.5H$_2$O): C, 64.07; H, 4.77; N, 10.19. Found: C, 63.94; H, 4.84; N, 10.18.

Synthesis of [Ru(1)(bpy)$_2$][OTf] (Ru4)

Complex Ru1 (100 mg, 0.18 mmol) and 2,2'-bipyridine (57 mg, 0.36 mmol, 2.0 equiv.) were dissolved in DMSO (1.5 mL) and stirred at room temperature for 5 min. To this solution was added dropwise a solution of AgOTf (49 mg, 0.19 mmol, 1.1 equiv.) in DMSO (1.5 mL) and the reaction mixture was heated to 170° C. After 24 h, the reaction mixture was allowed to cool to room temperature and then added to 10 mL of Et$_2$O resulting in the formation of a precipitate. The solids were collected via centrifugation, washed with Et$_2$O (3×5 mL), and then purified via column chromatography (Al$_2$O$_3$, 99:1 CH$_2$Cl$_2$/MeOH, R$_f$=0.4) to afford 130 mg (0.15 mmol, 83% yield) of the desired product as a dark red-purple solid. $^1$H NMR (500 MHz, CDCl$_3$): δ=8.95 (d, J=9.5, 1H), 8.88 (d, J=8.0, 1H), 8.36 (d, J=8.0, 1H), 8.29 (d, J=8.0, 1H), 8.23 (d, J=8.0, 1H), 8.09 (td, J$_1$=8.0, J$_2$=1.3, 1H), 8.03 (td, J$_1$=7.9, J$_2$=1.2, 1H), 7.87 (d, J=8.5, 1H), 7.79 (td, J$_1$=7.9, J$_2$=1.2, 1H), 7.63 (td, J$_1$=6.8, J$_2$=1.0, 1H), 7.54-7.45 (m, 3H), 7.40 (d, J=8.0, 1H), 7.29 (td, J$_1$=7.8, J$_2$=0.7, 1H), 7.16 (td, J$_1$=6.5, J$_2$=1.0, 1H), 7.12 (t, J=7.8, 1H), 7.04 (dd, J$_1$=5.5, J$_2$=0.5, 1H), 7.00 (td, J$_1$=6.6, J$_2$=1.3, 1H), 6.79 (s, 1H), 6.53 (d, J=8.0, 1H), 6.37 (s, 1H), 5.54 (s, 1H), 5.08 (d, J=16.5, 1H), 4.57 (d, J=16.5, 1H), 2.03 (s, 3H), 1.91 (s, 3H). $^{13}$C NMR (125 MHz, CDCl$_3$): δ 197.8, 172.5, 158.9, 158.1, 157.6, 155.6, 154.5, 151.6, 150.8, 148.8, 139.7, 138.7, 138.1, 137.5, 136.9, 136.3, 135.9, 134.9, 134.6, 131.4, 127.7, 126.8, 126.5, 125.7, 125.6, 124.8, 124.1, 123.9, 123.5, 123.4, 123.3, 122.8, 110.4, 108.8, 50.8, 21.3, 21.1. UV-vis (CH$_2$Cl$_2$), λ (ϵ) in nm (M$^{-1}$ cm$^{-1}$): 290 (sh, 1.49×10$^5$), 296 (1.68×10$^5$), 360 (4.92×10$^4$), 460 (sh, 2.43×10$^4$), 496 (2.93×10$^4$). Anal. Calc. for C$_{38}$H$_{31}$F$_3$N$_6$O$_5$S$_1$Ru (4.H$_2$O): C, 53.08; H, 3.87; N, 9.77. Found: C, 53.14; H, 3.99; N, 9.75.

Synthesis of trans(C)—[Ru(1-Me)$_2$(bpy)][OTf]$_2$ (Ru3.2MeOTf)

Complex Ru3 (50 mg, 61 μmol) was dissolved in CH$_2$Cl$_2$ (2 mL) and then cooled to −30° C. After 30 min, 0.20 mL of a 0.77 M solution of MeOTf in CH$_2$Cl$_2$ (0.15 mmol, 2.5 equiv.) was added dropwise and the reaction was allowed to warm to room temperature and stirred for 2 h. The solution was then concentrated to 1 mL and added to 10 mL of hexanes resulting in the formation of a precipitate. The solids were collected via centrifugation, washed with EtOAc (3×5 mL) and Et$_2$O (3×5 mL), and then dried in vacuo to afford 65 mg (57 μmol, 93% yield) of the desired product as a light orange-red solid. $^1$H NMR (500 MHz, acetone-d$_6$): δ=8.58 (d, J=5.5, 2H), 7.88-7.80 (m, 4H), 7.78 (t, J=7.8, 4H), 7.37 (t, J=7.8, 2H), 7.19 (t, J=7.5, 2H), 7.15 (t, J=5.8, 2H), 6.94 (s, 2H), 6.77 (s, 2H), 6.56 (d, J=8.0, 2H), 5.80 (d, J=4.5, 4H), 5.72 (s, 2H), 4.27 (s, 6H), 2.13 (s, 6H), 2.05 (s, 6H, overlaps acetone-d$_5$). UV-vis (CH$_2$Cl$_2$), λ (ϵ) in nm (M$^{-1}$ cm$^{-1}$): 296 (8.59×10$^4$), 329 (5.06×10$^4$), 445 (1.10× 10$^4$). Anal. Calc. for C$_{48}$H$_{45}$F$_6$N$_6$O$_{10.5}$S$_2$Ru (5.0.5H$_2$O): C, 50.00; H, 3.93; N, 7.29. Found: C, 49.91; H, 3.94; N, 7.20.

Synthesis of Ru(1-Me)(bpy)$_2$][OTf]$_2$ (Ru4.MeOTf)

Complex Ru4 (50 mg, 59 μmol) was dissolved in CH$_2$Cl$_2$ (2 mL) and then cooled to −30° C. After 30 min, 0.10 mL of a 0.77 M solution of MeOTf in CH$_2$Cl$_2$ (77 μmol, 1.3 equiv.) was added dropwise and the reaction was allowed to warm to room temperature and stirred for 2 h. The solution was then concentrated to 1 mL and added to 10 mL of hexanes resulting in the formation of a precipitate. The solids were collected via centrifugation, washed with Et$_2$O (3×5 mL), and then dried in vacuo to afford 57 mg (57 μmol, 97% yield) of the desired product as a light orange-red solid. $^1$H NMR (500 MHz, acetone-d$_6$): δ=9.52 (d, J=5.0, 1H), 8.93 (d, J=5.0, 1H), 8.79 (d, J=8.3, 1H), 8.71 (d, J=8.3, 1H), 8.57 (d, J=8.2, 1H), 8.35 (t, J=7.4, 1H), 8.28 (t, J=7.4, 1H), 8.18-8.10 (m, 2H), 7.88 (d, J=8.3, 1H), 7.80-7.75 (m, 2H), 7.74-7.68 (m, 2H), 7.59-7.51 (m, 2H), 7.39 (t, J=7.6, 1H), 7.25-7.17 (m, 2H), 6.87 (s, 1H), 6.68 (s, 1H), 6.59 (d, J=8.3, 1H), 5.85 (d, J=18.3, 1H), 5.69 (s, 1H), 5.44 (d, J=18.4, 1H), 3.81 (s, 3H), 2.07 (s, 3H), 1.86 (s, 3H). UV-vis (CH$_2$Cl$_2$), λ (ε) in nm (M$^{-1}$ cm$^{-1}$): 291 (1.43×10$^5$), 330 (6.28×10$^4$), 429 (2.03×10$^4$), 454 (2.30×10$^4$). Anal. Calc. for C$_{40}$H$_{34}$F$_6$N$_6$O$_8$S$_2$Ru: C, 47.76; H, 3.41; N, 8.35. Found: C, 47.32; H, 3.77; N, 7.96.

Results and Discussion

Each benzimidazolylidene-carboxylate ligand will occupy two coordination sites, thus any Ru-containing starting material must have two (or a multiple of two) vacant coordination sites or easily-displaceable ligands. Furthermore, coordinative saturation at Ru and resistance of the methylated product to substitution reactions can be achieved with an octahedral geometry and chelating ligands, respectively. Based on these considerations, it was sought to incorporate the benzimidazolylidene-carboxylate ligand into Ru complexes bearing one or two bpy ligands (bpy=2,2'-bipyridyl).

Silver-NHC complexes are useful for the synthesis of other transition metal-NHC complexes because they supply an NHC without requiring the synthesis and isolation of the free carbene[14]. Complex 2 is particularly versatile because it can abstract a halide from as well as transfer its NHC to another transition metal center. We have previously reported that the NHC in 2, a carboxylate-functionalized benzimidazolylidene, can function as a bidentate L,X type ligand for Ru [6].

The complex [RuCl$_2$(bpy)(dmso)$_2$] has been used to prepare coordinately-saturated octahedral Ru complexes [8] and, upon reaction with 2 equiv. of 2, afforded the desired Ru—NHC complex trans(C)—[Ru(1)$_2$(bpy)] (2), featuring two carboxylates available for methylation (reaction a, Scheme 4). $^1$H NMR spectroscopic analysis revealed that both NHC ligands in Ru3 were equivalent, presumably due to the C$_2$ axis bisecting N—Ru—N. Additionally, the signal for the N—CH$_2$ protons shifted from the singlet at 5.17 ppm in [Ag(1)] to two doublets at 5.28 and 5.08 ppm in Ru3, indicating the protons had become inequivalent (i.e. two protons were oriented towards the bpy ligand and two away from it). The fact that the N—CH$_2$ protons became diastereotopic was diagnostic for the formation of a C—Ru—O chelate ring, and has previously been observed with Ru1. Remarkably, one of the 3,5-dimethylphenyl aromatic proton signals in Ru3 was observed at 5.04 ppm, significantly upfield of any of the corresponding signals in [Ag(1)] (7.21 and 7.10 ppm).

Scheme 4. Synthesis of Ru3 and Ru4.

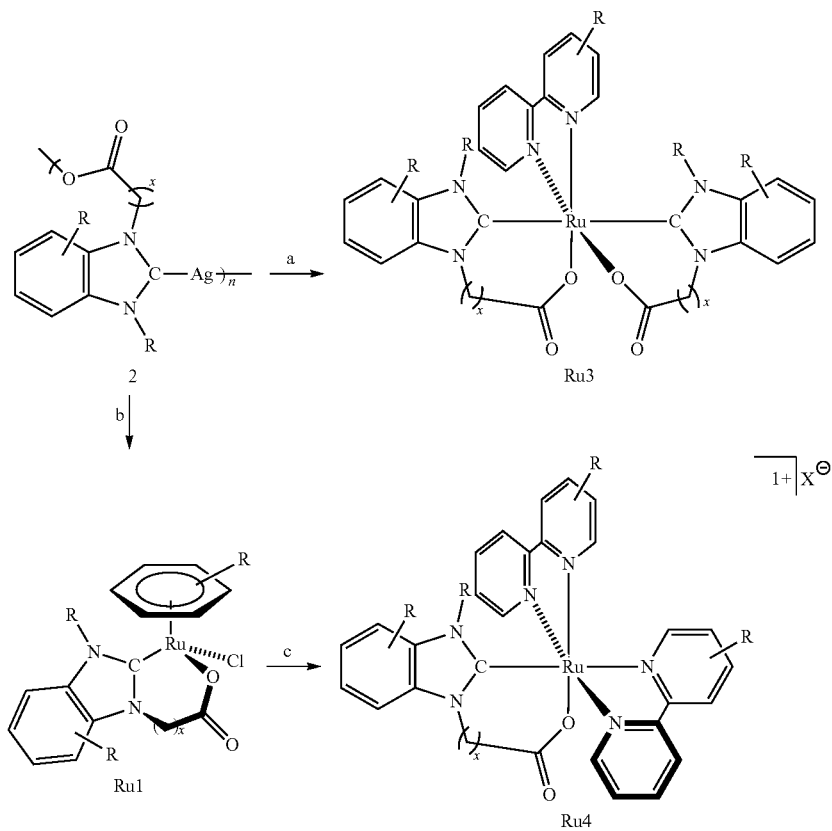

Reagents and conditions: (a) 0.5 equiv. [RuCl$_2$(bpy)(dmso)$_2$], CHCl$_3$, reflux, 24 h 78% yields; (b) 0.5 equiv. [RuCl(η$^6$-cymene)(μ-Cl)], CH$_2$Cl$_2$, RT, 24 h, 97% yield; (c) 2 equiv. 2,2'-bipyridine, 1.05 equiv. AgOTf, DMSO 170° C., 24 h, 83% yield. OTf = O$_3$SCF$_3$, R = 3,5-dimethylphenyl.

Having prepared a complex that could increase in net charge by +2, it was next sought to prepare a complex that could increase in net charge by +1. Because complex Ru3 had the formula [Ru(1)$_2$(bpy)], it was reasoned that a suitable target would have the formula [Ru(1)(bpy)$_2$][A] (A=non-coordinating anion). Initial efforts were directed towards the reaction of 2 with cis-[RuCl$_2$(bpy)$_2$] [15], in conjunction with a variety of halide abstracting reagents, but only complicated mixtures were obtained, containing trace amounts of the desired product along with starting materials, intermediate byproducts, and ligand decomposition products. Given that installing the NHC onto a [Ru(bpy)$_2$] complex was unsuccessful, an alternate route was pursued in which two bpy ligands would be installed onto a pre-formed [Ru(NHC)] complex [16]. Reaction of complex Ru1 with 2 equiv. of bpy in the presence of AgOTf afforded [Ru(1)(bpy)$_2$][OTf] (Ru4) in good yield (reaction c, Scheme 4).

No C$_2$ symmetry was present in complex Ru4 and its $^1$H NMR spectrum revealed all the protons in bpy ligands were inequivalent. Whereas Ru4 had a +1 net charge and Ru3 was overall neutral, the $^1$H NMR spectroscopic data indicated no straightforward trend that the ligands in Ru4 were significantly more electron deficient, and therefore more deshielded, than those in Ru3. Similar to Ru3, the N—CH$_2$ protons in Ru4 were diastereotopic, but the doublets in Ru4 (5.08 and 4.57 ppm) were located upfield of the corresponding signals in Ru3. Conversely, the 3,5-dimethylphenyl aromatic protons in Ru4 (6.79, 6.37 and 5.54 ppm) resonated slightly downfield of those in Ru3 (6.70, 6.17 and 5.44 ppm). Furthermore, the most downfield bpy $^1$H NMR signals occurred at nearly identical chemical shifts (8.95 ppm for Ru4 vs. 8.98 ppm for Ru3). Although no trend was discernible from the individual proton resonances, the aromatic protons in Ru4 were collectively more downfield than those in Ru3. Of the 23 aromatic protons in complex Ru4, 15 were located downfield of the residual CHCl$_3$ peak, compared to only 4 of the 22 aromatic protons in complex Ru3.

Reaction of Ru3 with 2.5 equiv. of MeOTf afforded the dimethylated complex trans(C)—[Ru(1-Me)$_2$(bpy)][OTf]$_2$ (Ru3.2MeOTf) in excellent yield (93%, reaction a, Scheme 5). Similar to complex Ru3, the $^1$H NMR spectrum of Ru3.2MeOTf revealed that the NHC ligands were equivalent. Methylation of the carboxylate moiety of the NHC ligand was inferred from the presence of a peak at 4.27 ppm and relative integration of 6, consistent with the formation of two methyl ester functional groups. In addition, the N—CH$_2$ signal shifted significantly downfield to 5.80 ppm (vs. 5.28 ppm in Ru3) and 10 of the 22 aromatic protons were downfield of 7.26 ppm (vs. 4 protons in Ru3).

Scheme 5: Synthesis of Ru3·2MeOTf and Ru4·MeOTf.

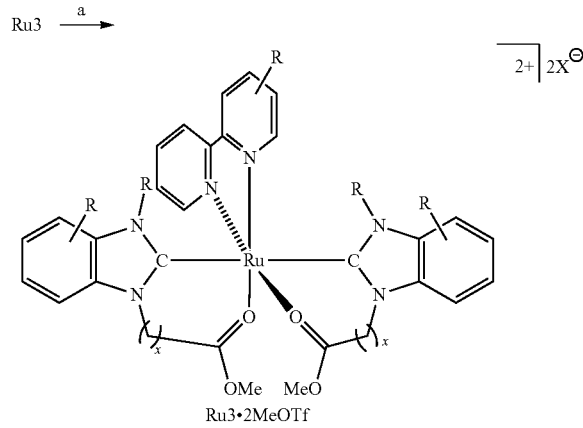

Ru3·2MeOTf

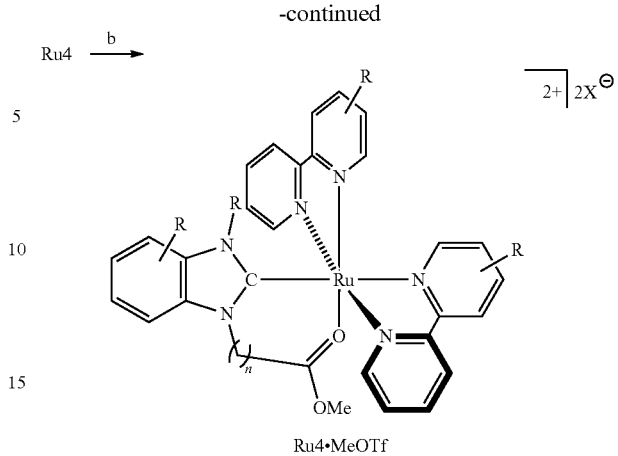

Ru4·MeOTf

Regents and conditions: (a) 2.5 equiv. MeOTf, CH$_2$Cl$_2$, -30° C. → RT, 2 h, 93% yield. (b) 1.3 equiv. MeOTf, CH$_2$Cl$_2$, -30° C. → RT, 2 h, 97% yield. OTF = O$_3$SCF$_3$, R = 3, 5-dimethylphenyl.

Similarly, reaction of complex Ru4 with 1.3 equiv of MeOTf afforded monomethylated complex [Ru(1-Me)(bpy)$_2$][OTf]$_2$ (Ru4.MeOTf) in near-quantitative yield (97%, reaction b, Scheme 5). A new singlet at 3.81 ppm was present in the $^1$H NMR spectrum of Ru4.MeOTf that was attributed to the formation of a methyl ester. Additionally, the doublets for the N—CH$_2$ protons in Ru4.MeOTf (5.85 and 5.44 ppm) were significantly downfield of the corresponding peaks in the $^1$H NMR spectrum of Ru4 (5.08 and 4.57 ppm), consistent with a +1 increase in net charge on the complex rendering the metal (and thus also the ligands attached to it) more electron deficient. In support of this conclusion, the most downfield peak in the $^1$H NMR spectrum of Ru4.MeOTf was at 9.52 ppm, compared to 8.95 ppm for Ru4.

All attempts to isolate the monomethylated analog of Ru3.2MeOTf, comprising one methyl ester and one carboxylate, were unsuccessful. Reaction of Ru3 with 0.1 equiv. of MeOTf at −78° C., quenching via precipitation at this temperature, and immediate $^1$H NMR analysis of the crude precipitate revealed one additional methyl ester peak (4.20 ppm) and four aryl-CH$_3$ (2.18, 2.07, 1.95 and 1.93 ppm) singlets distinct from the resonances arising from Ru3 or Ru3.2MeOTf. Despite the low temperature and low stoichiometry employed in this reaction, complex Ru3.2MeOTf was also observed in this 1H NMR spectrum in a 1:2 ratio with the supposed monomethylated complex. All complexes isolated from the reactions of Ru3 or Ru4 with MeOTf, including analytically-pure samples of Ru3.2MeOTf and Ru4.MeOTf, were unstable in solution (e.g. CDCl$_3$, CD$_2$Cl$_2$, THF-d$_8$, acetone-d$_6$), which precluded more detailed NMR spectroscopic analysis.

Coordination Chemistry

Figure 8:
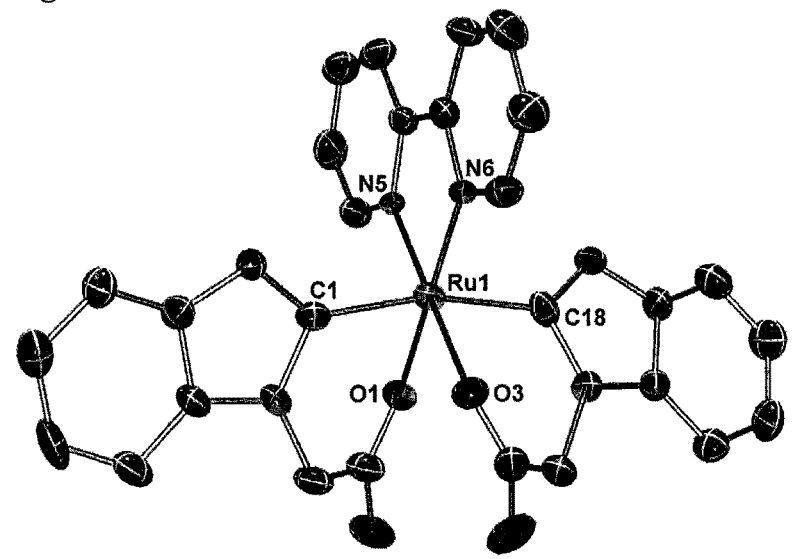
FIG. 8 shows an ORTEP diagram rendered using the POV-Ray engine, shown with 50% probability thermal ellipsoids and selected atom labels for 2. Hydrogen atoms, solvent molecules and N-aryl substituents have been omitted for clarity. Selected distances (Å) and angles (°): Ru1-O1, 2.111(5); R1-O3, 2.113(4); Ru1-N5, 2.008(5); Ru1-N6, 2.021(5); Ru1-C1, 2.057(7); Ru1-C18, 2.062(7); O1-Ru1-O3, 90.48(19); N5-Ru1-N6, 80.3(2); O1-Ru1-C1, 84.6(2); O3-Ru1-C18, 85.8(2); C1-Ru1-C18, 166.1(3).

Single crystals of Ru3 suitable for X-ray diffraction were grown via diffusion of Et$_2$O vapor into a solution of Ru3 in EtOH at room temperature. Crystallographic analysis revealed the two NHC moieties in Ru3 were oriented trans relative to each other (FIG. 8), a configuration that minimized negative steric interactions between the two N-aryl substituents. Overall, the metric parameters determined for Ru3 were consistent with similar complexes that have been previously reported. More specifically, the Ru—C distances (2.057(7) and 2.062(7) Å) and the Ru—O distances (2.111(5) and 2.113(4) Å) in Ru3 fell within the range of values observed for comparable Ru—NHC (2.003-2.089 Å) [12]

and Ru-carboxylate (2.065-2.115 Å) [18] complexes. Interestingly, the average C—O bond distances to the terminal oxygen (1.255(9) Å) and the oxygen coordinated to Ru (1.260(9) Å) were nearly identical in Ru3, suggesting a significant degree of charge delocalization within the carboxylate moieties.

Figure 9:
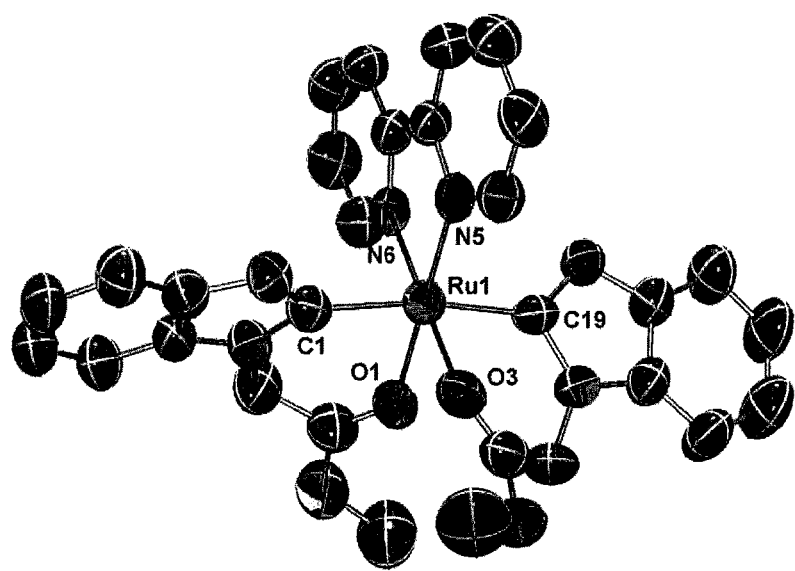
FIG. 9 shows an ORTEP diagram rendered using the POV-Ray engine, shown with 50% probability thermal ellipsoids and selected atom labels for 5. Hydrogen atoms, solvent molecules, counterions and N-aryl substituents have been omitted for clarity. Selected distances (Å) and angles (°): Ru1-O1, 2.139(5); R1-O3, 2.141(4); Ru1-N5, 2.011(5); Ru1-N6, 2.017(5); Ru1-C1, 2.089(6); Ru1-C19, 2.052(6); O1-Ru1-O3, 86.47(18); N5-Ru1-N6, 79.2(2); O1-Ru1-C1, 86.4(2); O3-Ru1-C19, 85.3(2); C1-Ru1-C19, 171.6(2).

Methylation of the terminal carboxylate oxygen atoms upon reaction of Ru3 with MeOTf, inferred by the presence of a methyl ester $OCH_3$ peak in the $^1H$ NMR spectrum of Ru3.2MeOTf, was confirmed by crystallographic analysis (FIG. 9). Although Ru3.2MeOTf had a +2 net charge and Ru3 was overall neutral, the Ru—C distances (2.052(6) and 2.089(6) Å) and the Ru—N distances (2.011(5) and 2.017(5) Å) in Ru3*2MeOTf were not significantly different from those in 2. Methylation of the ligand in Ru3 should convert the charge-delocalized carboxylate moieties to neutral esters that bind Ru via their carbonyl oxygen atoms. The average C—O bond distance to the methylated oxygen (1.317(8) Å) was substantially greater than to the Ru-bound oxygen (1.221(8) Å) in Ru3.2MeOTf, consistent with significant differentiation into single- and double-bond character, respectively. The Ru—O distances (2.139(5) and 2.141(4) Å) in Ru3.2MeOTf were only 2.8 picometers longer than the corresponding distances in Ru3, despite the fact that Ru3.2MeOTf featured a Ru bound to the carbonyl oxygen of a neutral ester ligand, whereas Ru3 featured a Ru bound to the carboxylate oxygen of an anionic carboxylate ligand. Compared to Ru3, the C—Ru—C angle in Ru3.2MeOTf (171.6(2)°) was slightly more obtuse and the O—Ru—O angle (86.47(18)°) was slightly more acute, which could be due to steric repulsion between the two OMe moieties in Ru3.2MeOTf.

Electrochemistry

Figure 10A:
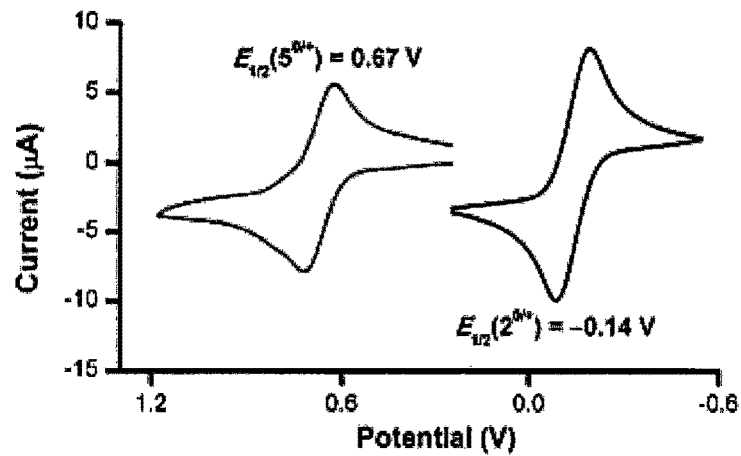
FIG. 10A shows a cyclic voltammogram of 2 (black line) and 5 (grey line) in $CH_2Cl_2$ containing 1.0 mM analyte and 0.10 M [$Bu_4N$][$PF_6$] at 100 mV s$^{-1}$ scan-rate.

Cyclic voltammetry of Ru3 revealed a quasireversible peak at −0.14 V (vs. Fc) that was attributed to the Ru(II)/Ru(III) redox couple (black line, FIG. 10A). Similar analysis of Ru3.2MeOTf indicated that the analogous oxidation process occurred at a potential 0.81 V higher in Ru3.2MeOTf ($E_{1/2}$=0.67 V, grey line, FIG. 10A) than in Ru3, despite the fact that both Ru3 and Ru3.2MeOTf comprised Ru centers in the same oxidation state coordinated to ligand atoms with nearly identical bond distances. Presumably, the +2 net charge in Ru3.2MeOTf that formally resided on Ru significantly lowered the energy of the metal-centered orbitals and, in doing so, raised the energy required to remove electrons from them.

Figure 10B:
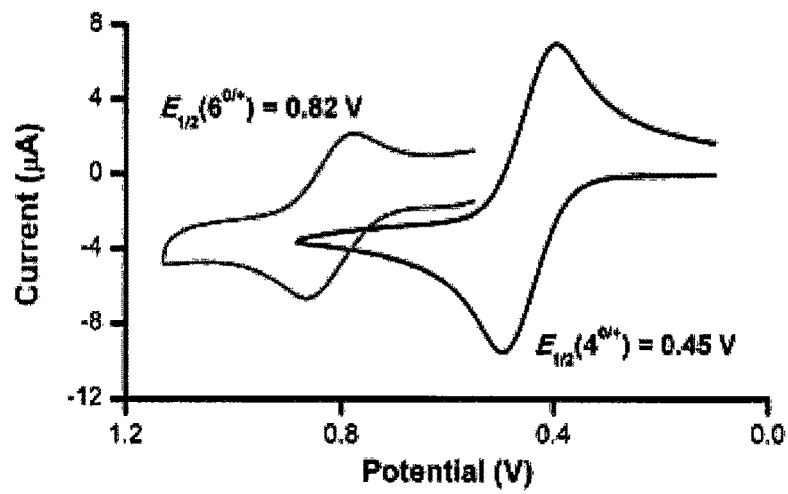
FIG. 10B shows a cyclic voltammogram of 4 (black line) and 6 (grey line) in $CH_2Cl_2$ containing 1.0 mM analyte and 0.10 M [$Bu_4N$][$PF_6$] at 100 mV s$^{-1}$ scan-rate.

Complex 4 exhibited a Ru(II)/Ru(III) redox couple at 0.45 V (black line, FIG. 10B), a potential significantly higher than the corresponding value in Ru3, which could be attributed to Ru4 having a +1 net charge and Ru3 being overall neutral. Unlike Ru3, however, complex Ru4 also exhibited a quasireversible reduction at −1.95 V. The oxidation potential measured for Ru4.MeOTf ($E_{1/2}$=0.82 V, grey line, FIG. 10B) was higher than in Ru4, but the difference between the Ru(II)/Ru(III) oxidation potential in Ru4 and Ru4.MeOTf ($\Delta E_{4 \to 6}$=0.37 V) was substantially lower than between Ru3 and Ru3.2MeOTf ($\Delta E_{2 \to 5}$=0.81 V). Similar to Ru4, complex Ru4.MeOTf displayed reduction peaks, albeit irreversible ones, at −1.02 and −1.81 V. Both Ru3.2MeOTf and Ru4.MeOTf decomposed under all cyclic voltammetry experimental conditions after 2-3 scans, which precluded more detailed analyses.

The increase in Ru(II)/Ru(III) oxidation potential showed a linear correlation with the increase in the net charge on the complex. More specifically, the increase in oxidation potential going from 2 to Ru3.2MeOTf was 2.2 times greater than the increase from Ru4 to Ru4.MeOTf (0.81 V/0.37 V), and the increase in net charge from Ru3 to Ru3.2MeOTf was twice that from Ru4 to Ru4.MeOTf. Examination of the oxidation onset potentials, instead of the half-wave potentials, revealed a closer correlation with net charge. The onset for the Ru(II)/Ru(III) oxidation in Ru3.2MeOTf occurred at a potential 0.77 V higher in energy than in Ru3 (0.58 vs. −0.19 V, respectively), and the corresponding process in Ru4.MeOTf was 0.38 V higher than in Ru4 (0.73 vs. 0.35 V, respectively). Therefore, the increase in oxidation onset potential going from Ru3 to Ru3.2MeOTf was twice the increase from Ru4 to Ru4.MeOTf (0.77 V/0.38 V).

Spectroscopy

Figure 11A:
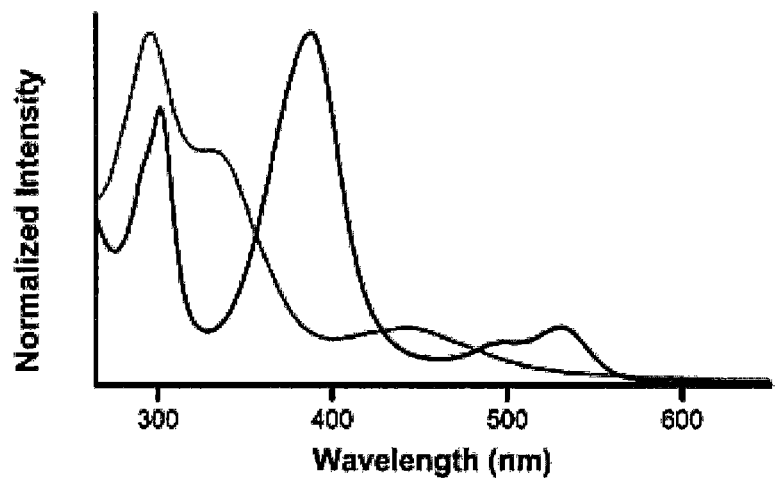
FIG. 11A shows UV-visible spectra of 2 (black line) and 5 (grey line) in $CH_2Cl_2$ containing 1.0 mM analyte and 0.10 M [$Bu_4N$][$PF_6$] at 100 mV s$^{-1}$ scan-rate.
Figure 11B:
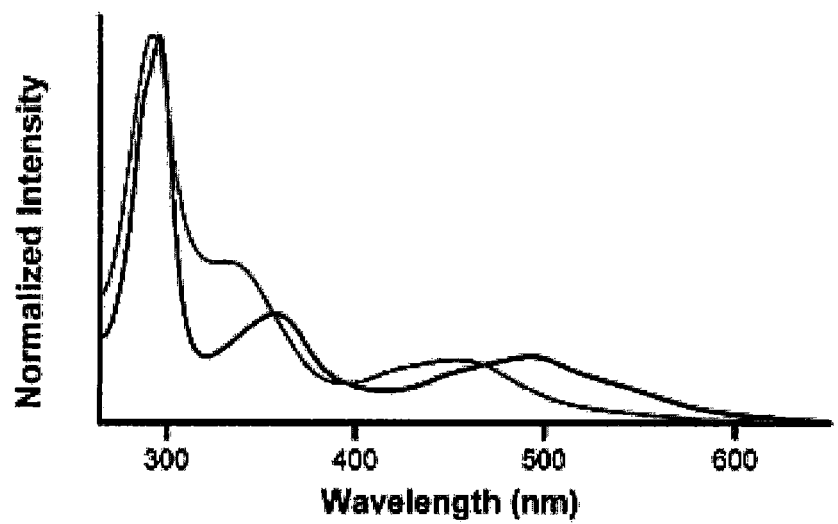
FIG. 11B shows UV-visible spectra of 4 (black line) and 6 (grey line) in $CH_2Cl_2$ containing 1.0 mM analyte and 0.10 M [$Bu_4N$][$PF_6$] at 100 mV s$^{-1}$ scan-rate.

The Ru—NHC complexes were then analyzed by UV-visible spectroscopy to elucidate any correlation between net charge and optical properties. Because the electrochemistry experiments revealed the Ru(II)/Ru(III) oxidation potentials were strongly affected by net charge, the lowest-energy optical transitions were examined, given that they likely involved transitions to or from metal-centered orbitals. The longest-wavelength peaks in Ru3 and Ru3.2MeOTf occurred at 530 nm (2.34 eV) and 445 nm (2.79 eV), respectively (FIG. 11A). Similar analysis of Ru4 and Ru4.MeOTf revealed their longest-wavelength peaks occurred at 496 nm (2.50 eV) and 454 nm (2.73 eV), respectively (FIG. 11B). The difference in longest-wavelength optical transition energy ($\Delta E_{opt}$) between Ru3.2MeOTf and Ru3 was 0.45 eV, whereas $\Delta E_{opt}$ was 0.23 eV between Ru4.MeOTf and Ru4. Considering the ratio of these $\Delta E_{opt}$ values, the increase in energy going from Ru3 to Ru3.2MeOTf was double the increase from Ru4 to Ru4.MeOTf (0.45 eV/0.23 eV).

A similar trend was observed with the second-lowest energy peaks. After the transition at 530 nm, the next longest wavelength peak for Ru3 was located at 386 nm (3.21 eV). Conversion to Ru3.2MeOTf shifted this peak to 329 nm (3.77 eV), a 0.56 eV increase in energy. Analogous peaks in Ru4 and Ru4.MeOTf were observed at 360 nm (3.44 eV) and 330 nm (3.75 eV), respectively, corresponding to an energy difference of 0.31 eV. Based on this second set of peaks, the increase in energy going from Ru3 to Ru3.2MeOTf was 1.8 times the increase from Ru4 to Ru4.MeOTf (0.56 eV/0.31 eV). Although the ratios determined from UV/vis spectroscopy were in good agreement with those obtained via electrochemistry, the possibility that the similarity of these ratio values was coincidental could not be definitively excluded. The UV/vis spectra of Ru3, Ru4, Ru3.2MeOTf and Ru4.MeOTf all displayed multiple transitions, some overlapping, which complicated peak assignments and consequently any interpretation of shifts in energy due to changes in net charge.

A chelating benzimidazolylidene-carboxylate ligand was used to prepare the complexes trans(C)—[Ru(1)$_2$(bpy)] (Ru3) and [Ru(1)(bpy)$_2$][OTf] (Ru4). With two NHC-carboxylate ligands, the net charge on Ru3 was increased by +2 upon methylation to give trans(C)—[Ru(1-Me)$_2$(bpy)][OTf]$_2$ (Ru3.2MeOTf). Similarly, the one NHC-carboxylate ligand in Ru4 reacted with MeOTf to afford [Ru(1-Me)(bpy)$_2$][OTf]$_2$ (Ru4.MeOTf), accompanied by a +1 increase in net charge. Cyclic voltammetry revealed the increase in Ru(II)/Ru(III) oxidation half-wave and onset potentials was 2.2 and 2.0 times greater, respectively, when accompanied by a +2 increase in net charge vs. a +1 increase. UV-visible spectroscopic analysis suggested the first and second longest-wavelength peaks in Ru3 were shifted to higher energy in Ru3.2MeOTf by a factor of 2.0 and 1.8, respectively, greater than the corresponding shift from Ru4 to Ru4.MeOTf. Despite these substantial changes in oxidation potentials and absorption wavelengths, the X-ray crystal structures of Ru3 and Ru4 showed that there were no significant changes in metal-ligand bond distances.

Collectively, these results demonstrate that the Ru centers in Ru3.2MeOTf and Ru4.MeOTf were rendered more electron deficient than those in Ru3 and Ru4, respectively, by amounts linearly proportional to the increase in the net charge of the complexes. Furthermore, the high degree of similarity of the metric parameters in Ru3 and Ru3.2MeOTf suggested that the changes in electron density at the metal centers observed by electrochemistry and UV/vis spectroscopy were not caused by significant changes in coordination chemistry. Because 2 can install the benzimidazolylidene-carboxylate ligand onto a variety of transition metal complexes and methylation of the carboxylate moiety with MeOTf can increase net charge without changing the formal oxidation state or coordination chemistry of the metal center, this represents a general strategy for studying the effects of net charge on the electronic and optical properties of organo-transition metal complexes.

REFERENCES

[1] (a) F. Glorius, Topics Organomet. Chem. 21 (2007) 1; (b) E. Peris, R. H. Crabtree, Coord. Chem. Rev. 248 (2004) 2239; (c) W. A. Herrmann, Angew. Chem. Int. Ed. 41 (2002) 1290.
[2] (a) W. Liu, R. Gust, Chem. Soc. Rev. 42 (2013) 755; (b) M.-L. Teyssot, A.-S. Jarrousse, M. Manin, A. Chevry, S. Roche, F. Norre, C. Beaudoin, L. Morel, D. Boyer, R. Mahiou, A. Gautier, Dalton Trans. (2009) 6894.
[3] (a) H.-J. Park, K. H. Kim, S. Y. Choi, H.-M. Kim, W. I. Lee, Y. K. Kang, Y. K. Chung, Inorg. Chem. 49 (2010) 7340; (b) W.-C. Chang, H.-S. Chen, T.-Y. Li, N.-M. Hsu, Y. S. Tingare, C.-Y. Li, Y.-C. Liu, C. Su, W.-R. Li, Angew. Chem. Int. Ed. 49 (2010) 8161.
[4] (a) O. Songis, C. S. J. Cazin, Synlett 24 (2013) 1844; (b) O. R. Luca, D. L. Huang, M. K. Takase, R. H. Crabtree, New J. Chem. 37 (2013) 3402.
[5] (a) Y. Kayaki, M. Yamamoto, T. Ikariya, Angew. Chem. Int. Ed. 48 (2009) 4194; (b) H. Zhou, W.-Z. Zhang, C.-H. Liu, J.-P. Qu, X.-B. Lu, J. Org. Chem. 73 (2008) 8039; (c) N. P. Mankad, T. G. Gray, D. S. Laitar, J. P. Sadighi, Organometallics 23 (2004) 1191.
[6] A. Mangalum, C. D. McMillen, A. G. Tennyson, Inorg. Chim. Acta 426 (2015) 29.
[7] (a) S. Sinn, B. Schulze, C. Friebe, D. G. Brown, M. Jäger, E. Altuntaş, J. Kübel, O. Guntner, C. P. Berlinguette, B. Dietzek, U.S. Schubert, E. Altuntş, J. Kübel, O. Guntner, C. P. Berlinguette, B. Dietzek, U.S. Schubert, Inorg. Chem. 53 (2014) 2083; (b) C.-S. Lee, R. R. Zhuang, J.-C. Wang, W.-S. Hwang, I. J. B. Lin, Organometallics 31 (2012) 4980; (c) J. A. Cabeza, P. García-Álvarez, E. Pérez-Carreno, V. Pruneda, Chem. Eur. J. 19 (2013) 3426; (d) J. A. Cabeza, I. d. Río, M. C. Goite, E. Pérez-Carreño, V. Pruneda, Chem. Eur. J. 15 (2009) 7339.
[8] T. Suzuki, T. Kuchiyama, S. Kishi, S. Kaizaki, H. D. Takagi, M. Kato, Inorg. Chem. 42 (2003) 785.
[9] G. R. Fulmer, A. J. M. Miller, N. H. Sherden, H. E. Gottlieb, A. Nudelman, B. M. Stoltz, J. E. Bercaw, K. I. Goldberg, Organometallics 29 (2010) 2176.
[10] CrystalClear, in, Rigaku/MSC, The Woodlands, Tex., 2009.
[11] REQAB, in, Rigaku Corporation, Tokyo, Japan, 1998.
[12] (a) G. M. Sheldrick, Acta Cryst. A 64 (2008) 112; (b) G. M. Sheldrick, SHELXTL00: Program for Refinement of Crystal Structures, in: SHELXTL00: Program for Refinement of Crystal Structures, University of Göttingen, Göttingen, Germany, 2000.
[13] (a) A. L. Spek, Acta Cryst. D 65 (2009) 148; (b) A. L. Spek, PLATON, A Multipurpose Crystallographic Tool, in, Utrecht University, Utrecht, The Netherlands, 2000.
[14] I. J. B. Lin, C. S. Vasam, Coord. Chem. Rev. 251 (2007) 642.
[15] M. R. Norris, J. J. Concepcion, C. R. K. Glasson, Z. Fang, A. M. Lapides, D. L. Ashford, J. L. Templeton, T. J. Meyer, Inorg. Chem. 52 (2013) 12492.
[16] W. Ghattas, H. Müller-Bunz, M. Albrecht, Organometallics 29 (2010) 6782.
[17] (a) J. DePasquale, M. Kumar, M. Zeller, E. T. Papish, Organometallics 32 (2013) 966; (b) D. Jantke, M. Cokoja, A. Pöthig, W. A. Herrmann, F. E. Kühn, Organometallics 32 (2013) 741; (c) A. Monney, G. Venkatachalam, M. Albrecht, Dalton Trans. 40 (2011) 2716; (d) S. Horn, C. Gandolfi, M. Albrecht, Eur. J. Inorg. Chem. (2011) 2863; (e) P. Csabai, F. Joó, Organometallics 23 (2004) 5640; (f) F. Simal, D. Jan, L. Delaude, A. Demonceau, M.-R. Spirlet, A. F. Noels, Can. J. Chem. 79 (2001) 529.
[18] (a) G. Türkoglu, S. Tampier, F. Strinitz, F. W. Heinemann, E. Hübner, N. Burzlaff, Organometallics 31 (2012) 2166; (b) J.-H. Oh, T. Nishioka, R. Masui, E. Asato, I. Kinoshita, S. Takara, Polyhedron 29 (2010) 1964; (c) F. Marchetti, C. Pettinari, A. Cerquetella, A. Cingolani, R. Pettinari, M. Monari, R. Wanke, M. L. Kuznetsov, A. J. L. Pombeiro, Inorg. Chem. 48 (2009) 6096; (d) S. Tampier, R. Müller, A. Thorn, E. Hübner, N. Burzlaff, Inorg. Chem. 47 (2008) 9624; (e) P. Štěpnička, New J. Chem. (2002) 567.

Example 3

Transfer hydrogenation catalysis has been used for decades in chemical synthesis to transfer $H_2$ to unsaturated organic substrates, which is analogous to proton-coupled electron transfer. Despite this parallel with biological reductions and these catalysts' widespread use, this report is the first instance of catalytic radical reduction in aqueous solution by a transfer hydrogenation-like process. An organoruthenium complex (Ru1) catalytically reduced 2,2'-azino-bis (3-ethylbenzo-thiazoline-6-sulfonate) radical monoanion (ABTS$^{\cdot-}$) using a non-tertiary alcohol terminal reductant (i.e., $R_1$—CHOH—$R_2$). Both the C—H and O—H groups of the —CHOH— moiety were necessary to function as a terminal reductant. Comparison of ethanol and isopropanol reaction rates to ethanol-$d_6$ and isopropanol-dg yielded primary kinetic isotope effect values indicating H2 transfer from the CH—OH moiety in the rate-determining step. Furthermore, Ru1 slowed oxidative formation of ABTS$^{\cdot-}$ by HO$^{\cdot}$, then reduced all ABTS$^{\cdot-}$ formed, and remained catalytically active over multiple cycles. Collectively, these results demonstrate that Ru1 inhibits the oxidative formation of and catalyzes the reduction of radicals in aqueous solution by a transfer hydrogenation-like process.

Results and Discussion

It was sought to determine if Ru1 could catalyze the reduction of radicals in aqueous solution via a transfer hydrogenation-like process. Alkylation of N-(p-tolyl)-benzimidazole[19] with bromoacetic acid[20] afforded the NHC ligand precursor [1H$_2$][Br] (Scheme 6). The desired Ag—NHC complex [Ag(1)]n (2) was obtained upon treatment of [1H2][Br] with Ag$_2$O. Transfer of the NHC ligand from 2 to Ru was achieved upon reaction with [{RuCl($\eta^6$-cymene)}2 ($\mu$-Cl)2] to afford the Ru—NHC complex [RuCl(1)($\eta^6$-cymene)](Ru1).

Scheme 6; Synthesis of [1H₂][Br], 2 and Ru1.

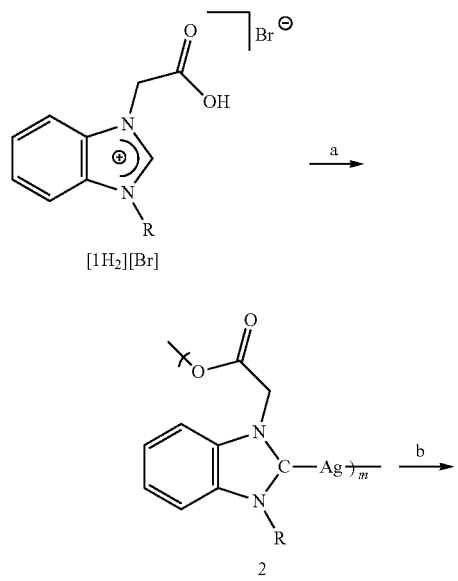

Reagents and conditions: (a) Ag₂O (1.5 equiv.) or (b) [{RuCl(η⁶-cymene)}₂(μ-Cl)₂] (1:1 Ag/Ru), CH₂Cl₂, RT, 24 h. R = p-tolyl.

Consistent with the loss of positive charge in the benzimidazole ring following deprotonation, the $^1$H NMR signal for the N—CH$_2$—CO$_2$ protons in 2 was upfield of the signal in [1H$_2$][Br]. Whereas the N—CH$_2$—CO$_2$ protons in 2 displayed a singlet in the $^1$H NMR spectrum, the corresponding signal in Ru1 was an AB doublet, indicating that the two protons of the N—CH$_2$—CO$_2$ group were oriented in non-exchanging inequivalent magnetic environments due to the ligand chelate ring. Cyclic voltammetry of 1.0 mM Ru1 in CH$_2$Cl$_2$ containing 0.10 M [Bu$_4$N][PF$_6$] revealed no oxidation or reduction processes within the solvent window.

To probe the potential antioxidant activity of Ru1, 2,2'-azino-bis(3-ethylbenzothiazoline-6-sulfonate) radical monoanion (ABTS$^{•-}$), which is stable in aerobic, protic media and undergoes reversible one-electron reduction to ABTS$^{2-}$, was selected as the substrate for studies of catalytic radical reduction (Scheme 7). Investigations of potential radical degrading ability in biological environments often employ ABTS$^{•-}$ as the initial model substrate because its concentration can be readily measured by UV/visible spectroscopy at long wavelengths ($\lambda_{max}$=750 nm in ethanol or 734 nm in phosphate buffered saline),[23] but the non-radical dianion ABTS$^{2-}$, formed upon one-electron reduction of ABTS$^{•-}$, does not absorb above 400 nm. In addition, the large extinction coefficient for ABTS$^{•-}$ ($\epsilon_{750}$=1.6×10$^4$ M$^{-1}$ cm$^{-1}$ in EtOH and $\epsilon_{734}$=1.5×10$^4$ M$^{-1}$ cm$^{-1}$ in PBS) enables kinetic studies of radical-degrading and radical-forming reactions at concentrations more relevant to those encountered during oxidative stress. Furthermore, the oxidation of ABTS$^{2-}$ to ABTS$^{•-}$ occurs at a similar potential (0.67 V vs. Fc$^{0/+}$) to the oxidation of H$_2$O$_2$ to O$_2$ ($E_0'$=0.70 V), thus, from a thermodynamic standpoint, ABTS$^{•-}$ will exhibit similar oxidizing radical reactivity to ROS encountered in biological systems.

Scheme 7: One-electron redox interconversion between ABTS$^{•-}$ and ABTS$^{2-}$ (NH$_4^+$ counterions omitted for clarity).

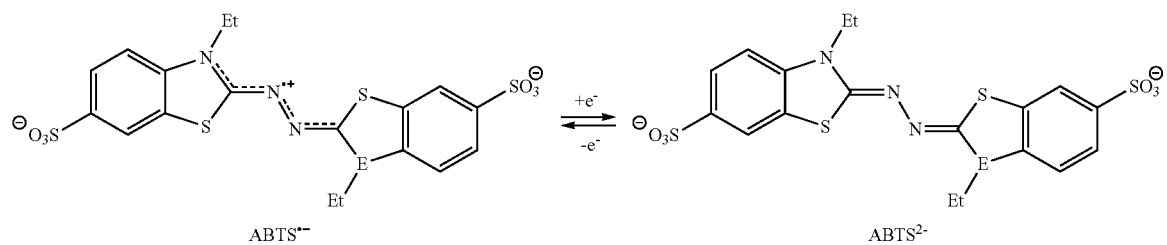

-continued

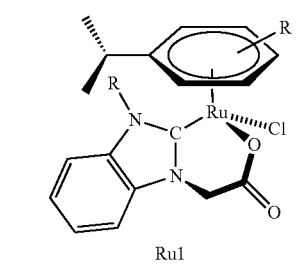

Ru1

As a non-catalytic control, Trolox (Scheme 8) was employed given its use as a benchmark in a variety of radical degradation and antioxidant studies.[24] Trolox can serve as a 1e$^-$ or 2e$^-$ reductant, whereby the first 1e$^-$ oxidation is accompanied by rapid H$^+$ loss to form a phenoxyl radical (TrO$^•$), which can then undergo a second 1e$^-$ oxidation to form a phenoxonium cation (TrO$^+$). In methanol (MeOH) or ethanol (EtOH) solutions, however, these processes converge into a single 2e$^-$ oxidation.[25] Subsequent hydrolysis of TrO$^+$ can then cleave the tertiary carbon-oxonium bond and thus render the 2e$^-$ oxidation of Trolox irreversible.

Scheme 8: First and second one-electron oxidations of Trolox.

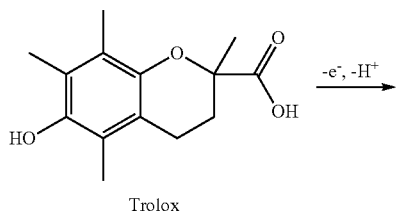

Trolox

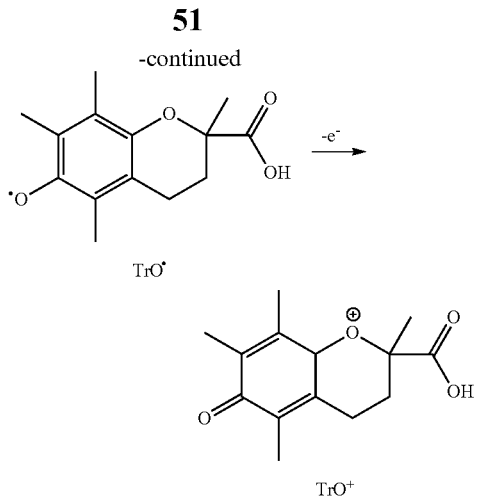

Because its electrochemistry and chemical reactivity have been thoroughly investigated, Trolox is routinely used as the baseline for the evaluation of other antioxidants. One comparison is the Trolox equivalent antioxidant capacity (TEAC) assay, in which the percent of ABTS$^{\cdot-}$ degradation is plotted vs. antioxidant concentration and the slope of the linear fit for the antioxidant is divided by the slope similarly obtained for Trolox. However, the TEAC assay presupposes the antioxidant being studied degrades ABTS$^{\cdot-}$ (i) in a dose-dependent or stoichiometric manner, (ii) by serving as the ultimate source of reducing equivalents, and (iii) reacting on a timescale similar to Trolox, presuppositions that would not be satisfied by some catalytic systems. For example, a compound that degrades ABTS$^{\cdot-}$ catalytically could degrade 100% of the ABTS$^{\cdot-}$ at all concentrations (i.e., is dose-independent). A linear fit of this data would have zero slope and thus afford a TEAC value of zero, leading to the contradictory determination that this catalyst had zero antioxidant capacity relative to Trolox despite the fact that it degraded 100% of the ABTS$^{\cdot-}$ at all concentrations and Trolox did not. Because the TEAC assay may be unable to quantify the antioxidant capacity of some catalytic systems, traditional catalyst kinetic analyses are thus required.

Catalytic Reduction of ABTS$^{\cdot-}$ to ABTS$^{2-}$ in EtOH

Figure 12A:
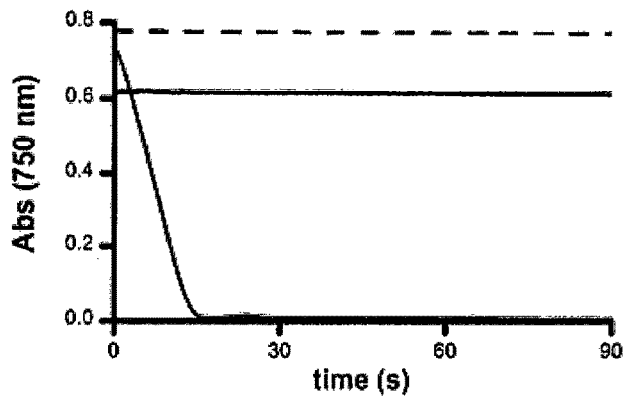
FIG. 12A shows a graph of ABTS$^{•-}$ reduction after adding 5 µM Ru1 (black line) or 5 µM Trolox (straight black line), vs. initial ABTS$^{•-}$ absorbance (dashed grey line).

Addition of 5 μM Ru1 (DMSO stock) to 50 μM ABTS$^{\cdot-}$ in EtOH caused a 100% decay in radical absorbance at 750 nm within 30 s (FIG. 12A, black line). Accompanying this degradation of 50 μM ABTS$^{\cdot-}$ was an increase in absorbance at 340 nm corresponding to the formation of 50 μM ABTS$^{2-}$, indicating 1:1 conversion of ABTS$^{\cdot-}$ to ABTS$^{2-}$ by Ru1. Collectively, these results demonstrated that 5 μM Ru1 could achieve complete reduction of 50 μM ABTS$^{\cdot-}$ (i.e., 10 turnovers). In the absence of Ru1, no ABTS$^{\cdot-}$ degradation was observed in EtOH alone (FIG. 12A, dashed grey line), indicating that Ru1 catalyzed the reduction of ABTS$^{\cdot-}$ to ABTS$^{2-}$ and was essential for reactivity. No ABTS$^{\cdot-}$ formation was observed in an EtOH solution containing 5 μM Ru1 (DMSO stock) and 50 μM ABTS$^{2-}$, even after extended periods of time, indicating that Ru1 does not oxidize ABTS$^{2-}$ to ABTS$^{\cdot-}$ under these conditions and thus is unlikely to exert any pro-oxidant effects. The radical reducing activity of Ru1 was not limited to ABTS$^{\cdot-}$, and catalytic reduction of 2,2-diphenyl-1-picrylhydrazyl radical (DPPH$^{\cdot}$) to 1,1-diphenyl-2-picrylhydrazine (DPPH-H) in EtOH was also observed. In contrast to Ru1, the addition of 5 μM Trolox caused a rapid (within mixing time) decrease in the absorbance at 750 nm, but only by 20% (FIG. 12A, straight black line), corresponding to the reduction of 10 μM ABTS$^{\cdot-}$ (2 equiv. vs Trolox) and consistent with the ability of Trolox to serve as a non-catalytic 2e$^-$ reductant in EtOH solution.[25]

Figure 12B:
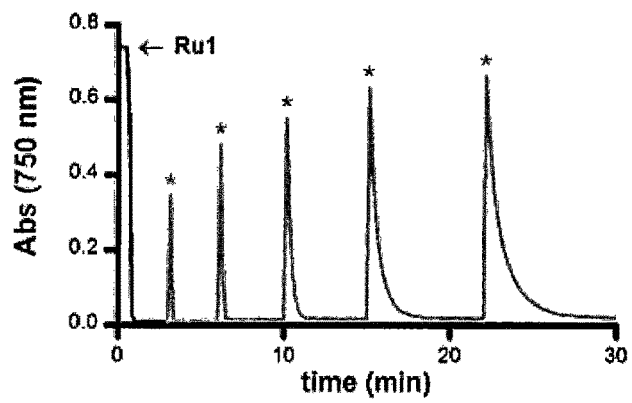
FIG. 12B shows a graph of ABTS$^{•-}$ reduction after adding 5 µM Ru1 (black line) then 5 additional 50 µM ABTS$^{•-}$ aliquots (*, grey line). Conditions: [ABTS$^{•-}$]$_0$=50 µM in EtOH at 25° C.; absorbance measured at 750 nm.
Figure 12C:
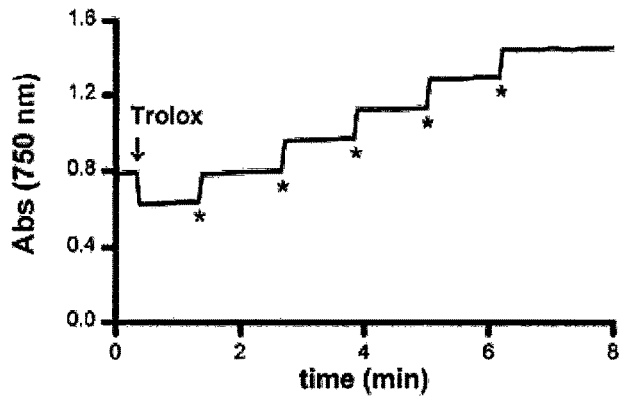
FIG. 12C shows a graph of ABTS$^{•-}$ reduction after adding 5 µM Trolox (black line) then 5 additional 10 µM ABTS$^{•-}$ aliquots (*, grey line). Conditions: [ABTS$^{•-}$]$_0$=50 µM in EtOH at 25° C.; absorbance measured at 750 nm.

To assess its catalytic potential and corresponding regeneration, the reactivity of Ru1 with multiple sequential aliquots of excess ABTS$^{\cdot-}$ was examined. After the reduction of 50 μM ABTS$^{\cdot-}$ by 5 μM Ru1 (DMSO stock) was complete (FIG. 12B, black line), 5 additional 50 μM aliquots of ABTS$^{\cdot-}$ were introduced, whereupon complete ABTS$^{\cdot-}$ reduction occurred each time (FIG. 12B, grey line, 60 turnovers). Although the time required for complete degradation increased with each successive ABTS$^{\cdot-}$ aliquot, 5 μM Ru1 nonetheless remained catalytically competent for the complete reduction of 500 μM ABTS$^{\cdot-}$. Rate law studies demonstrated that ABTS$^{2-}$ is an inhibitor for the Ru1-catalyzed reduction of ABTS$^{\cdot-}$ (vide infra), thus the increase in time needed for complete degradation is caused by the fact that each successive ABTS$^{\cdot-}$ aliquot is in the presence of a higher concentration of ABTS$^{2-}$ than the previous ABTS$^{\cdot-}$ aliquot. Unlike Ru1, adding successive 10 μM aliquotst of ABTS$^{\cdot-}$ after the initial reaction with 5 μM Trolox (FIG. 12C, black line) caused the absorbance at 750 nm to in increase (FIG. 12C, grey line) by amounts proportional to the concentration of ABTS$^{\cdot-}$ added (i.e., 10 μM×1.6×10$^4$ M$^{-1}$ cm$^{-1}$), indicating that the antioxidant capacity of Trolox was exhausted upon reduction of 2 equiv. of ABTS$^{\cdot-}$. Together, these data demonstrate that Ru1 catalytically reduces radicals and, because it is regenerated after each reaction cycle, can degrade significantly more radicals than a non-catalytic antioxidant.

Although ABTS$^{\cdot-}$ degradation has been previously observed with other ruthenium complexes,[26-28] Ru1 is, to the best of our knowledge, the first with demonstrated catalytic activity. It is important to note that these previous studies measured the percentage of ABTS$^{\cdot-}$ degradation as a function of Ru complex concentration (i.e., the TEAC assay approach). Interestingly, some reported absorbance vs. time plots displayed significantly slower ABTS$^{\cdot-}$ degradation compared to Trolox and, notably, 100% ABTS$^{\cdot-}$ degradation at multiple different Ru concentrations. Thus, it is entirely possible that one or more of the previously reported Ru complexes may have, in fact, degraded ABTS$^{\cdot-}$ catalytically. Significantly slower reactivity compared to Trolox may have created the appearance that the total percentage of ABTS$^{\cdot-}$ degraded by a Ru complex was dependent on the initial concentration of that complex and therefore led to the conclusion that radical degradation was non-catalytic.

As a catalyst for the 1e$^-$ reduction of ABTS$^{\cdot-}$ to ABTS$^{2-}$, Ru1 itself cannot serve as the terminal reductant for this reaction. Because the H$_2$ for the transfer hydrogenation of C=O, C=N, and C=C bonds catalyzed by an organoruthenium complex is ultimately supplied by the non-tertiary alcohol solvent (e.g., Ru1 and i-PrOH),[18] the electrons for the ABTS$^{\cdot-}$ reduction experiments displayed in FIG. 12 most likely came from the EtOH solvent. To test this hypothesis and identify the chemical features required for terminal reductant function, it was first necessary to determine experimental conditions under which no ABTS$^{\cdot-}$ degradation occurred in the presence of Ru1 alone.

Phosphate-buffered saline (PBS, pH 7.4) was selected as a suitable reaction medium because neither the solvent (H$_2$O) nor the buffer components (Na$_2$HPO$_4$, KH$_2$PO$_4$, NaCl, KCl) were likely to undergo oxidation to supply the electrons necessary for the reduction of ABTS$^{\cdot-}$ to ABTS$^{2-}$. However, addition of 5 μM Ru1 (DMSO stock) to ABTS$^{\cdot-}$ in PBS caused a gradual decay in radical absorbance at 734 nm, which indicated a suitable terminal reductant was present. Given that other radical scavenging assays have demonstrated that DMSO can function as a reductant,[29] we concluded that the DMSO from the Ru1 stock solution was the most likely source of the reducing equivalents necessary for the reactivity. Addition of DMSO alone to ABTS$^{•-}$ in PBS produced no change in absorbance at 734 nm, again demonstrating that the reduction of ABTS$^{•-}$ to ABTS$^{2-}$ cannot occur without the catalyst Ru1.

To avoid the complications associated with redox active solvents, Ru1 stock solutions were thus prepared in CH$_3$CN. No degradation of ABTS$^{•-}$ in PBS was observed after treatment with 5 μM Ru1 from a CH$_3$CN stock (FIG. 13), indicating this solution lacked a suitable terminal reductant and confirming the prior determination that DMSO could provide reducing equivalents. Addition of 50 mM EtOH to 5 μM Ru1 (CH$_3$CN stock), 50 μM ABTS$^{•-}$ and 100 μM ABTS$^{2-}$ in PBS caused the absorbance at 734 nm to decrease (FIG. 13), thus confirming the hypothesis that the electrons necessary for the ABTS$^{•-}$ reduction observed in FIG. 12 were ultimately supplied by the EtOH solvent. Establishing experimental conditions under which no reaction occurred between the catalyst (Ru1) and substrate (ABTS$^{•-}$) alone but did occur after the addition of EtOH provided the baseline necessary to study the catalyst kinetics and to gain insight into the mechanism for the reduction of ABTS$^{•-}$ to ABTS$^{2-}$.

The synthesis of ABTS$^{•-}$ from ABTS$^{2-}$ does not proceed to 100% completion, thus any ABTS$^{•-}$ solution prepared will also inevitably contain a smaller amount of ABTS$^{2-}$, the latter of which inhibits the Ru1-catalyzed reduction of ABTS$^{•-}$ to ABTS$^{2-}$ (vide infra). Furthermore, because the ratio of ABTS$^{•-}$ to ABTS$^{2-}$ is not constant from one synthetic batch to the next, the amount of inhibitor relative to catalyst will vary among the different experiments and thus cause significant variations in observed rates. Consequently, the standard protocol for the rate law studies entailed the addition of 100 μM ABTS$^{2-}$ (i.e., 20 equiv. relative to the typical 5 μM Ru1 concentration) to each experiment (with the exception of FIG. 4B) to minimize variations caused by inconstant ABTS$^{2-}$ to Ru1 ratios.

Figure 14A:
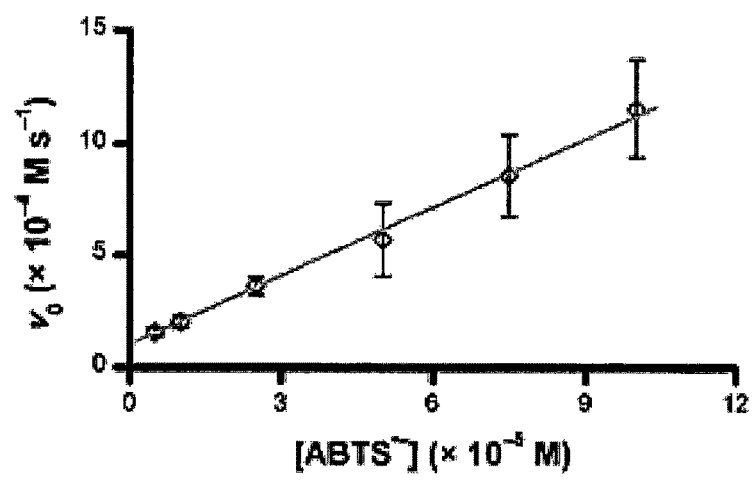
FIG. 14A shows a graph illustrating the dependence of initial rate (v$_0$) of reduction of ABTS$^{•-}$ catalyzed by Ru1 on [ABTS$^{•-}$]$_0$=5, 10, 25, 50 or 75 µM. Each data point (◇) is the average of 4 experiments performed on 4 different days and the error bars represent the standard deviation. Conditions: [Ru1]$_0$=5 µM, [ABTS$^{•-}$]0=50 µM, [ABTS$^{2-}$]$_0$=100 µM, [EtOH]$_0$=50 mM, PBS (pH 7.4), 25° C.; absorbance measured at 734 nm (unless specified otherwise).

To PBS solutions containing 5 μM Ru1 (CH$_3$CN stock), 100 μM ABTS$^{2-}$ and various initial concentrations of ABTS$^{•-}$ (5, 10, 25, 50 or 75 μM) was added 50 mM EtOH and the initial rates of ABTS$^{•-}$ degradation (v$_0$) were measured for each experiment. The plot of v$_0$ vs. [ABTS$^{•-}$]$_0$ revealed a linear correlation (FIG. 14A), which indicated that the Ru1-catalyzed reduction of ABTS$^{•-}$ was first-order in [ABTS$^{•-}$] and that observed rate constants (k$_{obs}$) could be obtained by plotting ln(A/A$_0$) vs. t and performing linear regression.

Previous studies by others have shown that when a L$_n$Ru—Cl complex is added to H$_2$O, the Cl$^-$ ligand is rapidly displaced to form the cationic aquo complex [L$_n$Ru(OH$_2$)]$^{1+}$. However, in a PBS solution containing ABTS$^{•-}$ and ABTS$^{2-}$, there are multiple anionic species present that could conceivably have a higher affinity for [L$_n$Ru]$^{1+}$ than H$_2$O. During the initial studies of the Ru-catalyzed reduction of ABTS$^{•-}$ in PBS solutions (which did not contain the additional 100 μM ABTS$^{2-}$), experiments performed under identical conditions yielded significantly different v$_0$ values that could not be attributed to any known variable or impurity. Eventually, we hypothesized that, because each stock solution of ABTS$^{•-}$ unavoidably contained slightly different amounts of unoxidized ABTS$^{2-}$, it was the attendant variation in the ABTS$^{2-}$:Ru1 ratios among the different experiments that caused the variation in v$_0$ values.

Figure 14B:
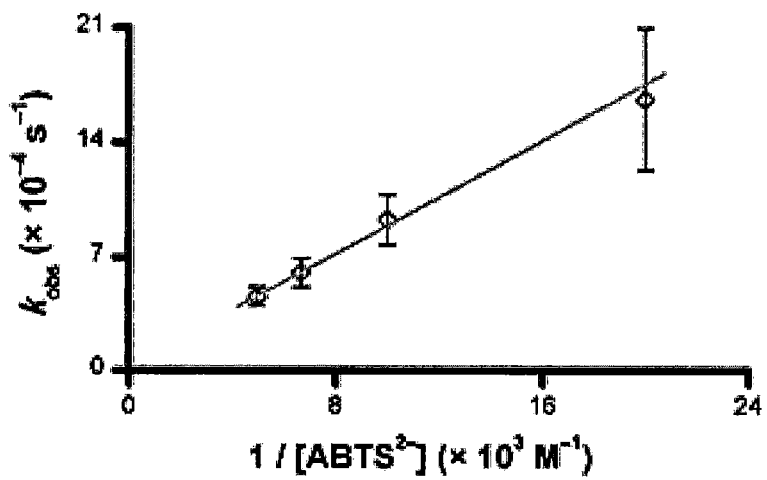
FIG. 14B shows a graph illustrating the dependence of observed rate constant ($k_{obs}$) for Ru1-catalyzed ABTS$^{•-}$ reduction on [ABTS$^{2-}$]$_0$=50, 100, 150 or 200 µM. Each data point (◇) is the average of 4 experiments performed on 4 different days and the error bars represent the standard deviation. Conditions: [Ru1]$_0$=5 µM, [ABTS$^{•-}$]0=50 µM, [ABTS$^{2-}$]$_0$=100 µM, [EtOH]$_0$=50 mM, PBS (pH 7.4), 25° C.; absorbance measured at 734 nm (unless specified otherwise).

To test this hypothesis, 50 mM EtOH was added to solutions of 5 μM Ru1 (CH$_3$CN stock), 50 μM ABTS$^{•-}$ and various initial concentrations of extra ABTS$^{2-}$ (50, 100, 150 or 200 μM) in PBS and k$_{obs}$ values were measured for each experiment. Notably, k$_{obs}$ decreased as [ABTS$^{2-}$]$_0$ increased, which indicated that ABTS$^{2-}$ functioned as an inhibitor for the reaction. A linear correlation was observed in the plot of k$_{obs}$ vs. 1/[ABTS$^{2-}$]$_0$ (FIG. 14B), which suggested that ABTS$^{2-}$ dissociation from the Ru center was necessary for the catalytic reaction to proceed and confirmed our hypothesis that the minor differences in ABTS$^{2-}$ concentrations in the ABTS$^{•-}$ stock solutions caused significant variation in v$_0$ values. Therefore, an extra 100 μM ABTS$^{2-}$ was added to each experiment performed in PBS, to ensure that the ABTS$^{2-}$:Ru1 ratios were always ≥20 and relatively constant.

Figure 14C:
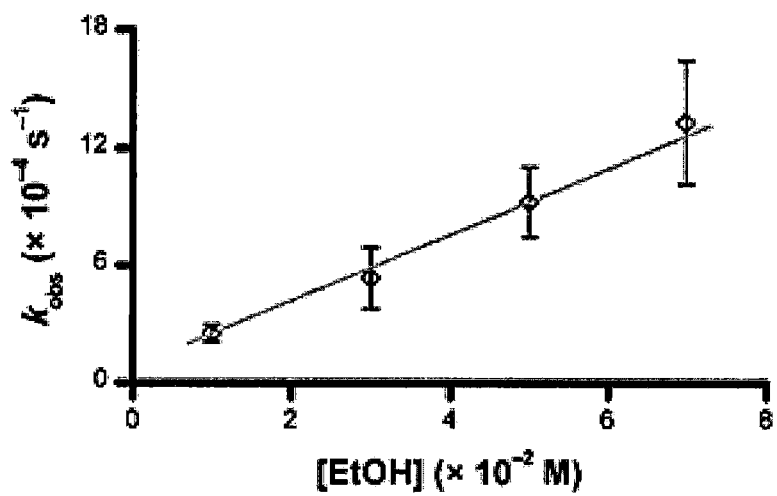
FIG. 14C shows a graph illustrating the dependence of observed rate constant ($k_{obs}$) for Ru1-catalyzed ABTS$^{•-}$ reduction on [EtOH]$_0$=10, 30, 50 or 70 mM. Each data point (◇) is the average of 4 experiments performed on 4 different days and the error bars represent the standard deviation. Conditions: [Ru1]$_0$=5 µM, [ABTS$^{•-}$]0=50 µM, [ABTS$^{2-}$]$_0$=100 µM, [EtOH]$_0$=50 mM, PBS (pH 7.4), 25° C.; absorbance measured at 734 nm (unless specified otherwise).

Because EtOH was essential for the Ru1-catalyzed reduction of ABTS$^{•-}$ to ABTS$^{2-}$, it was next sought to determine the dependence of the reaction on EtOH concentration. To solutions of 5 μM Ru1 (CH$_3$CN stock), 50 μM ABTS$^{•-}$ and 100 μM ABTS$^{2-}$ in PBS were added various initial concentrations of EtOH (10, 30, 50 or 70 mM), and the plot of k$_{obs}$ vs. [EtOH]$_0$ revealed that the rate constant increased linearly with initial EtOH concentration (FIG. 14C). Because the addition of EtOH does not cause ABTS$^{•-}$ degradation in the absence of Ru1, the linear dependence of k$_{obs}$ on [EtOH]$_0$ suggested that the coordination of EtOH to Ru was a necessary step to generating the catalytic intermediate that was competent for ABTS$^{•-}$ reduction.

Figure 14D:
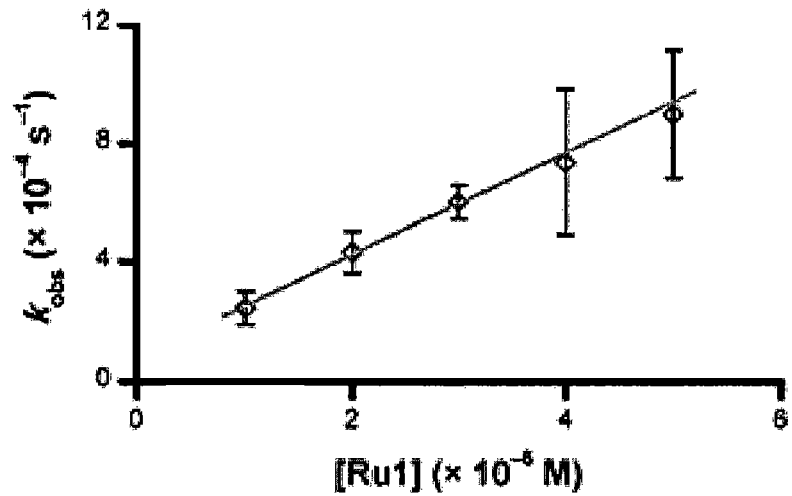
FIG. 14D shows a graph illustrating the dependence of observed rate constant ($k_{obs}$) for Ru1-catalyzed ABTS$^{•-}$ reduction on [Ru1]$_0$=1, 2, 3, 4 or 5 µM. Each data point (◇) is the average of 4 experiments performed on 4 different days and the error bars represent the standard deviation. Conditions: [Ru1]$_0$=5 µM, [ABTS$^{•-}$]0=50 µM, [ABTS$^{2-}$]$_0$=100 µM, [EtOH]$_0$=50 mM, PBS (pH 7.4), 25° C.; absorbance measured at 734 nm (unless specified otherwise).

Some [L$_n$Ru(OH$_2$)]$^{n+}$ complexes have been reported to undergo loss of H$^+$ and conversion to hydroxo-bridged dimers of the form [(L$_n$Ru)$_2$(μ-OH)]$^{(n-1)+}$, therefore it is conceivable that a similar transformation occurs upon addition of Ru1 to aqueous buffer. To elucidate the nuclearity of the catalytically-active species derived from Ru1, it was then analyzed the relationship between Ru1 concentration and ABTS$^{•-}$ reduction. To PBS solutions containing 50 μM ABTS$^{•-}$, 100 μM ABTS$^2$, and various initial concentrations of Ru1 (1, 2, 3, 4 or 5 μM; CH$_3$CN stocks) was added 50 mM EtOH, and the k$_{obs}$ values measured increased linearly with increasing [Ru1]$_0$ (FIG. 14D). If the predominant Ru-containing species in solution were multinuclear, such as [(L$_n$Ru)$_2$(μ-OH)]$^{1+}$ or [(L$_n$Ru)$_2$(μ-O)], this species would need to dissociate an [L$_n$Ru]$^{n+}$ subunit to generate a free coordination site to allow EtOH to bind, and k$_{obs}$ would thus depend on [Ru1]$_0^{1/2}$ (if dimeric) or [Ru1]$_0^{1/m}$ (if a multinuclear species derived from m Ru1 subunits). However, because the observed rate constant depended linearly on [Ru1], the predominant Ru-containing species in solution leading up to the rate-determining step was most likely mononuclear. Furthermore, given that each experiment contained ≥20 equiv. ABTS$^{2-}$ for each molecule of Ru1 added and that ABTS$^{2-}$ dissociation was necessary for ABTS$^{•-}$ reduction to occur, it was concluded that the predominant Ru-containing species was a Ru-ABTS$^{2-}$ complex.

Figure 14E:
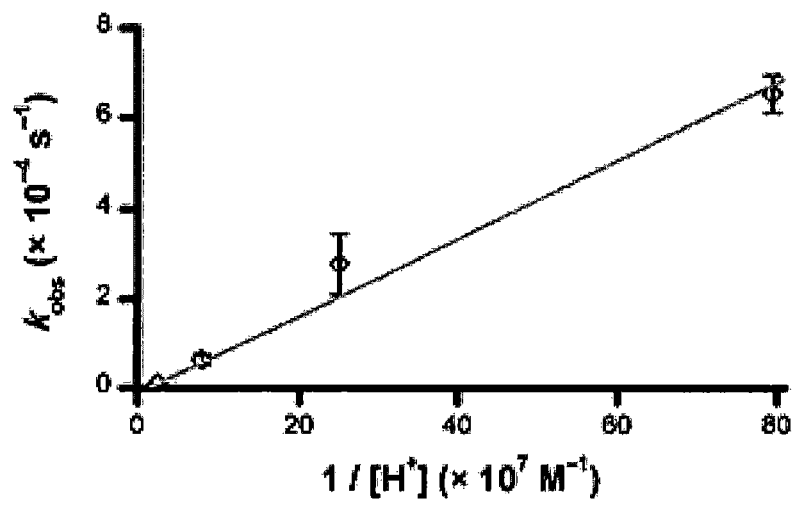
FIG. 14E shows a graph illustrating the dependence of observed rate constant ($k_{obs}$) for Ru1-catalyzed ABTS$^{•-}$ reduction on pH=7.4, 7.9, 8.4 or 8.9. Each data point (◇) is the average of 4 experiments performed on 4 different days and the error bars represent the standard deviation. Conditions: [Ru1]$_0$=5 µM, [ABTS$^{•-}$]0=50 µM, [ABTS$^{2-}$]$_0$=100 µM, [EtOH]$_0$=50 mM, PBS (pH 7.4), 25° C.; absorbance measured at 734 nm (unless specified otherwise).

In a transfer hydrogenation catalytic cycle, the intermediate complex responsible for adding H$_2$ to the unsaturated substrate (e.g., H$_2$Ru$_{cat}$) is formed via removal of H$^+$ and H$^-$ from the OH and CH groups, respectively, in the CH—OH moiety of a non-tertiary alcohol. Unlike transfer hydrogenation, however, the reduction of ABTS$^{•-}$ to ABTS$^{2-}$ will not be accompanied by H$^+$ transfer to ABTS$^{2-}$, therefore the buffer must absorb the 2 equiv. of H$^+$ generated during each turnover. Therefore, the reaction rate for the Ru1-catalyzed reduction of ABTS$^{•-}$ to ABTS$^{2-}$ was expected to depend on the concentration of H$^+$ in solution. To elucidate the relationship between [H$^+$] and reaction rate, 50 mM EtOH was added to 5 μM Ru1 (CH$_3$CN stock), 50 μM ABTS$^{•-}$ and 100 μM ABTS$^{2-}$ in PBS solutions at various pH values (7.4, 7.9, 8.4 or 8.9), and ABTS$^{\cdot-}$ reduction was faster at higher pH values. Notably, the linear correlation observed in the plot of $k_{obs}$ vs. 1/[H$^+$] (FIG. 14E) indicated that a deprotonation reaction, in which H$^+$ was transferred to the buffered aqueous solution, occurred before or during the rate-determining step of the catalytic cycle.

Figure 14F:
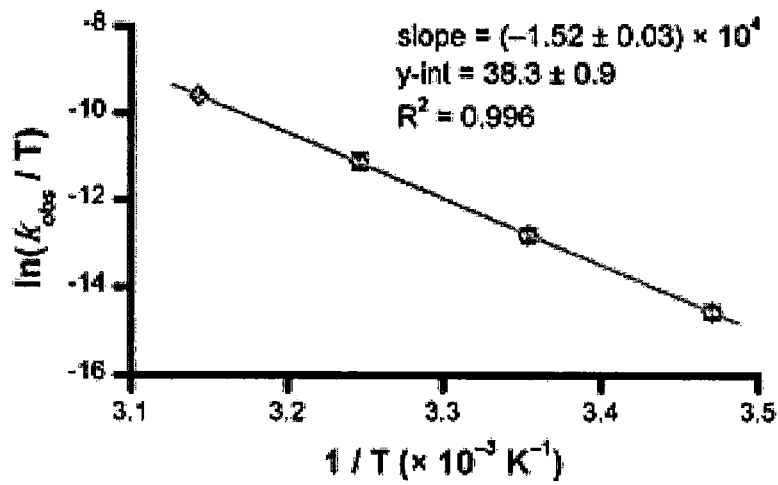
FIG. 14F shows a graph illustrating the dependence of observed rate constant ($k_{obs}$) for Ru1-catalyzed ABTS$^{•-}$ reduction on T=15, 25, 35 or 45° C. Each data point (◇) is the average of 4 experiments performed on 4 different days and the error bars represent the standard deviation. Conditions: [Ru1]$_0$=5 µM, [ABTS$^{•-}$]0=50 µM, [ABTS$^{2-}$]$_0$=100 µM, [EtOH]$_0$=50 mM, PBS (pH 7.4), 25° C.; absorbance measured at 734 nm (unless specified otherwise).

Given the results from the concentration studies, the Ru1-catalyzed reduction appeared to involve dissociation of H$^+$ and ABTS$^{2-}$ from as well as association of EtOH to Ru, although not necessarily in that order, leading up to or during the rate-determining step. To gain greater insight into the nature of the transition state for the rate-determining step, it was next examined the temperature dependence of Ru1-catalyzed ABTS$^{\cdot-}$ reduction. To PBS solutions of 5 μM Ru1 (CH$_3$CN stock), 50 μM ABTS$^{\cdot-}$ and 100 μM ABTS$^{2-}$ at various temperatures (15, 25, 35 or 45° C.) was added 50 mM EtOH, and the values of ln($k_{obs}$/T) were plotted against 1/T, which revealed a linear relationship (FIG. 14F). Using the linear form of the Eyring-Polanyi equation, the slope obtained from linear regression is equal to −ΔH$^\ddagger$/R and the y-intercept corresponds to ΔS$^\ddagger$/R+ln($k_B$/h). For the reduction of ABTS$^{\cdot-}$ to ABTS$^{2-}$ catalyzed by Ru1, the values determined for ΔH$^\ddagger$ and ΔS$^\ddagger$ were 30.3±0.5 kcal mol$^{-1}$ and 28.9±1.7 cal mo$^{-1}$ K$^{-1}$, respectively. The positive value for ΔS$^\ddagger$ revealed that the disorder in the system was increasing and thus suggested that dissociation of a ligand was occurring during the rate-determining step. In the transfer hydrogenation mechanism, the catalytically active metal-hydride species is formed when an alkoxide ligand undergoes β-hydride elimination and then the resulting aldehyde or ketone ligand dissociates from the metal, a process which increases the entropy of the system. Therefore, the positive value of ΔS$^\ddagger$ observed for the reduction of ABTS$^{\cdot-}$ to ABTS$^{2-}$ catalyzed by Ru1 was consistent with the generation of a ruthenium-hydride species during the rate-determining step.

Figure 15:
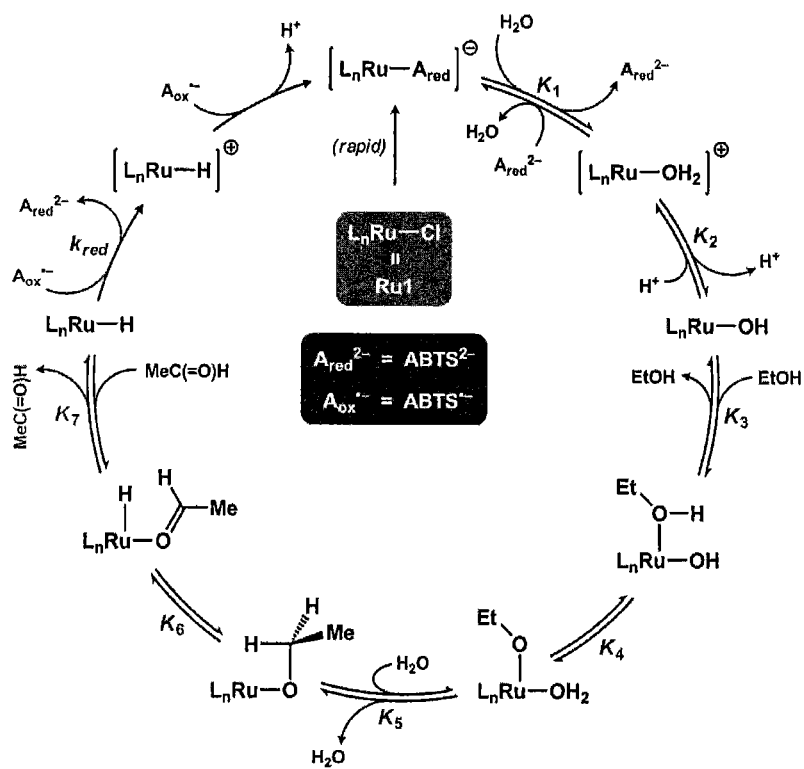
FIG. 15 shows a schematic of a proposed mechanism for Ru1-catalyzed conversion of ABTS$^{•-}$ to ABTS$^{2-}$ with EtOH as the terminal reductant. Text and arrows outside the cyclic scheme correspond to forward reactions (clockwise), whereas text and arrows inside the cyclic scheme correspond to reverse reactions (counter-clockwise). Each $K_n$ corresponds to the equilibrium constant for step "n" (i.e., $K_1$ for step 1, etc.).

Based on the results from the rate law studies, it was concluded that a ruthenium-hydride complex derived from Ru1 was the species that reduced ABTS$^{\cdot-}$, and, without wishing to be bound to any particular theory, it is proposed that the catalytically active ruthenium-hydride complex is formed via a transfer hydrogenation-like mechanism. Addition of Ru1 to a PBS solution containing ABTS$^{\cdot-}$ and ABTS$^{2-}$ results in rapid (with respect to turnover) substitution of the chloride ligand with ABTS$^{2-}$ to afford [L$_n$Ru-A$_{red}$]$^{1-}$ and begin the catalytic cycle (FIG. 15). In step 1, ABTS$^{2-}$ exchanges with H$_2$O ligand to yield a cationic aquo complex [L$_n$Ru—OH$_2$]$^{1+}$, and the necessity of ABTS$^{2-}$ dissociation is demonstrated by the linear relationship between $k_{obs}$ and 1/[ABTS$^{2-}$] (i.e., FIG. 14B). Dissociation of H$^+$ from [L$_n$Ru—OH$_2$]$^+$ to the buffer occurs in step 2 to produce a neutral hydroxo complex [L$_n$Ru—OH], which is supported by the inverse dependence of $k_{obs}$ on H$^+$ concentration (i.e., FIG. 14E). The linear correlation between $k_{obs}$ and concentration of EtOH (i.e., FIG. 14C) suggests that EtOH coordinates to [L$_n$Ru—OH] in step 3 to afford [(L$_n$Ru—OH).EtOH]. Breakage of the O—H bond in the EtOH ligand then occurs via intramolecular H$^+$ transfer to the hydroxo ligand and yields [(L$_n$Ru-OEt).H$_2$O] in step 4. In step 5, the aquo ligand in [(L$_n$Ru-OEt).H$_2$O] dissociates to form the alkoxide complex [L$_n$Ru-OEt]. Breakage of the carbinol C—H bond in the EtOH ligand then occurs via β-hydride elimination in step 6 to produce [(L$_n$Ru—H).MeC(=O)H], a ruthenium-hydride complex with an O-bound acetaldehyde. Subsequent dissociation of acetaldehyde in step 7 then affords the catalytically active ruthenium-hydride species [L$_n$Ru—H], which upon formation reacts with ABTS$^{\cdot-}$ in 1:1 stoichiometry with rate constant $k_{red}$, given that the rate of Ru1-catalyzed ABTS$^{\cdot-}$ reduction is first-order in ABTS$^{\cdot-}$ (i.e., FIG. 14A). Without wishing to be bound to any particular theory, it is proposed that [L$_n$Ru—H] undergoes one-electron oxidation upon reaction with 1 equiv. of ABTS$^{\cdot-}$, and the resulting Ru(III) species [L$_n$Ru—H]$^{1+}$ undergoes deprotonation, accompanied by one-electron oxidation with a second equiv. of ABTS$^{\cdot-}$, and binding by the resulting ABTS$^{2-}$ to regenerate [L$_n$Ru-A$_{red}$]$^{1-}$ and restart the cycle.

An alternative pathway could be invoked in which [L$_n$Ru—H] transfers a hydride (H$^-$) to an imine moiety in ABTS$^{\cdot-}$ to afford H-ABTS$^{\cdot 2-}$ but the experimental data do not support this pathway. Inner-sphere H$^-$ transfer, for example, would first require ABTS$^{\cdot-}$ to coordinate to [L$_n$Ru—H], but the rate law studies suggest that ABTS$^{\cdot-}$ binding is not competitive with ABTS$^{2-}$, which is also present in greater abundance (i.e., FIG. 14B). Any mechanism that involved H$^-$ transfer to an imine moiety in ABTS$^{\cdot-}$ would create a charge-separated species with decreased radical delocalization, features that would render H-ABTS$^{\cdot 2-}$ significantly higher in energy than either ABTS$^{\cdot-}$ or ABTS$^{2-}$. Because such an endergonic reaction would likely be slower than the formation of [L$_n$Ru—H], subsequent H$^-$ transfer to ABTS$^{\cdot-}$ would therefore be the rate-determining step. Once formed, H-ABTS$^{\cdot 2-}$ would then need to be oxidized by one equiv. of ABTS$^{\cdot-}$, and the rate of Ru1-catalyzed ABTS$^{\cdot-}$ reduction would thus appear to be second-order in ABTS$^{\cdot-}$ concentration: the rate-limiting formation of H-ABTS$^{\cdot 2-}$ would depend on [ABTS$^{\cdot-}$], and the reaction of H-ABTS$^{\cdot 2-}$ with ABTS$^{\cdot-}$ would also depend on [ABTS$^{\cdot-}$]. Because the observed rate of Ru1-catalyzed ABTS$^{\cdot-}$ reduction is instead first-order in [ABTS$^{\cdot-}$] (i.e., FIG. 14A), we can exclude hydride transfer to ABTS$^{\cdot-}$ as a possible step in the catalytic cycle.

Compared to H$^-$ transfer from [L$_n$Ru—H] to ABTS$^{\cdot-}$, one-electron oxidation of [L$_n$Ru—H] by ABTS$^{\cdot-}$ will likely have a lower activation energy and will thus occur before any hydride transfer could. Because the oxidation of [L$_n$Ru—H] by ABTS$^{\cdot-}$ occurs after the rate-determining step, direct observation of the subsequent intermediates is not possible, but the steps proposed to complete the catalytic cycle are consistent with the known properties of organo-ruthenium-hydride complexes. One-electron oxidation of [L$_n$Ru—H] by ABTS$^{\cdot-}$ will produce a cationic 17-electron Ru(III) complex, [L$_n$Ru—H]$^{1+}$, that will function as an H$^+$ source, not H$^-$, and will be deprotonated in the pH 7.4 PBS. The resulting coordinatively unsaturated, neutral 17-electron Ru(I) species, [L$_n$Ru], will then be trapped by an additional ligand L' from solution (e.g., H$_2$O) to generate [L$_n$Ru-L']. This 19-electron Ru(I) complex will be rapidly oxidized by ABTS$^{\cdot-}$ to afford a cationic Ru(II) complex and ABTS$^{2-}$, which will then combine to produce [L$_n$Ru-A$_{red}$]$^{1-}$ and complete the proposed catalytic cycle. Both the deprotonation of a ruthenium-hydride complex and generation of a radical, 19-electron Ru(I) species have significant literature precedent.

Tilset and Norton have shown that [RuH(η$^5$-C$_5$H$_5$)(PPh$_3$)$_2$](M1$_{red}$) undergoes one-electron oxidation at −0.34 V (vs. Fc$^{0/+}$) to form M1$_{ox}$, which has a p$K_a$ lower than M1$_{red}$ by 20-25 log units.[30,31] Because the ABTS$^{\cdot-}$/ABTS$^{2-}$ redox couple occurs at +0.28 V,[32] oxidation of M1$_{red}$ to M1$_{ox}$ by ABTS$^{\cdot-}$ would be thermodynamically favorable. Tilset and Norton also noted that deprotonation of M1$_{ox}$ thermodynamically uphill by 4 p$K_a$ units would proceed if the resulting neutral, Ru(I) conjugate base (M2$_{red}$) could subsequently be irreversibly oxidized. Because one-electron reduction of M2$_{ox}$ to M2$_{red}$ occurs at −2.42 V,[30] even a weak oxidant, such as [Co(η$^5$-C$_5$Me$_5$)$_2$]$^{1+}$ (E$_{1/2}$=−1.91 V),[33] would be able to convert M2$_{red}$ to M2$_{ox}$ and thus facilitate the deprotonation of M1$_{ox}$.

Compared to an $(\eta^5\text{-}C_5H_5)^{1-}$ ligand, $\mu^6$-cymene is less electron-donating, thus the oxidation of $[L_nRu\text{—}H]$ will likely occur at a higher potential than $M1_{red}$. Similar to $[L_nRu\text{—}H]$, $M3_{red}$ is a Ru-hydride complex containing an $\eta^6$-cymene ligand, and electrochemical analysis revealed $M3_{red}$ underwent irreversible oxidation to $M3_{ox}$ at $-0.24$ V.[34] Although the oxidation of $M3_{red}$ occurred at a potential 100 mV higher than $M1_{red}$, the value was still well below the $ABTS^{\cdot-}/ABTS^{2-}$ redox couple. Because the difference in oxidation potentials between $[L_nRu\text{—}H]$ and $M3_{red}$ is likely smaller than the difference between $M3_{red}$ and $M1_{red}$, $ABTS^{\cdot-}$ should be a sufficiently strong oxidant to be reduced by $[L_nRu\text{—}H]$ and afford $ABTS^{2-}$ and $[L_nRu\text{—}H]^{1+}$.

An extensive compendium of $pK_a$ values for Ru-hydride complexes have been measured, but there are fewer values available for cationic arene-Ru-hydride complexes. The complex most similar to $[L_nRu\text{—}H]^{1+}$ for which a $pK_a$ value has been reported is $[RuH(bpy)(\eta^6\text{-}C_6Me_6)]^{1+}$ ($M4_{red}$, $pK_a=22.5\pm0.1$ in $CH_3CN$)[35] and, using the method developed by Morris to estimate acidity in different solvents,[36] the $pK_a$ for $M4_{red}$ in $H_2O$ can be estimated at 15.9. Little deprotonation of $M4_{red}$ would occur in pH 7.4 buffer, but the $pK_a$ for $[L_nRu\text{—}H]^{1+}$ will be significantly lower than $M4_{red}$ given that the former contains Ru(III), whereas the latter contains Ru(II). A more relevant insight into the acidity of $[L_nRu\text{—}H]^{1+}$ would be the $pK_a$ for the one-electron oxidized Ru(III) species $M4_{ox}$. Using the observations of Tilset and Norton that one-electron oxidation lowers the $pK_a$ of a Ru-hydride complex by 20-25 units,[30,31] the $pK_a$ for $M4_{ox}$ in $H_2O$ can be estimated in the range of $-4.1$ to $-9.1$. Similarly drastic increases in acidity occur upon one-electron oxidation of $[RuH(\mu^5\text{-}C_5H_5)(CO)(PPh_3)]$ ($pK_a$ decreases to 4-5 from 27-28)[37] and $[WH(\eta^5\text{-}C_5H_5)(CO)_2]$ ($pK_a$ decreases to $-3$ from 16).[38]

Collectively, the results from the rate law studies suggested that $[L_nRu\text{—}H]$ was the catalytically active species for the reduction of $ABTS^{\cdot-}$ to $ABTS^{2-}$ and was formed via rate-determining $\beta$-hydride elimination from a Ru-ethoxide species. Based on the oxidation potentials for similar Ru-hydride complexes in the literature, $ABTS^{\cdot-}$ will be a sufficiently potent oxidant to oxidize $[L_nRu\text{—}H]$ to $[L_nRu\text{—}H]^{1+}$. Similarly, the $pK_a$ values for previously-reported neutral and cationic Ru(II) and Ru(III) hydrides suggested that pH 7.4 buffer will be sufficiently basic to deprotonate $[L_nRu\text{—}H]^{1+}$ and yield a neutral Ru(I) species. Subsequent oxidation by $ABTS^{\cdot-}$ will be even more favorable than $[L_nRu\text{—}H]$ for this Ru(I) intermediate, and the resulting Ru(II) complex and $ABTS^{2-}$ formed then combine to regenerate $[L_nRu\text{-}A_{red}]^{1-}$ and complete the catalytic cycle.

Figure 16:
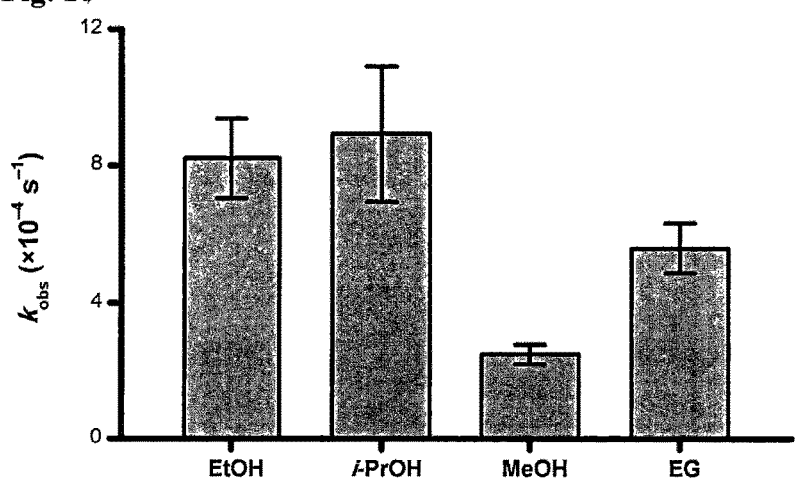
FIG. 16 shows a graph from a terminal reductant assay for ABTS$^{•-}$ reduction by Ru1. For each experiment, a PBS solution containing 5 µM Ru1 ($CH_3CN$ stock), 50 µM ABTS$^{•-}$ and 100 µM ABTS$^{2-}$ at 25° C. was treated with 50 mM of the terminal reductant candidate and the decay in absorbance at 734 nm was measured. Observed rate constants ($k_{obs}$) were extracted from slope of the plot of ln($A/A_0$) vs. time for the first 60 s following addition of the alcohol or ether. Conditions: [Ru1]$_0$=5 μM, [ABTS$^{·-}$]$_0$=50 μM, [ABTS$^{2-}$]$_0$=100 μM, 50 mM alcohol, PBS (pH 7.4), 25° C.; absorbance measured at 734 nm.

In the proposed mechanism, the key reducing species $[L_nRu\text{—}H]$ is generated via $\beta$-hydride elimination from an alkoxide ligand, therefore both the O—H and C—H groups in the CH—OH moiety may be a factor for reactivity. To test this hypothesis, a series of other molecules comprising (or lacking) these groups were then assayed to confirm the necessity of both for terminal reductant functionality. Addition of 50 mM i-PrOH, which comprises a CH—OH moiety, to a solution of 5 μM Ru1 ($CH_3CN$ stock), 50 μM $ABTS^{\cdot-}$ and 100 μM $ABTS^{2-}$ in PBS caused the absorbance at 734 nm to decay with an observed rate constant statistically similar to that measured with EtOH ($k_{iPrOH}$=8.92±1.96× $10^{-4}$ s$^{-1}$ vs. $k_{EtOH}$=8.21±1.14×$10^{-4}$ s$^{-1}$; FIG. 16). When 50 mM MeOH was added instead, the radical absorbance decreased significantly more slowly ($k_{MeOH}$=2.49±0.29× $10^{-4}$ s$^{-1}$) than with either EtOH or i-PrOH, but nonetheless faster than uncatalyzed $ABTS^{\cdot-}$ thermal decomposition.

The addition of varying concentrations of acetone (25, 50, 75, 100 mM) before the addition of 50 mM i-PrOH had no effect on the reaction rate. Because $\beta$-hydride elimination from a Ru-isopropoxide species (i.e., step 6, FIG. 15) would generate a Ru—H complex with an O-bound acetone ligand, and acetone dissociation must occur to form the catalytically active reducing species $[L_nRu\text{—}H]$ (i.e., step 7, FIG. 15), the concentration of acetone could have an impact on the reaction rate. However, because no change in reaction rate was observed when acetone was added before i-PrOH, it would appear that the dissociation of O-bound acetone occurs after the rate-determining step. It is therefore concluded that $\beta$-hydride elimination (i.e., step 6, FIG. 15) is the rate-determining step.

Figure 17:
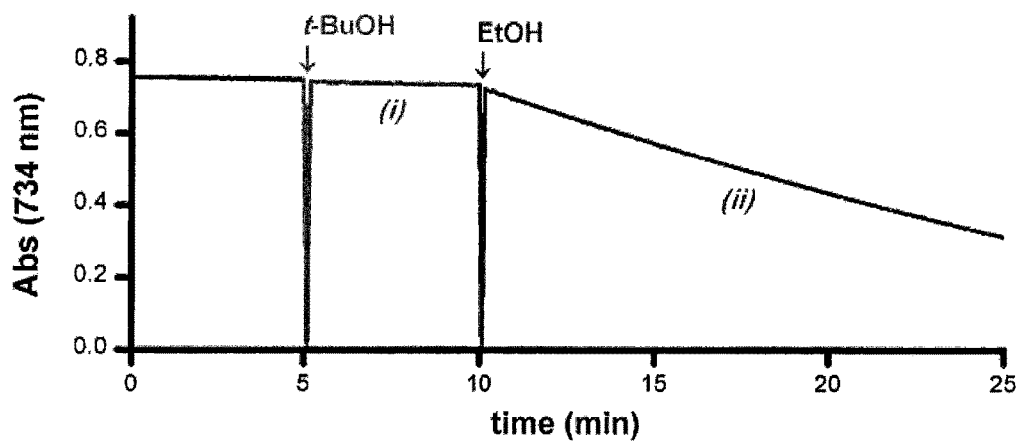
FIG. 17 shows a graph illustrating the necessity of having a non-tertiary alcohol for the catalytic reduction of ABTS$^{·-}$ by Ru1 in PBS. (i) By itself, ABTS$^{·-}$ is stable in the presence of Ru1 in PBS. (ii) Addition of t-BuOH did not afford ABTS$^{·-}$ degradation. (iii) Subsequent addition of EtOH caused the absorbance to decrease, which indicated that the lack of reactivity observed with t-BuOH was not due to catalyst deactivation but rather the fact that t-BuOH was not a competent terminal reductant. Conditions: [Ru1]$_0$=5 μM, [ABTS$^{·-}$]$_0$=50 μM, [ABTS$^{2-}$]$_0$=100 μM, 50 mM ROH, PBS (pH 7.4), 25° C.; absorbance measured at 734 nm.

Unlike the non-tertiary alcohols MeOH, EtOH and i-PrOH, t-BuOH lacks the C—H group of a CH—OH moiety and should therefore be unable to generate the Ru—H intermediate essential for $ABTS^{\cdot-}$ reduction (i.e., step 6, FIG. 15). In confirmation of this expectation, the addition of 50 mM t-BuOH to a PBS solution containing 5 μM Ru1 ($CH_3CN$ stock), 50 μM $ABTS^{\cdot-}$ and 100 μM $ABTS^{2-}$ afforded no change in radical absorbance (FIG. 17, i). Subsequent addition of 50 mM EtOH (FIG. 17, ii) caused $ABTS^{\cdot-}$ reduction to occur with the same rate constant as with EtOH alone (i.e., FIG. 16), which demonstrated that the absence of reactivity observed with t-BuOH was not due to catalyst deactivation but rather the inability of t-BuOH to undergo $\beta$-hydride elimination (i.e., step 6, FIG. 15) and form $[L_nRu\text{—}H]$.

Ethylene glycol (EG) and 1,2-dimethoxyethane (DME) were then assayed to elucidate the importance of the O—H group in the CH—OH moiety in Ru1-catalyzed $ABTS^{\cdot-}$ reduction. Consistent with the results using EtOH and i-PrOH, addition of 50 mM EG to a solution of 5 μM Ru1 ($CH_3CN$ stock), 50 μM $ABTS^{\cdot-}$ and 100 μM $ABTS^{2-}$ in PBS caused the absorbance at 734 nm to decrease, with an observed rate constant ($k_{EG}$=5.61±0.73×$10^{-4}$ s$^{-1}$) slower than EtOH or i-PrOH, but not significantly so given the standard deviations (FIG. 16). In contrast, the addition of 50 mM DME to a PBS solution of 5 μM Ru1 ($CH_3CN$ stock), 50 μM $ABTS^{\cdot-}$ and 100 μM $ABTS^{2-}$ did not afford any radical degradation, which indicated that the O—H group in the CH—OH moiety was essential for terminal reductant functionality. Without this O—H group, DME cannot form the Ru-alkoxide species (i.e., step 4, FIG. 15) that precedes $\beta$-hydride elimination (i.e., step 6, FIG. 15) and, furthermore, renders $\beta$-hydride elimination energetically inaccessible as it would result in the formation of an O-methylated aldehyde with a formal positive charge on the oxygen that would also be coordinated to Ru with its last remaining electron pair. Clearly, both the C—H and O—H groups of a CH—OH moiety are necessary for terminal reductant function.

TABLE 4

Activation parameters for Ru1-catalyzed $ABTS^{\cdot-}$ reduction with various terminal reductants

| | $\Delta H^{\dagger}$ | $\Delta S^{\ddagger}$ | $E_a$ | ln(A) |
|---|---|---|---|---|
| EtOH | 30.3 ± 0.5 | 28.9 ± 1.7 | 30.9 ± 0.5 | 45.0 ± 0.9 |
| i-PrOH | 31.2 ± 0.7 | 32.2 ± 2.3 | 31.8 ± 0.7 | 46.7 ± 1.1 |
| EG | 31.7 ± 0.6 | 32.8 ± 2.1 | 32.3 ± 0.6 | 47.0 ± 1.0 |
| MeOH | 25.8 ± 0.9 | 11.4 ± 2.9 | 26.4 ± 0.9 | 36.2 ± 1.5 |

Values reported as the average ± standard deviation of 4 experiments performed on 4 different days with units of $10^{-5}$ s$^{-1}$. Protio and deutero alcohol stock solutions (5M) were prepared in $H_2O$ and $D_2O$ to match the buffered solution for the experiment.

For the alcohols that did enable Ru1-catalyzed ABTS$^{\cdot-}$ reduction (i.e., EtOH, i-PrOH, MeOH, and EG), potential origins of their differing observed rate constants were explored. Therefore, values of $k_{obs}$ were obtained via addition of 50 mM alcohol (EtOH, i-PrOH, MeOH, or EG) to PBS solutions containing 5 µM Ru1 (CH$_3$CN stock), 50 µM ABTS$^{\cdot-}$ and 100 µM ABTS$^{2-}$ at various temperatures (15, 25, 35 or 45° C.). Plotting $\ln(k_{obs}/T)$ and $\ln(k_{obs})$ vs. 1/T enabled use of the linear forms of the Eyring-Polanyi and Arrhenius equations, respectively, to determine the values of $\Delta H^{\ddagger}$, $\Delta S^{\ddagger}$, $E_a$ and $\ln(A)$ (where $E_a$ and A correspond to the activation energy and pre-exponential factor in units of kcal mol$^{-1}$ and s$^{-1}$, respectively), which are listed in Table 4.

The Ru1-catalyzed reduction of ABTS$^{\cdot-}$ in the presence of each non-tertiary alcohol exhibited a positive value for $\Delta S^{\ddagger}$, which would be expected if β-hydride elimination were occurring from a Ru-alkoxide species via a process similar to EtOH (i.e., step 6, FIG. 15). Consistent with the nearly identical values of $k_{obs}$ measured for EtOH and i-PrOH, each of the parameters ($\Delta H^{\ddagger}$, $\Delta S^{\ddagger}$, $E_a$ and $\ln(A)$) calculated for EtOH and i-PrOH were statistically indistinguishable. Similarly, the slightly (but still statistically significant) slower reactivity observed with EG vs. EtOH was reflected by the slightly higher $\Delta H^{\ddagger}$ (31.7±0.6 kcal mol$^{-1}$) and $E_a$ (32.3±0.6 kcal mol$^{-1}$) values for EG compared to EtOH ($\Delta H^{\ddagger}$=30.5±0.6 kcal mol$^{-1}$ and $E_a$=30.9±0.5 kcal mol$^{-1}$). Although MeOH afforded exhibited the lowest $\Delta H^{\ddagger}$ and $E_a$ values of all the non-tertiary alcohols tested, it afforded the slowest ABTS$^{\cdot-}$ reduction, possibly because $\Delta S^{\ddagger}$ and $E_a$ were the least favorable. Ultimately, the usefulness of comparing the different transition state or activation parameters is limited by the fact that substitution of one non-tertiary alcohol for another will impact multiple steps in the catalytic cycle and in multiple ways, particularly steps 4 and 6.

TABLE 5

Activation parameters for Ru1-catalyzed ABTS$^{\cdot-}$ reduction with various terminal reductants

| | p$K_a$ | $K_a$ | $\Delta G_r^{\circ}$ | $K_r$ | $K_a \times K_r$ |
|---|---|---|---|---|---|
| EtOH | 15.9 | 1.26 × 10$^{-16}$ | 7.27 | 4.71 × 10$^{-6}$ | 5.93 × 10$^{-22}$ |
| i-PrOH | 16.5 | 3.16 × 10$^{-17}$ | 4.96 | 2.33 × 10$^{-4}$ | 7.37 × 10$^{-21}$ |
| EG | 14.22 | 6.03 × 10$^{-15}$ | 12.8 | 4.30 × 10$^{-10}$ | 2.59 × 10$^{-24}$ |
| MeOH | 15.5 | 3.16 × 10$^{-16}$ | 14.3 | 3.57 × 10$^{-11}$ | 1.13 × 10$^{-26}$ |

Units for $K_a$, $K_r$, $K_a \times K_r$ are M, M, M$^2$ and kcal mol$^{-1}$, respectively. Values for $\Delta G_r^{\circ}$ calculated using the formula $\Delta G_r^{\circ} = \Delta H_r^{\circ} - T\Delta S_r^{\circ}$ for the dehydrogenation of R$_1$—CHOH—R$_2$ to R$_1$—C(=O)—R$_2$ + ½ H$_2$. Values for $\Delta H_r^{\circ}$ and $\Delta S_r^{\circ}$ estimated from the equations $\Delta H_r^{\circ} = \Delta H_f^{\circ}$(R$_1$—C(=O)—R$_2$) − $\Delta H_f^{\circ}$(R$_1$—CHOH—R$_2$) and $\Delta S_r^{\circ} = ½$ S$^{\circ}$(H$_2$) + S$^{\circ}$(R$_1$—C(=O)—R$_2$) − S$^{\circ}$(R$_1$—CHOH—R$_2$) for reported as the average ± standard deviation of 4 experiments performed on 4 different days with units of 10$^{-5}$ s$^{-1}$. Protio and deutero alcohol stock solutions (5M) were prepared in H$_2$O and D$_2$O to match the buffered solution for the experiment.

Increasing the acidity of the O—H proton in a non-tertiary alcohol will render the intramolecular deprotonation in step 4 more thermodynamically favorable and thus the corresponding equilibrium constant in step 4 ($K_4$) will be larger. Conversely, a thermodynamically more favorable alcohol dehydrogenation will make the corresponding equilibrium constant in step 6 ($K_6$) larger. Based on the published p$K_a$ and $\Delta Gr^{\circ}$ values for the non-tertiary alcohols, the product of the corresponding $K_a$ and $K_r$ values gives a relative ordering that is consistent with the observed rate constants presented in FIG. 16 (Table 5).

Intramolecular proton transfer from the OH Considering only $E_a$, MeOH would be expected to afford the fastest reactivity, but the ln(A) for MeOH is nearly 10 units lower than the other alcohols investigated, which indicated that the pre-exponential factor was dominant, similar to the behavior observed with i-PrOH. The relative ordering of the $\Delta H^{\ddagger}$ and $E_a$ values for MeOH<EtOH<i-PrOH matches the trend for the enthalpy of dehydrogenation,[39] in which the formation of formaldehyde is more unfavorable than the formation of acetaldehyde, which is in turn more unfavorable than the formation of acetone.

Collectively, the results from the terminal reductant assay demonstrate that both the OH and CH groups of the CH—OH moiety in a non-tertiary alcohol are necessary for the conversion of ABTS$^{\cdot-}$ to ABTS$^{2-}$ by Ru1. These factors reflect the fact that the catalytically active reducing species [L$_n$Ru—H] must be formed via β-hydride elimination from the carbinol position of a metal-bound alkoxide ligand. An alcohol lacking a carbinol C—H group cannot undergo β-hydride elimination because it lacks a β-hydrogen, and a molecule lacking an O—H group cannot form the necessary alkoxide precursor for β-hydride elimination to occur.

To confirm that breakage of the C—H and O—H bonds in the CH—OH moiety of a non-tertiary alcohol was occurring during or before the rate-determining step of the catalytic reduction of ABTS$^{\cdot-}$ by Ru1, rate constants were measured using a combination of protio and deutero EtOH and i-PrOH in protio and deutero PBS, the results of which are listed in Table 6. By performing measurements using protio alcohols in deutero PBS and deutero alcohols in protio PBS, it was possible to generate the mixed isotope CH—OD and CD-OH alcohols, respectively. With both EtOH and i-PrOH, significantly slower ABTS$^{\cdot-}$ reduction was observed upon substitution of either the C—H or O—H group with C-D or O-D, and the doubly substituted CD-OD alcohols afforded the slowest reactivity.

TABLE 6

Observed rate constants for Ru1-catalyzed ABTS$^{\cdot-}$ reduction with protio and deutero alcohols in protio and deutero PBS

| | PBS (H$_2$O) | PBS (D$_2$O) |
|---|---|---|
| EtOH | 6.69 ± 0.73 | 1.31 ± 0.11 |
| EtOH-d$_6$ | 1.33 ± 0.22 | 0.454 ± 0.020 |
| i-PrOH | 9.43 ± 1.26 | 1.31 ± 0.12 |
| i-PrOH-d$_8$ | 1.92 ± 0.26 | 0.457 ± 0.024 |

Values reported as the average ± standard deviation of 4 experiments performed on 4 different days with units of 10$^{-5}$ s$^{-1}$. Protio and deutero alcohol stock solutions (5M) were prepared in H$_2$O and D$_2$O to match the buffered solution for the experiment.

Quantifying the effect of the C—H/C-D and O—H/O-D bond substitutions could be achieved by examining the ratios of the observed rate constants (Table 7). Although these ratios would normally correspond to the kinetic isotope effects of the deuterium substitution, it will be shown that an additional factor is present that must be abstracted to obtain the true values. Replacing the C—H (but not the O—H) bond with C-D results in a reaction that is 5.05±1.02 times slower with EtOH and 4.93±0.93 times slower with i-PrOH in protio PBS. However, when the same substitution was performed in deutero PBS, the kobs values for EtOH and i-PrOH were 2.88±0.27 and 2.86±0.31 times slower, respectively, for the C-D compared to C—H alcohols. Because these two sets of experiments involved the same C—H for C-D bond substitution, without changing the O—H or O-D groups, their results should have been statistically similar.

TABLE 7

Ratio of observed rate constants based on C—H/C—D and
O—H/O—D isotopic substitution in protio and deutero PBS.

|  | X = H | X = D |
|---|---|---|
| CH$_3$CH$_2$OX/ CD$_3$CD$_2$OX (C—H/C—D for EtOH) | 5.05 ± 1.02 | 2.88 ± 0.27 |
| (CH$_3$)$_2$CHOX/ (CD$_3$)$_2$CDOX (C—H/C—D for i-PrOH) | 4.93 ± 0.93 | 2.86 ± 0.31 |
| CX$_3$CX$_2$OH/ CX$_3$CX$_2$OD (O—H/O—D for EtOH) | 5.13 ± 0.71 | 2.92 ± 0.51 |
| (CX$_3$)$_2$CXOH/ (CX$_3$)$_2$CXOD (O—H/O—D for i-PrOH) | 7.21 ± 1.18 | 4.18 ± 0.60 |

Values reported as the average ± standard deviation.

Similar behavior was observed in the O—H/O-D substitution results. Replacing the O—H bond in the all-protio EtOH and i-PrOH with O-D caused ABTS$^{•-}$ reduction to occur 5.13±0.71 and 7.21±1.18 times more slowly, respectively. However, replacing the O-D bond in EtOH-d$_6$ or i-PrOH-d$_8$ with O—H increased the respective k$_{obs}$ values by a factor of 2.92±0.51 or 4.18±0.60. These two sets of experiments should have given statistically similar results, given that they involved the same O—H for O-D bond substitution without changing the C—H or C-D groups. Notably, the C—H/C-D and O—H/O-D ratios were greater when comparing a value obtained in protio PBS to a value obtained in deutero PBS, which indicated that the solvent played an important role in the reaction mechanism. Many of the steps in the proposed mechanism (FIG. 15) involve H$_2$O: displacement of ABTS$^{2-}$ by H$_2$O in step 1, deprotonation of the H$_2$O coordinated to Ru in step 2, intramolecular H$^+$ transfer from the Ru-bound EtOH to hydroxide in step 4, and dissociation of H$_2$O to generate an open coordination site necessary for β-hydride elimination in step 5. Replacing H$_2$O with D$_2$O would affect the equilibrium constants for each of these steps, thus it is unsurprising that a substantial solvent isotope effect would be observed for Ru1-catalayzed reduction of ABTS$^{•-}$ with non-tertiary alcohols.

TABLE 8

Kinetic isotope effects.

| KIE | EtOH | i-PrOH |
|---|---|---|
| solvent | 1.76 ± 0.39 | 1.72 ± 0.37 |
| C—H | 2.88 ± 0.27 | 2.86 ± 0.31 |
| O—H | 2.92 ± 0.51 | 4.18 ± 0.60 |
| C—H × O—H | 8.41 ± 1.67 | 11.98 ± 2.14 |
| CH—OH in H$_2$O/ CD—OD in D$_2$O | 14.7 ± 1.7 | 20.6 ± 3.0 |

Dividing each C—H/C-D ratio obtained in protio PBS by the corresponding ratio obtained in deutero PBS enabled calculation of the solvent isotope effects, which were 1.76±0.39 in the EtOH experiments and 1.72±0.37 in the i-PrOH experiments (Table 8). The fact that these numbers were similar for the independently performed EtOH and i-PrOH experiments supported their assignment as solvent isotope effects rather than some other unidentified experimental phenomenon. Having calculated the solvent isotope effect values, it was then possible to determine the kinetic isotope effects for deuterium substitution of the individual C—H and O—H groups in the CH—OH moieties in EtOH (2.88±0.27 and 2.92±0.51, respectively) and i-PrOH (2.86±0.31 and 4.18±0.60, respectively), values which were unambiguous for primary kinetic isotope effects,[40] which indicated that C—H or O—H bond breakage occurred before or during the rate determining step.

The C—H/C-D kinetic isotope effect value determined for i-PrOH in the Ru1-catalyzed reduction of ABTS$^{•-}$ (2.86±0.31) was identical to the corresponding C—H/C-D value reported by Casey (2.86±0.20) for H$_2$ transfer from i-PrOH to [Ru(S,S-TsDPEN)(η$^6$-cymene)].[41] A comparable C—H/C-D value (2.57±0.26) was observed by Bäckvall for the transfer of H$_2$ from 1-(4-fluorophenyl)ethanol to another organoruthenium complex similar to Ru1 and [Ru(S,S-TsDPEN)(η$^6$-cymene)].[42] The C—H/C-D kinetic isotope effect value for EtOH in Ru1-catalyzed reduction of ABTS$^{•-}$ (2.88±0.27) was statistically indistinguishable from i-PrOH and consistent with the findings by Casey and Bäckvall.

The catalytic reduction of ABTS$^{•-}$ by Ru1 exhibited significantly larger O—H/O-D kinetic isotope effect values for i-PrOH (4.18±0.60) and EtOH (2.92±0.51) than O—H/ O-D kinetic isotope effect values reported by Casey (1.79±0.07) and Bäckvall (1.87±0.17) with transfer hydrogenation reactions catalyzed by organoruthenium complexes. One possible explanation for such a large difference is that ABTS$^{•-}$ reduction by Ru1 and a non-tertiary alcohol formally involved ionic H$^+$ transfer from the O—H group to the Ru-bound hydroxide in a distinct step, whereas the systems studied by Casey and Bäckvall proceeded via concerted H$_2$ transfer from the non-tertiary alcohol CH—OH moiety to the catalyst. The difference between the O—H/O-D values for EtOH and i-PrOH during Ru1-catalyzed ABTS$^{•-}$ reduction (2.92±0.51 vs. 4.18±0.60, respectively) could be a consequence of the greater acidity of EtOH compared to i-PrOH (pKa=15.9 vs. 16.5, respectively), and the lower activation barrier this would produce for EtOH would render the ionic O—H bond breakage less sensitive to substitution with deuterium.

Having obtained unambiguous evidence that Ru1 catalyzes radical degradation, it was then sought to ascertain if Ru1 could also inhibit radical formation. Horseradish peroxidase (HRP) converts H$_2$O$_2$ to 2 equiv. of H$_2$O via HO$^•$, with concomitant consumption of 2e$^-$ and 2H$^+$ in each turnover. Because ABTS$^{2-}$ can serve as a 1e$^-$ reductant in this reaction, the rate of radical formation can be quantified by measuring the absorbance of ABTS$^{•-}$ vs. time.[43] Addition of 10 μM H$_2$O$_2$ to a PBS solution of 5 μM Ru1 (DMSO stock), 10 nM HRP and 50 μM ABTS$^{2-}$ caused the absorbance at 734 nm to increase, with an initial rate of ABTS$^{•-}$ formation (v$_0$) of 2.17±0.35×10$^{-8}$ M s$^{-1}$ (FIG. 18A, grey line), but significantly more slowly than with HRP alone (v$_0$=3.69±0.14×10$^{-8}$ M s$^{-1}$). After 12.8±0.7 min, the concentration of ABTS$^{•-}$ peaked at 8.71±0.55 μM and then began to decrease, indicating that radical degradation overtook radical formation, at an initial rate of decay (v$_0$') of 5.06±0.26×10$^{-9}$ M s$^{-1}$, which led to complete radical degradation within 60 min. To determine if the decreased rate of ABTS$^{•-}$ formation observed with Ru1 was caused by DMSO from the stock solution, 10 M H$_2$O$_2$ was added to 10 nM HRP and 50 μM ABTS$^{2-}$ in PBS containing 1% DMSO (same as 30 μL aliquot from Ru1 stock solution), resulting in a slightly slower rate of ABTS$^{•-}$ formation (v$_0$=3.24±0.11×10$^{-8}$ M s$^{-1}$) than HRP alone. Because DMSO only slightly inhibited the rate of ABTS$^{•-}$ formation and nonetheless permitted complete oxidation of ABTS$^{2-}$, the significantly lower value of $v_0$ and the final ABTS$^{\bullet-}$ concentration of zero observed in the presence of Ru1 can be attributed to the radical reducing ability of Ru1 and not DMSO from the stock solution.

Figure 13:
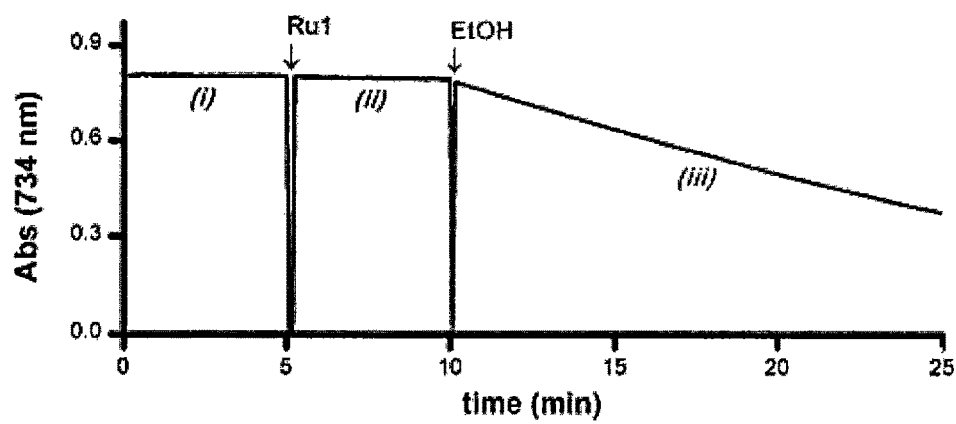
FIG. 13 shows a graph illustrating the catalytic reduction of ABTS$^{•-}$ by Ru1 in PBS. (i) By itself, ABTS$^{•-}$ is stable in PBS. (ii) Addition of Ru1 from a $CH_3CN$ stock solution did not cause ABTS$^{•-}$ degradation. (iii) Subsequent addition of EtOH caused the absorbance to decrease, which indicated that EtOH functioned as a terminal reductant. Conditions: [Ru1]$_0$=5 µM, [ABTS$^{•-}$]$_0$=50 µM, [ABTS$^{2-}$]$_0$=100 µM, 50 mM EtOH, PBS (pH 7.4), 25° C.; absorbance measured at 734 nm.
Figure 18A:
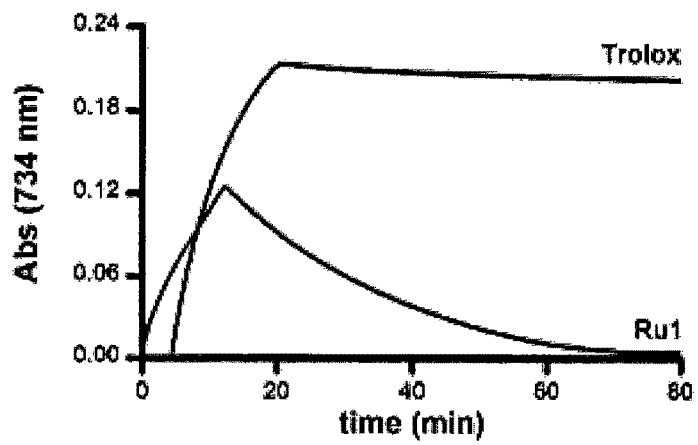
FIG. 18A shows a graph of in situ oxidation of ABTS$^{2-}$ to ABTS$^{·-}$ via HRP and $H_2O_2$ in the presence of 5 μM Ru1 (grey line) or 5 μM Trolox (black line). Conditions: [ABTS$^{2-}$]$_0$=20 μM, [Ru1]$_0$=5 μM, [HRP]$_0$=10 μM, [$H_2O_2$]$_0$=10 μM, 1% DMSO in PBS (pH 7.4) at 25° C.; absorbance measured at 734 nm.

In contrast to the experiments with Ru1, the addition of 10 μM $H_2O_2$ to a PBS solution of 5 μM Trolox (DMSO stock), 10 nM HRP and 50 μM ABTS$^{2-}$ resulted in no change in absorbance at 734 nm for the first 4.2±0.4 min, indicating that Trolox completely halted ABTS$^{\bullet-}$ formation (FIG. 18A, black line). After 4.2±0.4 min, however, the absorbance at 734 nm began to increase with $v_0=3.44\pm0.11\times10^{-8}$ M s$^{-1}$ and ABTS$^{\bullet-}$=concentration reached a maximum of 15.06±0.04 μM at t=22.0±0.5 min (i.e., 75% net oxidation of ABTS$^{2-}$; the subsequent decline is due to normal ABTS$^{\bullet-}$ thermal decay). The fact that only 75% of the initial 20 μM ABTS$^{2-}$ was oxidized in the presence of 5 μM Trolox indicates that Trolox is consuming 5 μM HO$^{\bullet}$ formed by HRP. Although Trolox functions as a 2e$^-$ reductant in EtOH solution (c.f. FIG. 13), it is because the first and second 1e$^-$ oxidations occur effectively in one step.[25] In basic solutions (e.g., buffered aqueous media), TrO$^{\bullet}$ is thermodynamically stable[44] and the second 1e$^-$ oxidation to TrO$^+$ is well-separated from the first.[25] Interestingly, the initial rate of ABTS$^{\bullet-}$ formation in the presence of Trolox is not statistically significantly different from the rate measured in the presence of DMSO or HRP alone, indicating that no inhibition of ABTS$^{\bullet-}$ formation occurred after 4.2 min and demonstrating that the antioxidant capacity of Trolox had been exhausted.

Figure 18B:
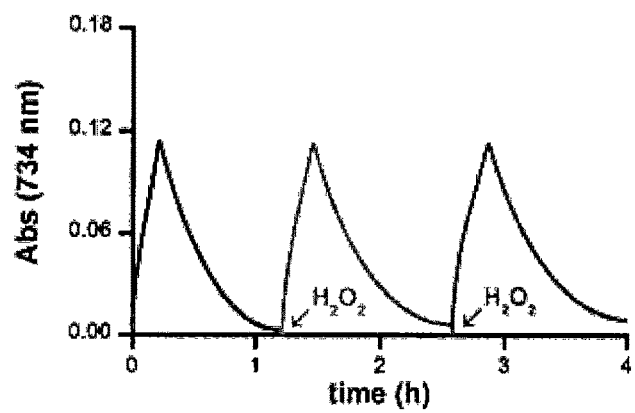
FIG. 18B shows a graph of ABTS$^{·-}$ formation by HRP in the presence of 5 μM Ru1, followed by two additional aliquots of 10 μM $H_2O_2$ (grey lines). Conditions: [ABTS$^{2-}$]$_0$=20 μM, [Ru1]$_0$=5 μM, [HRP]$_0$=10 nM, [$H_2O_2$]$_0$=10 μM, 1% DMSO in PBS (pH 7.4) at 25° C.; absorbance measured at 734 nm.

To determine if Ru1 remained catalytically competent after the complete reduction of ABTS$^{\bullet-}$ formed by 10 nM HRP and 10 μM $H_2O_2$ (FIG. 18B), two additional 10 μM aliquots of $H_2O_2$ were introduced. Addition of the second 10 μM aliquot of $H_2O_2$ caused the absorbance at 734 nm to increase ($v_0=2.06\times10^{-8}$ M s$^{-1}$; FIG. 18B) to a maximum ABTS$^{\bullet-}$ concentration of 7.73 μM at 14.8 min, followed by a decrease ($v_0'=4.85\times10^{-9}$ M s$^{-1}$) that led to complete radical reduction 66.7 min after the peak. Similarly, the third 10 μM aliquot of $H_2O_2$ resulted in ABTS$^{\bullet-}$ formation ($v_0=1.83\times10^{-8}$ M s$^{-1}$; FIG. 18B) that reached a maximum at 17.3 min (7.73 μM) before decreasing ($v_0'=4.26\times10^{-9}$ M s$^{-1}$) and resulting in complete reduction 66.5 min later.

Because the values measured for the initial rate of ABTS$^{\bullet-}$ formation, time to peak absorbance, maximum ABTS$^{\bullet-}$ concentration, initial rate of ABTS$^{\bullet-}$ reduction and final ABTS$^{\bullet-}$ concentration (i.e., zero) were highly conserved among the three sequential 10 μM $H_2O_2$ aliquots, it is evident that the ability of Ru1 to inhibit the formation of and catalyze the degradation of radicals is retained throughout the course of the experiment. Moreover, adding multiple sequential $H_2O_2$ aliquots confirmed the hypothesis that the decrease in absorbance at 734 nm was due to the reduction of ABTS$^{\bullet-}$ to ABTS$^{2-}$ rather than some other chemical reaction.

Figure 18C:
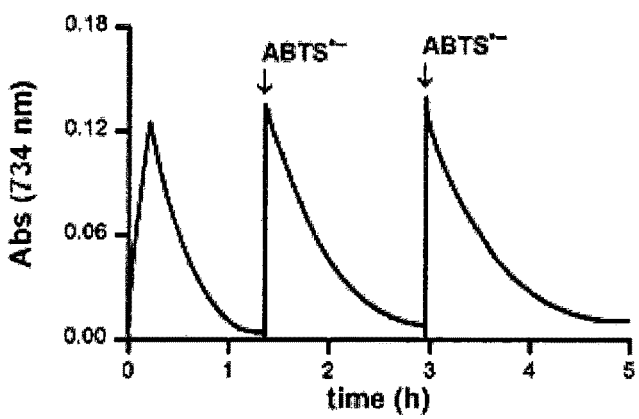
FIG. 18C shows a graph of ABTS$^{·-}$ formation by HRP in the presence of 5 μM Ru1, followed by two additional aliquots of 10 μM chemically synthesized ABTS$^{·-}$ (grey lines). Conditions: [ABTS$^{2-}$]$_0$=20 μM, [Ru1]$_0$=5 μM, [HRP]$_0$=10 nM, [$H_2O_2$]$_0$=10 μM, 1% DMSO in PBS (pH 7.4) at 25° C.; absorbance measured at 734 nm.

Chemically synthesized ABTS$^{\bullet-}$ aliquots were added in a similar manner to obtain greater insight into the ability of Ru1 to degrade vs. inhibit the formation of radicals. After the ABTS$^{\bullet-}$ formed by 10 nM HRP and 10 μM $H_2O_2$ was completely reduced by Ru1 (FIG. 18C), a 10 μM aliquot of chemically synthesized ABTS$^{\bullet-}$ was added (immediately increasing absorbance at 734 nm) that began to decay ($v_0'=3.41\times10^{-9}$ M s$^{-1}$) and complete reduction was attained within 95.7 min (FIG. 18C). Similarly, the second 10 μM aliquot of ABTS$^{\bullet-}$ underwent reduction ($v_0'=3.55\times10^{-9}$ M s$^{-1}$) that was complete 96.5 min later (FIG. 18C). Initial rates of decay and times to complete reduction with chemically synthesized ABTS$^{\bullet-}$ were slower than with $H_2O_2$, possibly because the ABTS$^{2-}$ concentration increased with each added aliquot in the former experiment but was constant throughout the latter.

An organoruthenium complex supported by a chelating anionic N-heterocyclic carbene ligand, Ru1, catalyzed the reduction of ABTS$^{\bullet-}$ to ABTS$^{2-}$ in EtOH with 100 turnovers. No reduction of ABTS$^{\bullet-}$ was observed in PBS, providing evidence that Ru1 itself cannot provide the necessary reducing equivalents. Subsequent addition of a non-tertiary alcohol ($R_1$—CHOH—$R_2$), however, caused ABTS$^{\bullet-}$ reduction, with both the C—H and the O—H groups of the —CHOH— moiety being necessary to function as a terminal reductant.

Substitution of $R_1$—CHOH—$R_2$ with $R_1$—CDOD-$R_2$ significantly decreased the observed reaction rate constants, with corresponding primary kinetic isotope effect values consistent with concerted $H_2$ transfer from the non-tertiary alcohol to the Ru complex in the rate-determining step. Furthermore, the values obtained with Ru1 closely match those previously reported from mechanistic studies of transfer hydrogenation reactions catalyzed by other organoruthenium complexes. In addition, Ru1 inhibited the oxidation of ABTS$^{2-}$ to ABTS$^{\bullet-}$ by HO$^{\bullet}$ and then reduced all of the ABTS$^{\bullet-}$ formed, demonstrating that Ru1 can inhibit the formation of radicals as well as catalyze their degradation. Collectively, our findings unambiguously demonstrate that transfer hydrogenation catalytic activity can be harnessed for the reduction of radicals in aqueous solution using a variety of non-tertiary alcohols as the terminal electron sources.

Example 4

Figure 19A:
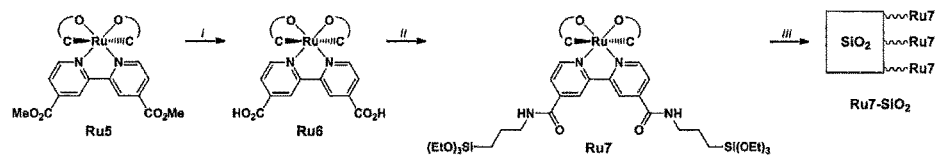
FIG. 19A shows the synthesis of Ru7-SiO$_2$. Conditions: (i) 10 equiv. NaOH, MeOH, Δ, 16 h; (ii) 3 equiv. N,N'-dicyclohexyl-carbodiimide, 3 equiv. N-hydroxysuccinimide, CH$_2$Cl$_2$, r.t., 16 h, then 3 equiv. APTES, 3 equiv. Et$_3$N, r.t., 16 h; (iii) SiO$_2$, toluene, 50° C., 2 h, then r.t., 15 h; (iv) 2.2 equiv. R—C≡C—H, 10 mol % [Pd(PPh$_3$)$_4$], 5 mol % CuI, THF/Et$_3$N, 90° C., 48 h; (v) 25 equiv. MMA, 1 mol % (PhCO$_2$)$_2$, THF, 50° C., 20 h.
Figure 19B:
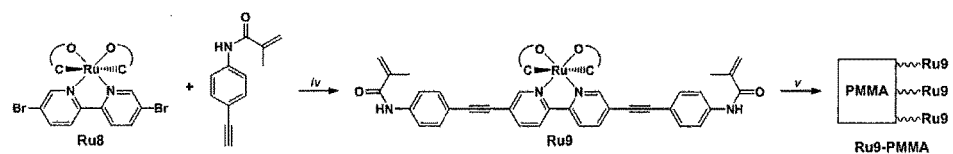
FIG. 19B shows the synthesis of Ru9-PMMA. Conditions: (i) 10 equiv. NaOH, MeOH, Δ, 16 h; (ii) 3 equiv. N,N'-dicyclohexyl-carbodiimide, 3 equiv. N-hydroxysuccinimide, CH$_2$Cl$_2$, r.t., 16 h, then 3 equiv. APTES, 3 equiv. Et$_3$N, r.t., 16 h; (iii) SiO$_2$, toluene, 50° C., 2 h, then r.t., 15 h; (iv) 2.2 equiv. R—C≡C—H, 10 mol % [Pd(PPh$_3$)$_4$], 5 mol % CuI, THF/Et$_3$N, 90° C., 48 h; (v) 25 equiv. MMA, 1 mol % (PhCO$_2$)$_2$, THF, 50° C., 20 h.
Figure 19C:
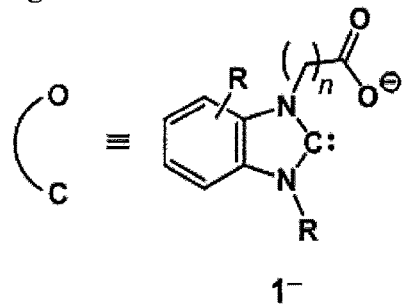
FIG. 19C shows the structure of the abbreviated structure for the ligand 1$^-$.

Experiments were performed to determine if covalent incorporation of an AIM into an organic polymer or inorganic material would endow that AIM with the ability to catalytically degrade radicals. Complexes Ru5 and Ru8 were thus prepared, using the procedure developed for Ru2,[19] to obtain suitable starting materials that could be derivatized with the functional groups necessary for covalent incorporation into $SiO_2$ and PMMA, respectively (FIG. 19). Hydrolysis of the $CO_2$Me groups in Ru5 to produce Ru6 was followed by amide coupling with 3-aminopropyltriethoxysilane (APTES)[48] to yield Ru7, which was then affixed[49] to the surface of $SiO_2$ microspheres (1.5 μm, Corpuscular Inc.) to afford Ru7-$SiO_2$, the desired SRAC-functionalized inorganic material. Scanning electron microscopy (SEM) revealed that the average diameter and surface roughness of Ru7-$SiO_2$ were not significantly different from the unfunctionalized microspheres, demonstrating that the material properties of $SiO_2$ were not adversely affected by incorporation of Ru7. Sonogashira coupling of N-methacroyl-4-ethynylaniline[50] to Ru8 yielded Ru9, which was then polymerized with methylmethacrylate (MMA)[51] to produce Ru9-PMMA (Mn=24.2 kDa, PDI=2.6), the desired SRAC-functionalized organic polymer. Atomic force microscopy (AFM) of thin films (spin-cast from 10 mg mL$^{-1}$ solutions in THF) of Ru9-PMMA and PMMA (prepared in the absence of Ru9) revealed nearly identical film thickness and surface roughness values, indicating that Ru9 did not interfere with the polymerization of MMA. Diffuse reflectance and film transmission UV/vis spectra of Ru7-$SiO_2$ and Ru9-PMMA displayed peaks at 523 nm and 565 nm, respectively, which were similar to the values observed with Ru7 and Ru9. These observations provided evidence that the Ru—NHC complexes had been incorporated into $SiO_2$ and PMMA without significant changes in electronic properties or coordination chemistry, consistent with other studies involving the covalent incorporation of Ru—NHC complexes into $SiO_2$ and PMMA.[52,53] No degradation of chemically-synthesized ABTS·⁻ in PBS solutions containing Ru7-$SiO_2$ or Ru9-PMMA, but subsequent addition of EtOH did cause the absorbance at 734 nm to decrease linearly ($k_{obs}$=5.7 and 4.9×10⁻⁸ M s⁻¹ for Ru7-$SiO_2$ and Ru9-PMMA, respectively), indicating that these materials gained the ability to catalytically reduce ABTS·⁻ via the covalent incorporation of SRACs.

After determining the general strategy of endowing an AIM with the ability to catalytically degrade radicals by covalently incorporating an SRAC was feasible, we then sought to obtain preliminary evidence that SRAC activity could be retained on an AIM exposed to RAW 264.7 macrophage cell culture (DMEM, 10% FBS, 1% penicillin/streptomycin, 5% humidified $CO_2$, 37° C.) in collaboration with Dr. Nilofer Qureshi (UMKC, letter provided). Because ABTS·⁻ itself was unstable in DMEM and all other cell culture media tested, direct measurement of the ABTS·⁻ degrading activity of SRAC-AIMs in cellular environments was impossible. Thus, a method was needed to physically separate SRAC-AIMs from cellular environments to enable transfer to PBS. Reaction of Ru7 with $SiO_2$-coated magnetic microspheres ($SiO_2$@MM, 1.5 μm, Corpuscular Inc.) afforded Ru7-$SiO_2$@MM, an SRAC-AIM which could be separated from cell cultures by using a magnet. Next, Ru7-$SiO_2$@MM was added to RAW 264.7 cell culture, magnetically separated after 24 h, then washed with DMEM and PBS. The ability of Ru7-$SiO_2$@MM to catalyze ABTS·⁻ reduction in PBS (using EtOH as the terminal reductant) was retained after the 24 h exposure to the RAW 264.7 cell culture (5.2 and 4.8×10⁻⁸ M s⁻¹ before and after, respectively).

The results demonstrate that our Ru—NHC complexes catalyze radical reduction and inhibit their formation by ROS through a transfer hydrogenation-like process. Other Ru complexes have been reported to be cytotoxic or cause ROS formation,[54-56] but neither behavior was observed with our Ru—NHC complexes. No ABTS·⁻ formation was observed upon addition of $H_2O_2$ to Ru1 or Ru2 and ABTS²⁻, providing evidence that Ru1 and Ru2 do not generate ROS. Treatment of RAW 264.7 cells with up to 100 μM Ru1 or Ru2 for 24 h resulted in no loss of cell viability (measured via the MTT assay), indicating that Ru1 and Ru2 are not cytotoxic. A recent study suggested that Ru—NHC complexes may be selectively cytotoxic to some cell types, which could explain the different behaviors reported in the literature.[57] Collectively, the results confirm the feasibility of our proposed approach.

Example 5

Figure 20:
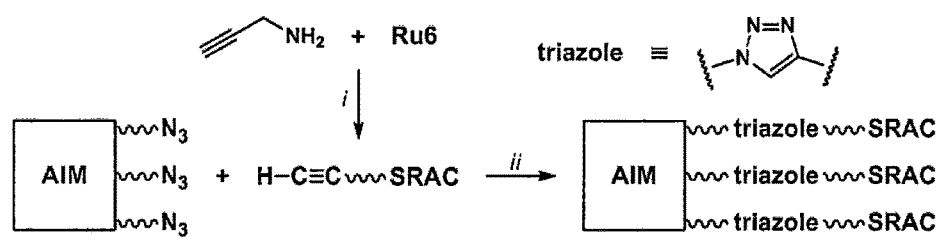
FIG. 20 shows the synthesis of SRAC with C≡C—H and coupling to N$_3$-functionalized AIM. Conditions: (i) same as for Ru7, (ii) 1:1 alkyne/azide, 10 mol % CuSO$_4$.5H$_2$O, 3 equiv. sodium ascorbate, r.t., 48 h.

Triethoxysilane groups such as those found in Ru7 readily react with surface hydroxyl groups on inorganic oxides to eliminate EtOH and form new Si—O bonds, therefore Ru7 will be covalently incorporated into $TiO_2$ and hydroxyapatite,[61,62] similar to Ru7-$SiO_2$ (see Example 4). Surface functionalization of titanium[63] and stainless steel[64] with oxide and hydroxide groups will thus enable covalent incorporation of Ru7 by this approach as well. Although SRAC-functionalized PMMA (e.g. Ru9-PMMA) can be prepared by building a Ru—NHC complex into a monomer (e.g. Ru9) and then polymerizing MMA in its presence, this approach may be impractical for some polymers. Alternatively, amide coupling[48] of propargyl amine to Ru6 will produce an SRAC with a C≡C—H group, which can then undergo Cu-catalyzed alkyne-azide coupling[65] with azide-functionalized polyethylene (PE), polypropylene (PP) or PTFE to afford an AIM with a triazole linked SRAC (FIG. 20). Hydroxy-functionalized PE, PP and PTFE will be reacted with $MeSO_3Cl$ followed by $NaN_3$ to access the desired azide-functionalized polymers.[66]

The foregoing is illustrative of the present invention, and is not to be construed as limiting thereof. The invention is defined by the following claims, with equivalents of the claims to be included therein. All publications, patent applications, patents, patent publications, and other references cited herein are incorporated by reference in their entireties for the teachings relevant to the sentence and/or paragraph in which the reference is presented.

That which is claimed is:

1. A compound represented by one of the following structures:

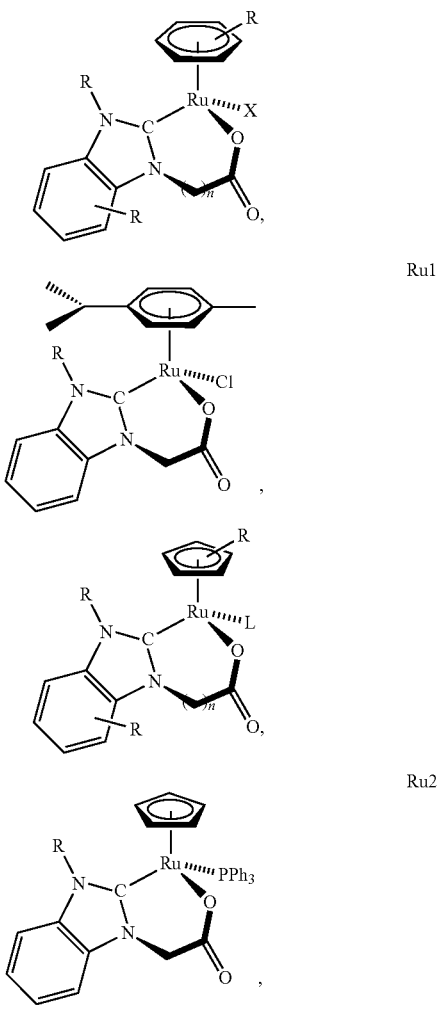

-continued

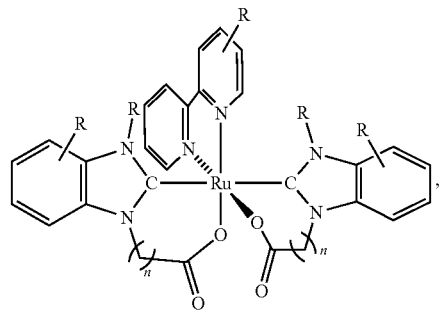

Ru3

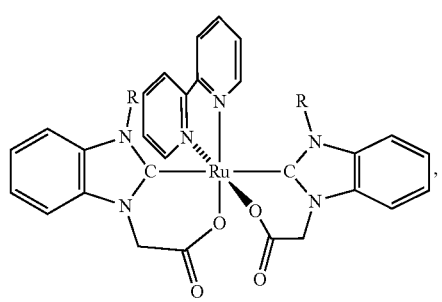

[1+]X⊖,

Ru4

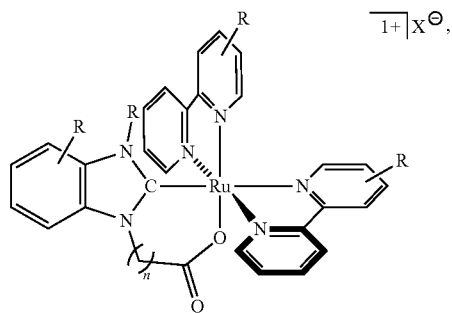

[1+]X⊖,

Ru5

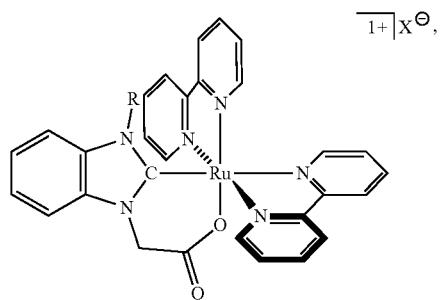

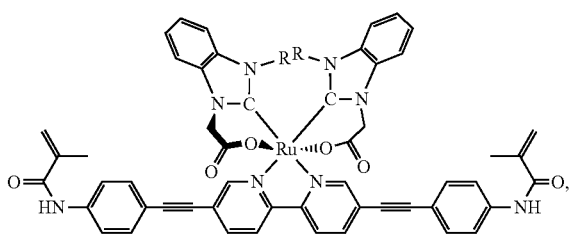

-continued

Ru6

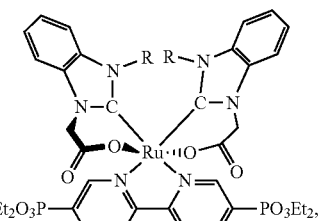

Ru7

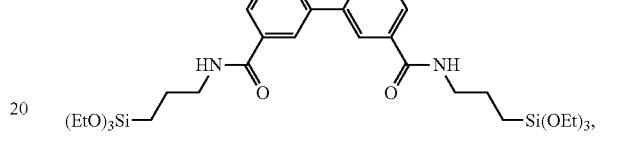

Ru9

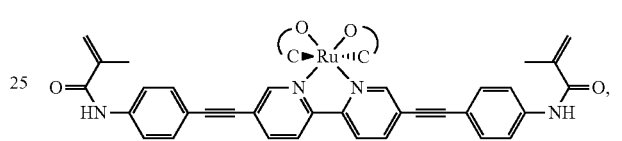

Ru10

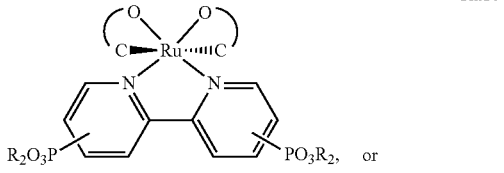   or

Ru-PPE

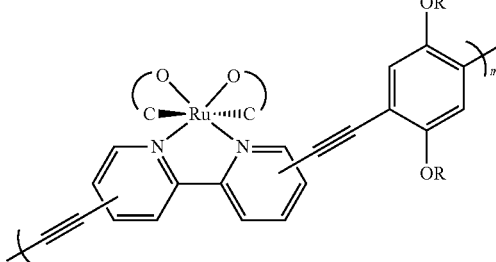

wherein 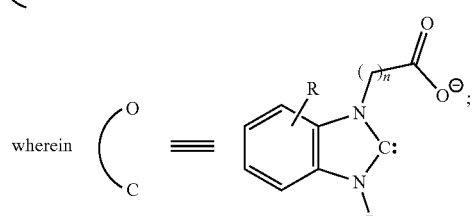

each R is independently a hydrogen, substituted or unsubstituted alkyl group, or a substituted or unsubstituted aryl group, wherein the substituted alkyl group or the substituted aryl group are substituted with a substituent selected from the group consisting of an alkyl group, alkenyl group, alkynyl group, halogen atom, carbonyl-containing functional group, aryl group, heterocycle, alcohol, thiol, amine, ether, thioether, azide, and any combination thereof;

X is a non-coordinating anion;

n is an integer from 1 to 30; and m is an integer from 1 to 30;

and/or a derivative thereof.

2. The compound of claim 1, wherein R in each occurrence is hydrogen.

3. A biomedical implant material comprising the compound of claim 1, wherein the compound is present on at least a portion of a surface of the biomedical implant material.

4. The biomedical implant material of claim 3, wherein the compound degrades a radical and/or reactive oxygen species (ROS) catalytically.

5. The biomedical implant material of claim 4, wherein the compound reduces the radical and/or ROS catalytically.

6. The biomedical implant material of claim 3, wherein the compound is regenerated after a radical degradation reaction and, after regeneration, the compound can catalytically degrade a radical and/or ROS.

7. The biomedical implant material of claim 3, wherein the compound is not consumed after a radical degradation reaction.

8. The biomedical implant material of claim 3, wherein the compound is covalently attached to the biomedical implant material.

9. A method of decreasing and/or preventing damage to a biomedical implant material, the method comprising:
providing the biomedical implant material, the biomedical implant material
comprising a self-regenerating antioxidant catalyst on at least a portion of a surface of the biomedical implant material, thereby decreasing and/or preventing damage to the biomedical implant material.

10. The method of claim 9, wherein the self-regenerating antioxidant catalyst decreases and/or prevents damage to the biomedical implant material by decreasing and/or preventing damage to the biomedical implant from a radical and/or reactive oxygen species (ROS).

11. The method of claim 9, wherein the self-regenerating antioxidant catalyst decreases severity and/or duration of a sterile immune response in a subject.

12. The method of claim 9, wherein the self-regenerating antioxidant catalyst decreases severity and/or duration of adverse effects of acute phase foreign body reaction in a subject.

13. The method of claim 9, wherein the self-regenerating antioxidant catalyst reduces a radical and/or reactive oxygen species (ROS) catalytically.

14. The method of claim 9, wherein the self-regenerating antioxidant catalyst is regenerated after a radical degradation reaction and, after regeneration, the self-regenerating antioxidant catalyst can catalytically degrade a radical and/or reactive oxygen species (ROS).

15. The method of claim 9, wherein the self-regenerating antioxidant catalyst is not consumed after a radical degradation reaction.

16. The method of claim 9, wherein the self-regenerating antioxidant catalyst comprises a chelating, anionic benzimidazole-based N-heterocyclic carbene (NHC) ligand.

17. The method of claim 9, wherein the self-regenerating antioxidant catalyst comprises a bipyridine, phosphine, and/or amine ligand.

18. The method of claim 9, wherein the self-regenerating antioxidant catalyst comprises at least one compound of claim 1.

19. The method of claim 9, wherein the biomedical implant material is covalently functionalized with the self-regenerating antioxidant catalyst.

20. The method of claim 9, wherein the self-regenerating antioxidant catalyst is present on the biomedical implant material in a therapeutically effective amount.

* * * * *

UNITED STATES PATENT AND TRADEMARK OFFICE
CERTIFICATE OF CORRECTION

PATENT NO. : 9,751,081 B2
APPLICATION NO. : 14/955936
DATED : September 5, 2017
INVENTOR(S) : Tennyson et al.

It is certified that error appears in the above-identified patent and that said Letters Patent is hereby corrected as shown below:

On the Title Page

Item (56) References Cited, Other Publications, Chung et al. cite:
Please correct "CNC" to read -- C^N^C --

Item (56) References Cited, Other Publications, Guo et al. cite:
Please correct "binuclear" to read -- Dinuclear --

Item (56) References Cited, Other Publications, Johnson et al. cite:
Please correct "[Fe$_4$S$_4$(SR)$_4$]$_2$-" to read -- [Fe$_4$S$_4$(SR)$_4$]$^{2-}$ --

Item (56) References Cited, Other Publications, Tomson et al. cite:
Please correct "62-diketiminato" to read -- β-diketiminato --

In the Specification

Column 4, Line 7, formula 1⁻: Please correct " 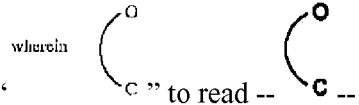 " to read -- 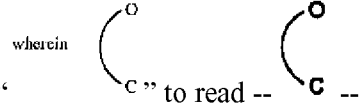 --

Column 18, Line 7, formula 1⁻: Please correct " " to read --  --

Column 24, Line 10: Please correct "(2.0.5H$_2$O)" to read -- (2·0.5H$_2$O) --

Column 29, Line 1: Please correct "111.4±2.00" to read -- 111.4±2.0° --

Column 30, Line 40: Please correct "KOtBu" to read -- KO$^t$Bu --

Signed and Sealed this
Tenth Day of July, 2018

Andrei Iancu
*Director of the United States Patent and Trademark Office*

Column 37, Line 21: Please correct "(Ru3.2MeOTf)" to read -- (Ru3·2MeOTf) --

Column 37, Line 22: Please correct "(Ru4.MeOTf)" to read -- (Ru4·MeOTf) --

Column 37, Line 25: Please correct "Ru3.2MeOTf" to read -- Ru3·2MeOTf --

Column 37, Line 26: Please correct "Ru4.MeOTf" to read -- Ru4·MeOTf --

Column 37, Line 27: Please correct "Ru3.2MeOTf" to read -- Ru3·2MeOTf --

Column 37, Line 29: Please correct "Ru4.MeOTf" to read -- Ru4·MeOTf --

Column 37, Line 31: Please correct "Ru3.2MeOTf" to read -- Ru3·2MeOTf --

Column 37, Line 35: Please correct "Ru3.2MeOTf" to read -- Ru3·2MeOTf --

Column 37, Line 35: Please correct "Ru4.MeOTf" to read -- Ru4·MeOTf --

Column 39, Line 56: Please correct "(2.0.5H$_2$O)" to read -- (2·0.5H$_2$O) --

Column 40, Line 24: Please correct "(4.H$_2$O)" to read -- (4·H$_2$O) --

Column 40, Line 28: Please correct "(Ru3.2MeOTf)" to read -- (Ru3·2MeOTf) --

Column 40, Line 45: Please correct "acetone-ds" to read -- acetone-d$_5$ --

Column 40, Line 47: Please correct "(5.0.5H$_2$O)" to read -- (5·0.5H$_2$O) --

Column 40, Line 50: Please correct "(Ru4.MeOTf)" to read -- (Ru4·MeOTf) --

Column 42, Line 55, Scheme 4: Please correct "relux" to read -- reflux --

Column 42, Line 55, Scheme 4: Please correct "(μ-Cl)]" to read -- (μ-Cl)]$_2$ --

Column 43, Line 36: Please correct "(Ru3.2MeOTf)" to read -- (Ru3·2MeOTf) --

Column 43, Line 38: Please correct "Ru3.2MeOTf" to read -- Ru3·2MeOTf --

Column 43, Line 63, Scheme 5 (see Mark-up Copy): Please replace

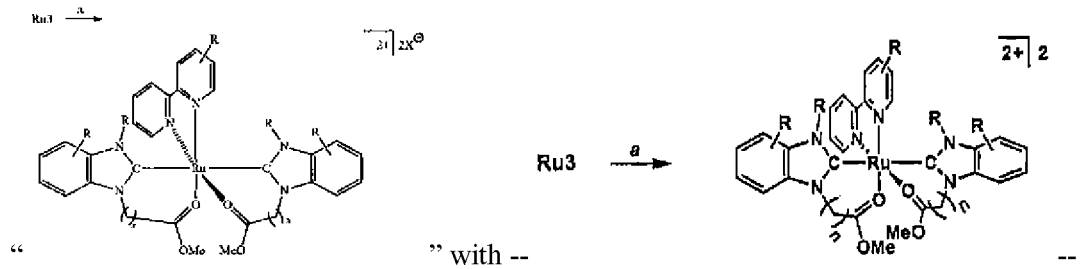

CERTIFICATE OF CORRECTION (continued)
U.S. Pat. No. 9,751,081 B2

Column 44, Line 25: Please correct "(Ru4.MeOTf)" to read -- (Ru4·MeOTf) --

Column 44, Line 27: Please correct "Ru4.MeOTf" to read -- Ru4·MeOTf --

Column 44, Line 29: Please correct "Ru4.MeOTf" to read -- Ru4·MeOTf --

Column 44, Line 36: Please correct "Ru4.MeOTf" to read -- Ru4·MeOTf --

Column 44, Line 39: Please correct "Ru3.2MeOTf" to read -- Ru3·2MeOTf --

Column 44, Line 46: Please correct "Ru3.2MeOTf" to read -- Ru3·2MeOTf --

Column 44, Line 48: Please correct "Ru3.2MeOTf" to read -- Ru3·2MeOTf --

Column 44, Line 52: Please correct "Ru3.2MeOTf" to read -- Ru3·2MeOTf --

Column 44, Line 52: Please correct "Ru4.MeOTf" to read -- Ru4·MeOTf --

Column 44, Line 53: Please correct "THF-ds" to read -- THF-$d_8$ --

Column 44, Line 67: Please correct "[12]" to read -- [17] --

Column 45, Line 10: Please correct "Ru3.2MeOTf" to read -- Ru3·2MeOTf --

Column 45, Line 11: Please correct "Ru3.2MeOTf" to read -- Ru3·2MeOTf --

Column 45, Line 14: Please correct "Ru3*2MeOTf" to read -- Ru3·2MeOTf --

Column 45, Line 20: Please correct "Ru3.2MeOTf" to read -- Ru3·2MeOTf --

Column 45, Line 23: Please correct "Ru3.2MeOTf" to read -- Ru3·2MeOTf --

Column 45, Line 25: Please correct "Ru3.2MeOTf" to read -- Ru3·2MeOTf --

Column 45, Line 28: Please correct "Ru3.2MeOTf" to read -- Ru3·2MeOTf --

Column 45, Line 32: Please correct "Ru3.2MeOTf" to read -- Ru3·2MeOTf --

Column 45, Line 37: Please correct "Ru3.2MeOTf" to read -- Ru3·2MeOTf --

Column 45, Line 39: Please correct "Ru3.2MeOTf" to read -- Ru3·2MeOTf --

Column 45, Line 40: Please correct "Ru3.2MeOTf" to read -- Ru3·2MeOTf --

Column 45, Line 43: Please correct "Ru3.2MeOTf" to read -- Ru3·2MeOTf --

Column 45, Line 53: Please correct "Ru4.MeOTf" to read -- Ru4·MeOTf --

Column 45, Line 55: Please correct "Ru4.MeOTf" to read -- Ru4·MeOTf --

Column 45, Line 57: Please correct "Ru3.2MeOTf" to read -- Ru3·2MeOTf --

Column 45, Line 58: Please correct "Ru4.MeOTf" to read -- Ru4·MeOTf --

Column 45, Line 59: Please correct "Ru3.2MeOTf" to read -- Ru3·2MeOTf --

Column 45, Line 60: Please correct "Ru4.MeOTf" to read -- Ru4·MeOTf --

Column 45, Line 66: Please correct "Ru3.2MeOTf" to read -- Ru3·2MeOTf --

Column 45, Line 67: Please correct "Ru4.MeOTf" to read -- Ru4·MeOTf --

Column 46, Line 1: Please correct "Ru3.2MeOTf" to read -- Ru3·2MeOTf --

Column 46, Line 2: Please correct "Ru4.MeOTf" to read -- Ru4·MeOTf --

Column 46, Line 5: Please correct "Ru3.2MeOTf" to read -- Ru3·2MeOTf --

Column 46, Line 8: Please correct "Ru4.MeOTf" to read -- Ru4·MeOTf --

Column 46, Line 10: Please correct "Ru3.2MeOTf" to read -- Ru3·2MeOTf --

Column 46, Line 11: Please correct "Ru4.MeOTf" to read -- Ru4·MeOTf --

Column 46, Line 20: Please correct "Ru3.2MeOTf" to read -- Ru3·2MeOTf --

Column 46, Line 23: Please correct "Ru4.MeOTf" to read -- Ru4·MeOTf --

Column 46, Line 27: Please correct "Ru3.2MeOTf" to read -- Ru3·2MeOTf --

Column 46, Line 28: Please correct "Ru4.MeOTf" to read -- Ru4·MeOTf --

Column 46, Line 30: Please correct "Ru3.2MeOTf" to read -- Ru3·2MeOTf --

Column 46, Line 31: Please correct "Ru4.MeOTf" to read -- Ru4·MeOTf --

Column 46, Line 35: Please correct "Ru3.2MeOTf" to read -- Ru3·2MeOTf --

Column 46, Line 37: Please correct "Ru4.MeOTf" to read -- Ru4·MeOTf --

Column 46, Line 41: Please correct "Ru3.2MeOTf" to read -- Ru3·2MeOTf --

CERTIFICATE OF CORRECTION (continued)
U.S. Pat. No. 9,751,081 B2

Column 46, Line 42: Please correct "Ru4.MeOTf" to read -- Ru4·MeOTf --

Column 46, Line 47: Please correct "Ru3.2MeOTf" to read -- Ru3·2MeOTf --

Column 46, Line 47: Please correct "Ru4.MeOTf" to read -- Ru4·MeOTf --

Column 46, Line 56: Please correct "(Ru3.2MeOTf)" to read -- (Ru3·2MeOTf) --

Column 46, Line 58: Please correct "(Ru4.MeOTf)" to read -- (Ru4·MeOTf) --

Column 46, Line 65: Please correct "Ru3.2MeOTf" to read -- Ru3·2MeOTf --

Column 46, Line 67: Please correct "Ru4.MeOTf" to read -- Ru4·MeOTf --

Column 47, Line 5: Please correct "Ru3.2MeOTf" to read -- Ru3·2MeOTf --

Column 47, Line 5: Please correct "Ru4.MeOTf" to read -- Ru4·MeOTf --

Column 47, Line 9: Please correct "Ru3.2MeOTf" to read -- Ru3·2MeOTf --

Column 48, Line 48: Please correct "isopropanol-dg" to read -- isopropanol-$d_8$ --

Column 52, Line 20: Please correct "aliquotst" to read -- aliquots$^\ddagger$ --

Column 55, Line 53: Please correct "[($L_n$Ru–OH).EtOH]" to read -- [($L_n$Ru–OH)·EtOH] --

Column 55, Line 55: Please correct "[($L_n$Ru–OEt).$H_2O$]" to read -- [($L_n$Ru–OEt)·$H_2O$] --

Column 55, Line 56: Please correct "[($L_n$Ru–OEt).$H_2O$]" to read -- [($L_n$Ru–OEt)·$H_2O$] --

Column 55, Lines 59-60: Please correct "[($L_n$Ru–H).MeC(=O)H]" to read -- [($L_n$Ru–H)·MeC(=O)H] --

Column 57, Line 1: Please correct "$\mu^6$-cymene" to read -- $\eta^6$-cymene --

Column 57, Line 33: Please correct "($\mu^5$-$C_5H_5$)" to read -- ($\eta^5$-$C_5H_5$) --

Column 58, Line 59, Table 4: Please correct "$\Delta H^\dagger$" to read -- $\Delta H^\ddagger$ --

Column 59, Line 49, Table 5: Please correct "$10^{-s}$" to read -- $10^{-5}$ --

Column 64, Line 55: Please correct "Mn=24.2" to read -- $M_n$=24.2 --